(12) United States Patent
Maglia et al.

(10) Patent No.: US 11,169,138 B2
(45) Date of Patent: Nov. 9, 2021

(54) NANOPORES WITH INTERNAL PROTEIN ADAPTORS

(71) Applicants: KATHOLIEKE UNIVERSITEIT LEUVEN, Leuven (BE); RIJKSUNIVERSITEIT GRONINGEN, Groningen (NL)

(72) Inventors: Giovanni Maglia, Glimmen (NL); Mikhael Soskine, Drachten (NL); Annemie Biesemans, Kessel-Lo (BE); Veerle Van Meervelt, Holsbeek (BE); Bert Poolman, Haren (NL); Gea Schuurman-Wolters, Nietap (NL)

(73) Assignees: Katholieke Universiteit Leuven, Leuven (BE); Rijksuniversiteit Groningen, Groningen (NL)

( * ) Notice: Subject to any disclaimer, the term of this patent is extended or adjusted under 35 U.S.C. 154(b) by 412 days.

(21) Appl. No.: 15/566,577

(22) PCT Filed: Apr. 14, 2016

(86) PCT No.: PCT/EP2016/058252
§ 371 (c)(1),
(2) Date: Oct. 13, 2017

(87) PCT Pub. No.: WO2016/166232
PCT Pub. Date: Oct. 20, 2016

(65) Prior Publication Data
US 2018/0209952 A1    Jul. 26, 2018

(30) Foreign Application Priority Data

Apr. 14, 2015 (GB) .................................... 1506307
Apr. 29, 2015 (GB) .................................... 1507264

(51) Int. Cl.
*G01N 33/487* (2006.01)
*G01N 33/68* (2006.01)
*G01N 27/447* (2006.01)

(52) U.S. Cl.
CPC . *G01N 33/48721* (2013.01); *G01N 27/44791* (2013.01); *G01N 33/6872* (2013.01)

(58) Field of Classification Search
CPC .................. G01N 33/48721; G01N 27/44791
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |
| 6,114,121 A | 9/2000 | Fujiwara et al. | |
| 6,362,002 B1 | 3/2002 | Denison et al. | |
| 6,426,231 B1 | 7/2002 | Bayley et al. | |
| 6,627,067 B1 | 9/2003 | Branton et al. | |
| 6,824,659 B2 | 11/2004 | Bayley et al. | |
| 6,863,833 B1 | 3/2005 | Bloom et al. | |
| 6,916,665 B2 | 7/2005 | Bayley et al. | |
| 6,927,070 B1 | 8/2005 | Bayley et al. | |
| 7,189,503 B2 | 3/2007 | Akeson et al. | |
| 8,105,846 B2* | 1/2012 | Bayley ................. | C12Q 1/6869 204/400 |
| 8,785,211 B2 | 7/2014 | Bayley et al. | |
| 8,822,160 B2 | 9/2014 | Bayley et al. | |
| 8,828,208 B2 | 9/2014 | Canas et al. | |
| 9,073,990 B2 | 7/2015 | Paas et al. | |
| 9,127,313 B2 | 9/2015 | Brown et al. | |
| 9,222,082 B2 | 12/2015 | Jayasinghe et al. | |
| 9,447,152 B2 | 9/2016 | Clarke et al. | |
| 9,562,887 B2 | 2/2017 | Maglia et al. | |
| 9,580,480 B2 | 2/2017 | Lu et al. | |
| 9,588,079 B2 | 3/2017 | Gundlach et al. | |
| 9,732,381 B2 | 8/2017 | Stoddart et al. | |
| 9,751,915 B2 | 9/2017 | Clarke et al. | |
| 9,777,049 B2 | 10/2017 | Bruce et al. | |
| 10,006,905 B2* | 6/2018 | Maglia ................. | C07K 14/255 |
| 10,167,503 B2 | 1/2019 | Clarke et al. | |
| 10,266,885 B2 | 4/2019 | Jayasinghe et al. | |
| 10,385,389 B2 | 8/2019 | Heron et al. | |
| 10,400,014 B2 | 9/2019 | Howorka et al. | |
| 10,443,097 B2 | 10/2019 | Jayasinghe et al. | |
| 10,472,673 B2 | 11/2019 | Maglia et al. | |
| 10,514,378 B2 | 12/2019 | Maglia et al. | |
| 10,669,581 B2 | 6/2020 | Stoddart et al. | |
| 10,844,432 B2 | 11/2020 | Jayasinghe et al. | |
| 10,882,889 B2 | 1/2021 | Bruce et al. | |

(Continued)

FOREIGN PATENT DOCUMENTS

| CA | 2381139 A1 | 3/2001 |
|---|---|---|
| CN | 102116783 A | 7/2011 |

(Continued)

OTHER PUBLICATIONS

European Office Communication from EP Application No. EP 16719292.1, dated Sep. 19, 2018.

(Continued)

*Primary Examiner* — Ruixiang Li

(74) *Attorney, Agent, or Firm* — Wolf, Greenfield & Sacks, P.C.

(57) ABSTRACT

A method for detecting an analyte in a sample includes the steps of obtaining a nanopore sensor comprising a nanopore and a protein adaptor internalized in the lumen of the nanopore, adding a sample comprising an analyte to the cis side or the trans side of the nanopore, and measuring conductance across the nanopore. A change in conductance after adding the sample indicates the analyte is present in the sample and has bound to the protein adaptor. Nanopore sensors comprise a nanopore and a protein adaptor internalized in the lumen of the nanopore. The protein adaptor is a functional enzyme or ligand-binding protein.

17 Claims, 16 Drawing Sheets

Specification includes a Sequence Listing.

(56) References Cited

U.S. PATENT DOCUMENTS

| | | |
|---|---|---|
| 10,975,428 B2 | 4/2021 | Jayasinghe et al. |
| 10,976,300 B2 | 4/2021 | Maglia et al. |
| 10,976,311 B2 | 4/2021 | Maglia et al. |
| 10,995,372 B2 | 5/2021 | Jayasinghe et al. |
| 11,034,734 B2 | 6/2021 | Howorka et al. |
| 2002/0028458 A1 | 3/2002 | Lexow |
| 2002/0094526 A1 | 7/2002 | Bayley et al. |
| 2002/0197614 A1 | 12/2002 | Mosaic |
| 2003/0044816 A1 | 3/2003 | Denison et al. |
| 2003/0099951 A1 | 5/2003 | Akeson et al. |
| 2003/0165936 A1 | 9/2003 | Rabbani et al. |
| 2003/0211502 A1 | 11/2003 | Sauer et al. |
| 2003/0215881 A1 | 11/2003 | Bayley et al. |
| 2004/0214177 A1 | 10/2004 | Bension |
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2007/0218471 A1 | 9/2007 | Kim et al. |
| 2008/0311582 A1 | 12/2008 | Bayley et al. |
| 2009/0256116 A1 | 10/2009 | Shumaker-Parry et al. |
| 2009/0283412 A1 | 11/2009 | Sansinena et al. |
| 2009/0298075 A1 | 12/2009 | Travers et al. |
| 2009/0298188 A1 | 12/2009 | Peti-Peterdi |
| 2010/0120098 A1 | 5/2010 | Grunenwald et al. |
| 2010/0196203 A1 | 8/2010 | Sanghera et al. |
| 2010/0297638 A1 | 11/2010 | Bayley et al. |
| 2011/0120871 A1 | 5/2011 | Reid et al. |
| 2011/0121840 A1 | 5/2011 | Sanghera et al. |
| 2011/0177498 A1 | 7/2011 | Clarke et al. |
| 2011/0229877 A1 | 9/2011 | Jayasinghe et al. |
| 2011/0311965 A1 | 12/2011 | Maglia et al. |
| 2012/0058468 A1 | 3/2012 | McKeown |
| 2012/0064599 A1 | 3/2012 | Jayasinghe et al. |
| 2012/0100530 A1 | 4/2012 | Moysey et al. |
| 2012/0107802 A1 | 5/2012 | Stoddart et al. |
| 2012/0322679 A1 | 12/2012 | Brown et al. |
| 2014/0051069 A1 | 2/2014 | Jayasinghe et al. |
| 2014/0186823 A1 | 7/2014 | Clarke et al. |
| 2014/0262784 A1 | 9/2014 | Clarke et al. |
| 2014/0296083 A1 | 10/2014 | Brown et al. |
| 2015/0008126 A1 | 1/2015 | Maglia et al. |
| 2015/0031020 A1 | 1/2015 | Jayasinghe et al. |
| 2015/0068904 A1 | 3/2015 | Bruce et al. |
| 2015/0175663 A1 | 6/2015 | Yokoi et al. |
| 2015/0177237 A1 | 6/2015 | Turner et al. |
| 2015/0346149 A1 | 12/2015 | Brown et al. |
| 2016/0005330 A1 | 1/2016 | Maglia et al. |
| 2016/0010147 A1 | 1/2016 | Heron et al. |
| 2016/0370358 A1 | 12/2016 | Maglia et al. |
| 2017/0058337 A1 | 3/2017 | Clarke et al. |
| 2017/0058338 A1 | 3/2017 | Jayasinghe et al. |
| 2017/0107569 A1 | 4/2017 | Heron et al. |
| 2017/0233803 A1 | 8/2017 | Stoddart et al. |
| 2017/0306398 A1 | 10/2017 | Jayasinghe et al. |
| 2018/0030526 A1 | 2/2018 | Brown et al. |
| 2018/0095066 A1 | 4/2018 | Jayasinghe et al. |
| 2018/0148481 A2 | 5/2018 | Howorka et al. |
| 2018/0208632 A1 | 7/2018 | Bruce et al. |
| 2018/0334707 A1 | 11/2018 | Stoddart et al. |
| 2018/0335425 A1 | 11/2018 | Maglia et al. |
| 2018/0364214 A1 | 12/2018 | Maglia et al. |
| 2019/0071721 A1 | 3/2019 | Jayasinghe et al. |
| 2019/0202876 A1 | 7/2019 | Jayasinghe et al. |
| 2019/0300582 A1 | 10/2019 | Jayasinghe et al. |
| 2019/0330282 A1 | 10/2019 | Jayasinghe et al. |
| 2019/0346431 A1 | 11/2019 | Maglia et al. |
| 2020/0017556 A1 | 1/2020 | Howorka et al. |
| 2020/0072824 A1 | 3/2020 | Maglia et al. |
| 2020/0087724 A1 | 3/2020 | Heron et al. |
| 2020/0224262 A1 | 7/2020 | Jayasinghe et al. |
| 2020/0407785 A1 | 12/2020 | Stoddart et al. |
| 2021/0139972 A1 | 5/2021 | Jayasinghe et al. |

FOREIGN PATENT DOCUMENTS

| | | |
|---|---|---|
| CN | 102174554 A | 9/2011 |
| CN | 102317310 A | 1/2012 |
| CN | 103460040 A | 12/2013 |
| CN | 201680034399.2 | 10/2020 |
| EP | 2194123 B1 | 8/2012 |
| EP | 2682460 A1 | 1/2014 |
| GB | 2453377 A | 4/2009 |
| JP | H10-146190 A | 6/1998 |
| JP | 2005-253427 A | 9/2005 |
| JP | 2015-514128 A | 5/2015 |
| WO | WO 1999/005167 A1 | 2/1999 |
| WO | WO 2000/028312 A1 | 5/2000 |
| WO | WO 2001/042782 A1 | 6/2001 |
| WO | 0159453 A2 | 8/2001 |
| WO | WO 2002/042496 A2 | 5/2002 |
| WO | WO 2003/095669 A1 | 11/2003 |
| WO | WO 2006/028508 A2 | 3/2006 |
| WO | WO 2006/100484 A2 | 9/2006 |
| WO | WO 2007/057668 A1 | 5/2007 |
| WO | WO 2007/075987 A2 | 7/2007 |
| WO | WO 2007/084103 A2 | 7/2007 |
| WO | WO 2008/102120 A1 | 8/2008 |
| WO | WO 2008/102121 A1 | 8/2008 |
| WO | WO 2008/124107 A1 | 10/2008 |
| WO | WO 2009/024775 A1 | 2/2009 |
| WO | WO 2009/035647 A1 | 3/2009 |
| WO | WO 2009/044170 A1 | 4/2009 |
| WO | WO 2009/077734 A2 | 6/2009 |
| WO | WO 2009/143425 A1 | 11/2009 |
| WO | WO 2010/004265 A1 | 1/2010 |
| WO | WO 2010/004273 A1 | 1/2010 |
| WO | WO 2010/034018 A2 | 3/2010 |
| WO | 2010055307 A1 | 5/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/122293 A1 | 10/2010 |
| WO | WO 2011/067559 A1 | 6/2011 |
| WO | WO 2012/042226 A2 | 4/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/109970 A1 | 7/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A1 | 5/2014 |
| WO | WO 2014/064444 A1 | 5/2014 |
| WO | 2014122654 A2 | 8/2014 |
| WO | 2014153047 A1 | 9/2014 |
| WO | WO 2014/135838 A1 | 9/2014 |
| WO | 2014153625 A1 | 10/2014 |
| WO | WO 2015/022544 A1 | 2/2015 |
| WO | WO 2015/051378 A1 | 4/2015 |
| WO | WO 2015/055981 A2 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |
| WO | WO 2015/166275 A1 | 11/2015 |
| WO | WO 2015/166276 A1 | 11/2015 |
| WO | WO 2016/055778 A1 | 4/2016 |
| WO | WO 2016/166232 A1 | 10/2016 |

OTHER PUBLICATIONS

Office Action from corresponding European Application No. 16719292. 1, dated Nov. 15, 2019.

Aravind et al., "The DNA-Repair Protein AlkB, EGL-9, and Leprecan Define New Families of 2-Oxoglutarate- and Iron-Dependent Dioxygenases," Genome Biology, vol. 2, Feb. 19, 2001, pp. 1-8.

(56) References Cited

OTHER PUBLICATIONS

Ashton et al., "MinION Nanopore Sequencing Identifies the Position and Structure of a Bacterial Antibiotic Resistance Island," Nature Biotechnology, vol. 33, No. 3, Mar. 2015, pp. 296-302.
Atkins et al., "Structure-Function Relationships of a Novel Bacterial Toxin, Hemolysin E. The Role of alpha G," Journal of Biological Chemistry, vol. 275, No. 52, Dec. 29, 2000, pp. 41150-41155.
Bayley, "Nanopore Sequencing: From Imagination to Reality," Clinical Chemistry, vol. 61, No. 1, 2015, pp. 25-31.
Bezrukov et al., "Counting Polymers Moving Through a Single Ion Channel," Nature, vol. 370, Jul. 28, 1994, pp. 279-281.
Bleijlevens et al., "Dynamic States of the DNA Repair Enzyme AlkB Regulate Product Release," European Molecular Biology Organization, vol. 9, No. 9, Jul. 11, 2008, pp. 872-877.
Bleijlevens et al., "Changes in Protein Dynamics of the DNA Repair Dioxygenase AlkB Upon Binding of FE2+ and 2-Oxoglutarate," Biochemistry, vol. 51, Mar. 26, 2012, pp. 3334-3341.
Braha et al., "Carriers Versus Adapters in Stochastic Sensing," ChemPhysChem, vol. 6, 2005, pp. 889-892.
Chin et al., "The Metabolite α-Ketoglutarate Extends Lifespan by Inhibiting ATP Synthase and TOR," Nature, vol. 510, Jun. 19, 2014, pp. 397-401.
Fahie et al., "Resolved Single-Molecule Detection of Individual Species Within a Mixture of Anti-Biotin Antibodies Using an Engineered Monometric Nanopore," American Chemical Society, vol. 9, No. 2, Jan. 9, 2015, pp. 1089-1098.
Franceschini et al., "A Nanopore Machine Promotes the Vectorial Transport of DNA Across Membranes," Nature Communications, vol. 4, No. 2415, Sep. 12, 2013, pp. 1-8.
Freedman et al., "Single Molecule Unfolding and Stretching of Protein Domains Inside a Solid-State Nanopore by Electric Field," Scientific Reports, vol. 3, No. 1638, Apr. 10, 2013, pp. 1-8.
Gilbert et al., "Two Structural Transitions in Membrane Pore Formation by Pneumolysin, the Pore-Forming Toxin of *Streptococcus Pneumoniae*," Cell, vol. 97, May 28, 1999, pp. 647-655.
Gouridis et al., "Conformational Dynamics in Substrate-Binding Domains Influences Transport in the ABC Importer GInPQ," Nature Structural & Molecular Biology, vol. 22, No. 1, Dec. 8, 2014, pp. 57-66.
Great Britain Search Report from GB Application No. GB1507264.8, dated Jan. 29, 2016.
Gu et al., "Stochastic Sensing of Organic Analytes by a Pore-Forming Protein Containing a Molecular Adapter," Nature, vol. 398, Apr. 22, 1999, pp. 686-690.
Howorka et al., "Nanopore Analytics: Sensing of Single Molecules," The Royal Society of Chemistry, vol. 38, Jun. 15, 2009, pp. 2360-2384.
International Preliminary Report on Patentability from EP Application No. PCT/EP2016/058252, dated Oct. 17, 2017.
International Search Report from PCT Application No. PCT/BE2014/000013, dated Aug. 5, 2014.
International Search Report and Written Opinion from PCT Application No. PCT/EP2016/058252, dated Jul. 15, 2016.
Jung et al., "The Internal Cavity of the Staphylococcal α-Hemolysin Pore Accommodates-175 Exogenous Amino Acid Residues," Biochemistry, vol. 44, No. 25, Jun. 28, 2005, pp. 8919-8929.
Luchian et al., "Single-Molecule Covalent Chemistry With Spatially Separated Reactants," Angew. Chem. Int. Ed., vol. 42, 2003, pp. 3766-3771.
Ludwig et al., "Analysis of the SlyA-Controlled Expression, Subcellular Localization and Pore-Forming Activity of a 34 kDa Haemolysin (ClyA) from *Escherichia coli* K-12," Molecular Microbiology, vol. 31, No. 2, 1999, pp. 557-567.
Maglia et al., "Engineering a Biomimetic Biological Nanopore to Selectively Capture Folded Target Proteins," Biophysical Journal, vol. 104, No. 2, Feb. 5, 2013, p. 518a.
Makaram et al., "Trends in Nanomaterial-Based Non-Invasive Diabetes Sensing Technologies," Diagnostics, vol. 4, Apr. 21, 2014, pp. 27-46.

Mikheyev et al., "A First Look at the Oxford Nanopore MinION Sequencer," Molecular Ecology Resources, vol. 14, 2014, pp. 1097-1102.
Miles et al., "The Staphylococcal Leukocidin Bicomponent Toxin Forms Large Ionic Channels," Biochemistry, vol. 40, Jun. 28, 2001, pp. 8514-8522.
Miyazaki, "MEGAWHOP Cloning: A Method of Creating Random Mutagenesis Libraries via Megaprimer PCR of Whole Plasmids," Methods in Enzymology, vol. 498, 2011, pp. 399-406.
Movileanu et al., "Detecting Protein Analytes that Modulate Transmembrane Movement of a Polymer Chain Within a Single Protein Pore," Nature Biotechnology, vol. 18, Oct. 2000, pp. 1091-1095.
Moyer et al., "Correlation Between Sweat Glucose and Blood Glucose in Subjects With Diabetes," Diabetes Technology & Therapeutics, vol. 14, No. 5, 2012, pp. 398-402.
Mueller et al., "The Structure of a Cytolytic α-Helical Toxin Pore Reveals its Assembly Mechanism," Nature, vol. 459, Jun. 4, 2009, pp. 726-731.
Niedzwiecki et al., "Inspection of the Engineered FhuA ΔC/Δ4L Protein Nanopore by Polymer Exclusion," Biophysical Journal, vol. 103, Nov. 2012, pp. 2115-2124.
Nikolaidou et al., "α-Ketoglutarate: Biological Effects of a Novel Biomarker of Heart Failure," Heart, vol. 96, No. 17, Sep. 2010, 2 Pages.
Ogasawara et al., "Determination of Reduced Nicotinamide Adenine Dinucleotide Phosphate Concentration Using High-Performance Liquid Chromatography With Fluorescence Detection: Ratio of the Reduced Form as a Biomarker of Oxidative Stress," Biol. Pharm. Bull., vol. 32, No. 11, Nov. 2009, pp. 1819-1823.
Oukhaled et al., "Dynamics of Completely Unfolded and Native Proteins through Solid-State Nanopores as a Function of Electric Driving Force," American Chemical Society, vol. 5, No. 5, Apr. 8, 2011, pp. 3628-3638.
Plesa et al., "Fast Translocation of Proteins through Solid State Nanopores," Nano Letters, vol. 13, Jan. 23, 2013, pp. 658-663.
Quick et al., "A Reference Bacterial Genome Dataset Generated on the MinION Portable Single-Molecule Nanopore Sequencer," GigaScience, vol. 3, No. 22, 2014, pp. 1-6.
Rajagopalan et al., "Interaction of Dihydrofolate Reductase with Methotrexate: Ensemble and Single-Molecule Kinetics," PNAS, vol. 99, No. 21, Oct. 15, 2002, pp. 13481-13486.
Rodriguez-Gallego et al., "Mapping of the Circulating Metabolome Reveals α-Ketoglutarate as a Predictor of Morbid Obesity-Associated Non-Alcoholic Fatty Liver Disease," International Journal of Obesity, vol. 39, 2015, pp. 279-287.
Sanchez-Quesada et al., "Cyclic Peptides as Molecular Adapters for a Pore-Forming Protein," Journal of the American Chemical Society, vol. 122, No. 48, Dec. 6, 2000, pp. 11757-11766.
Soskine et al., "An Engineered ClyA Nanopore Detects Folded Target Proteins by Selective External Association and Pore Entry," Nano Letters, vol. 12, 2012, pp. 4895-4900.
Soskine et al., "Tuning the Size and Properties of ClyA Nanopores Assisted by Directed Evolution," Journal of the American Chemical Society, vol. 135, 2013, pp. 13456-13463.
Soskine et al., "Single-Molecule Analyte Recognition with ClyA Nanopores Equipped with Internal Protein Adaptors," Journal of the American Chemical Society, vol. 137, 2015, pp. 5793-5797.
Trewick et al., "Oxidative Demethylation by *Escherichia coli* AlkB Directly Reverts DNA Base Damage," Nature, vol. 419, Sep. 12, 2002, pp. 174-178.
Van Meervelt et al., "Detection of Two Isomeric Binding Configurations in a Protein-Aptamer Complex with a Biological Nanopore," American Chemistry Society, vol. 8, No. 12, Dec. 10, 2014, pp. 12826-12835.
Welford et al., "The Selectivity and Inhibition of AlkB," Journal of Biological Chemistry, vol. 278, No. 12, Mar. 21, 2003, pp. 10157-10161.
White et al., "Single Ion-Channel Recordings Using Glass Nanopore Membranes," J. AM. Chem. Soc., vol. 129, 2007, pp. 11766-11775.
Yoo et al., "Glucose Biosensors: An Overview of Use in Clinical Practice," Sensors, vol. 10, May 4, 2010, pp. 4558-4576.

(56) References Cited

OTHER PUBLICATIONS

Zhou et al., "Ion Channel Probes for Scanning Ion Conductance Microscopy," Langmuir, vol. 30, Nov. 25, 2014, pp. 15351-15355.
Ergel et al., "Protein Dynamics Control the Progression and Efficiency of the Catalytic Reaction Cycle of the *Escherichia coli* DNA-Repair Enzyme AlkB," Journal of Biological Chemistry, vol. 289, No. 43, Oct. 24, 2014, pp. 29584-29601.
Office Action from corresponding CN Application No. 201680034399.2, dated Dec. 11, 2019.
Chinese Office Action from CN Application No. 201680034399.2, dated Jan. 28, 2019.
European Office Action from EP Application No. 16719292.1, dated Mar. 13, 2019.
Krylova et al., "DNA Aptamers for as Analytical Tools for the Quantitative Analysis of DNA-Dealkylating Enzymes," Analytical Biochemistry, vol. 414, 2011, pp. 261-265.
Wendell et al., "Translocation of Double-Stranded DNA Through Membrane-Adapted Phi29 Motor Protein Nanopores," Nature Nanotechnology, vol. 4, Nov. 2009, pp. 765-772.
[No Author Listed] EBI Accession No. GSP:AXX09397. May 13, 2010.
[No Author Listed] EBI Accession No. A0A085GH19. Oct. 29, 2014.
[No Author Listed] EBI Accession No. A0A0D1LDB9. Apr. 29, 2015.
[No Author Listed] EBI Accession No. EMBLCDS:ABV05494. Sep. 11, 2007.
[No Author Listed] Helicos BioSciences Corporation, "Helicos Genetic Analysis System," Specification Sheet retrieved online at: www.helicosbio.com/Portals/0/Documents/Helicos_SalesSpec.pdf, 4 pages (2008).
[No Author Listed] Uniprot Accession No. A0A081NL13. Oct. 29, 2014. 4 pages.
[No Author Listed] Uniprot Accession No. A0A0P7DN88. Jan. 20, 2016. 4 pages.
[No Author Listed] Uniprot Accession No. Q8Z727. Oct. 24, 2003. 6 pages.
Ahern, Biochemical, reagents kits offer scientists good return on investment. The Scientist. Jul. 24, 1995;9(15):20.
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Aoki et al., Single channel properties of lysenin measured in artificial lipid bilayers and their applications to biomolecule detection. Proc Jpn Acad Ser B Phys Biol Sci. 2010;86(9):920-5.
Ashkenasy et al., Recognizing a single base in an individual DNA strand: a step toward DNA sequencing in nanopores. Angew Chem Int Ed Engl. Feb. 18, 2005;44(9):1401-4.
Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Avrameas, Coupling of enzymes to proteins with glutaraldehyde. Use of the conjugates for the detection of antigens and antibodies. Immunochemistry. Jan. 1969;6(1):43-52.
Bayley et al., Stochastic sensors inspired by biology. Nature. Sep. 13, 2001;413(6852):226-30.
Bayley et al., Wrestling with native chemical ligation. ACS Chem Biol. Dec. 18, 2009;4(12):983-5. doi: 10.1021/cb900304p.
Bayley, Membrane-protein structure: Piercing insights. Nature. Jun. 4, 2009;459(7247):651-2. doi: 10.1038/459651a.
Bayley, Sequencing single molecules of DNA. Curr Opin Chem Biol. Dec. 2006;10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Bianco et al., Helicase unwinding: active or merely perfect? J Mol Biol. Jul. 13, 2012;420(3):139-40. doi: 10.1016/j.jmb.2012.04.030. Epub May 2, 2012.
Bourdon et al., Molecular cloning and sequence analysis of a chondroitin sulfate proteoglycan cDNA. Proc Natl Acad Sci U S A. Mar. 1985;82(5):1321-5.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.
Cao et al., Structure of the nonameric bacterial amyloid secretion channel. Proc Natl Acad Sci U S A. Dec. 16, 2014;111(50):E5439-44. doi: 10.1073/pnas.1411942111. Epub Dec. 1, 2014.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.

(56) References Cited

OTHER PUBLICATIONS

Derrington et al., A Novel DNA Sensing Technique Using Nanopore MSPA. 54th Annual Meeting of the Biophysical Society, Poster 2182-Plat, 2 pages. (2010).
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
Engelhardt et al., A tetrameric porin limits the cell wall permeability of *Mycobacterium smegmatis*. J Biol Chem. Oct. 4, 2002;277(40):37567-72. Epub Jul. 18, 2002.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.
Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.
Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.
Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.
Goyal et al., Structural and mechanistic insights into the bacterial amyloid secretion channel CsgG. Nature. Dec. 11, 2014;516(7530):250-3. doi: 10.1038/nature13768. Epub Sep. 14, 2014.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Interaction of the noncovalent molecular adapter, beta-cyclodextrin, with the staphylococcal alpha-hemolysin pore. Biophys J. Oct. 2000;79(4):1967-75.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Guan et al., Stochastic sensing of TNT with a genetically engineered pore. Chembiochem. Oct. 2005;6(10):1875-81.
Guasch et al., Detailed architecture of a DNA translocating machine: the high-resolution structure of the bacteriophage phi29 connector particle. J Mol Biol. Jan. 25, 2002;315(4):663-76.
Hall et al., Hybrid pore formation by directed insertion of ?-haemolysin into solid-state nanopores. Nat Nanotechnol. Dec. 2010;5(12):874-7. doi: 10.1038/nnano.2010.237. Epub Nov. 28, 2010.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Haque et al., Solid-State and Biological Nanopore for Real-Time Sensing of Single Chemical and Sequencing of DNA. Nano Today. Feb. 2013;8(1):56-74.
He et al. 2012; The T4 phage SF1 B helicase dda is structurally optimized to perform DNA strand separation. Structure. 20:1189-1200.
Henrickson et al., Driven DNA transport into an asymmetric nanometer-scale pore. Phys Rev Lett. Oct. 2, 2000;85(14):3057-60.
Heron et al., Direct detection of membrane channels from gels using water-in-oil droplet bilayers. J Am Chem Soc. Dec. 26, 2007;129(51):16042-7. Epub Dec. 1, 2007.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{1, pt. 2):508a, No. 2482-Plat (2002).
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Nanopores as protein sensors. Nat Biotechnol. Jun. 7, 2012;30(6):506-7. doi: 10.1038/nbt.2264.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.
Hwang et al., Electrical behavior of droplet interface bilayer networks: experimental analysis and modeling. J Am Chem Soc. Sep. 26, 2007;129(38):11854-64. Epub Sep. 1, 2007 Sep 1.
Iacovache et al., Structure and assembly of pore-forming proteins. Curr Opin Struct Biol. Apr. 2010;20(2):241-6. doi:10.1016/j.sbi.2010.01.013. Epub Feb. 19, 2010.
Ide et al., Lysenin forms a voltage-dependent channel in artificial lipid bilayer membranes. Biochem Biophys Res Commun. Jul. 21, 2006;346(1):288-92. Epub May 26, 2006.
Ivanov et al., DNA tunneling detector embedded in a nanopore. Nano Lett. Jan. 12, 2011;11(1):279-85. doi: 10.1021/nl103873a. Epub Dec. 6, 2010.
Jayasinghe et al., The leukocidin pore: evidence for an octamer with four LukF subunits and four LukS subunits alternating around a central axis. Protein Sci. Oct. 2005;14(10):2550-61.
Johnston et al., Coexpression of proteins in bacteria using T7-based expression plasmids: expression of heteromeric cell-cycle and transcriptional regulatory complexes. Protein Expr Purif. Dec. 2000;20(3):435-43.

(56) References Cited

OTHER PUBLICATIONS

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Khulbe et al., DNA translocation through a-hemolysin nanopores with potential application to macromolecular data storage. Journal Applied Physics, vol. 97(104317):1-7 (2005).
Kobayashi et al., Comparative Physiology and Biochemistry, 2005, vol. 22, No. 3-4, pp. 139-148.
Kumar et al., PEG-labeled nucleotides and nanopore detection for single molecule DNA sequencing by synthesis. Sci Rep. 2012;2:684. Epub Sep. 21, 2012.
Langecker et al., Synthetic lipid membrane channels formed by designed DNA nanostructures. Science. Nov. 16, 2012;338(6109):932-6. doi: 10.1126/science.1225624.
Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.
Li et al., DNA molecules and configurations in a solid-state nanopore microscope. Nat Mater. Sep. 2003;2(9):611-5. Epub Aug. 24, 2003.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Lu et al., Protein Motion and Configurations in a Form-Fitting Nanopore: Avidin in ClyA. Biophys J. Sep. 4, 2018; 115(5): 801-808. Epub Aug. 4, 2018. doi: 10.1016/j.bpj.2018.07.024.
Luo et al., Influence of polymer-pore interactions on translocation. Phys Rev Lett. Oct. 5, 2007;99(14):148102. Epub Oct. 1, 2007.
Maglia et al., DNA strands from denatured duplexes are translocated through engineered protein nanopores at alkaline pH. Nano Lett. Nov. 2009;9(11):3831-6. doi: 10.1021/nl9020232.
Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.
Manrao et al., Nucleotide Discrimination with DNA Immobilized in the MspA Nanopore. PLoS One, vol. 6(10):e25723, 7 pages (2011).
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Manrao et al., Single Nucleotide Discrimination in Single Stranded DNA Immobilized within Biological Nanopre MSPA. 54th Annual Meeting of the Biophysical Society, 3 pages (2010).
Martin et al., Nanoscale protein pores modified with PAMAM dendrimers. J Am Chem Soc. Aug. 8, 2007;129(31):9640-9. Epub Jul. 18, 2007.
Marziali et al., New DNA sequencing methods. Annu Rev Biomed Eng. 2001;3:195-223.
Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.
Matsuura et al., Real-time observation of a single DNA digestion by lambda exonuclease under a fluorescence microscope field. Nucleic Acids Res. Aug. 15, 2001;29(16):E79.
Meller et al., Rapid nanopore discrimination between single polynucleotide molecules. Proc Natl Acad Sci U S A. Feb. 1, 2000;97(3):1079-84.
Meller et al., Single molecule measurements of DNA transport through a nanopore. Electrophoresis. Aug. 2002;23(16):2583-91.
Meller, Dynamics of polynucleotide transport through nanometre-scale pores. Journal Physics: Condensed Matter, vol. 15:R581-R607 (2003).
Merzlyak et al., Conductance and ion selectivity of a mesoscopic protein nanopore probed with cysteine scanning mutagenesis. Biophys J. Nov. 2005;89(5):3059-70. Epub Aug. 5, 2005.
Mitchell et al., Chemical tags facilitate the sensing of individual DNA strands with nanopores. Angew Chem Int Ed Engl. 2008;47(30):5565-8. doi:10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Moreau et al., Coupling ion channels to receptors for biomolecule sensing. Nat Nanotechnol. Oct. 2008;3(10):620-5. doi: 10.1038/nnano.2008.242. Epub Sep. 7, 2008.
Movileanu et al., Location of a constriction in the lumen of a transmembrane pore by targeted covalent attachment of polymer molecules. J Gen Physiol. Mar. 2001;117(3):239-52.
Mueller et al., The Structure of Cytolytic alpha-Helical Toxin Pore Reveals its Assembly Mechanism. Nature. Jun. 4, 2009;459:Supplemental Information.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365- R1393 (2003).
Pavlenok et al., Hetero-oligomeric MspA pores in Mycobacterium smegmatis. FEMS Microbiol Lett. Apr. 2016;363(7). pii: fnw046. doi:10.1093/femsle/fnw046. Epub Feb. 23, 2016.
Pavlenok et al., MspA nanopores from subunit dimers. PLoS One. 2012;7(6):e38726. doi: 10.1371/journal.pone.0038726. Epub Jun. 18, 2012.
Pfeiffer et al., Bivalent cholesterol-based coupling of oligonucletides to lipid membrane assemblies. J Am Chem Soc. Aug. 25, 2004;126(33):10224-5.
Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.
Rasko et al., The pangenome structure of *Escherichia coli*: comparative genomic analysis of *E. coli* commensal and pathogenic isolates. J Bacteriol. Oct. 2008;190(20):6881-93. doi:10.1128/Jb.00619-08. Epub Aug. 1, 2008.
Rhee et al., Nanopore sequencing technology: research trends and applications. Trends Biotechnol. Dec. 2006;24(12):580-6. Epub Oct. 19, 2006.
Robinson et al., Secretion of curli fibre subunits is mediated by the outer membrane-localized CsgG protein. Mol Microbiol. Feb. 2006;59(3):870-81.
Rotem et al., Protein detection by nanopores equipped with aptamers. J Am Chem Soc. Feb. 8, 2012;134(5):2781-7. doi:10.1021/ja2105653. Epub Jan. 26, 2012.
Russo et al., Reversible permeabilization of plasma membranes with an engineered switchable pore. Nat Biotechnol. Mar. 1997;15(3):278-82.
Saariaho et al., Characteristics of MuA transposase-catalyzed processing of model transposon end DNA hairpin substrates. Nucleic Acids Res. Jun. 6, 2006;34(10):3139-49.
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Sauer-Budge et al., Unzipping kinetics of double-stranded DNA in a nanopore. Phys Rev Lett. Jun. 13, 2003;90(23):238101. Epub Jun. 9, 2003.
Smeets et al., Salt dependence of ion transport and DNA translocation through solid-state nanopores. Nano Lett. Jan. 2006;6(1):89-95.

(56) References Cited

OTHER PUBLICATIONS

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.

Sutherland et al., An analysis of mismatched duplex DNA unzipping through a bacterial nanopore. Biochem Cell Biol. Jun. 2004;82(3):407-12.

Taylor et al., Atomic resolution insights into curli fiber biogenesis. Structure. Sep. 7, 2011;19(9):1307-16. doi: 10.1016/j.str.2011.05. 015.

Van De Goor, Nanopore Detection: Threading DNA Through a Tiny Hole. PharmaGenomics, vol. 4 (3):28-30 (2004).

Van Gerven et al., Secretion and functional display of fusion proteins through the curli biogenesis pathway. Mol Microbiol. Mar. 2014;91(5):1022-35. doi:10.1111/mmi.12515. Epub Feb. 12, 2014.

Van Lengerich et al., Covalent attachment of lipid vesicles to a fluid-supported bilayer allows observation of DNA-mediated vesicle interactions. Langmuir. Jun. 1, 2010;26(11):866672. doi: 10.1021/la904822f.

Van Meervelt et al., Real-Time Conformational Changes and Controlled Orientation of Native Proteins Inside a Protein Nanoreactor. J Am Chem Soc. Dec. 27, 2017; 139(51): 18640-18646. EPub Dec. 5, 2017. doi: 10.1021/jacs.7b10106.

Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.

Wallace et al., *E. coli* hemolysin E (HlyE, ClyA, SheA): X-ray crystal structure of the toxin and observation of membrane pores by electron microscopy. Cell. Jan. 21, 2000;100(2):265-76.

Wang et al., Nanopores with a spark for single-molecule detection. Nat Biotechnol. Jul. 2001;19(7):622-3.

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wanunu, Nanopores: A journey towards DNA sequencing. Phys Life Rev. Jun. 2012;9(2):125-58. doi:10.1016/j.plrev.2012.05.010. Epub May 18, 2012.

Wolfe et al., Catalyzing the translocation of polypeptides through attractive interactions. J Am Chem Soc. Nov. 14, 2007;129(45):14034-41. Epub Oct. 19, 2007.

Wong et al., Polymer capture by electro-osmotic flow of oppositely charged nanopores. J Chem Phys. Apr. 28, 2007;126(16):164903.

Wu et al., Protein nanopores with covalently attached molecular adapters. J Am Chem Soc. Dec. 26, 2007;129(51):16142-8. Epub Nov. 30, 2007.

Zernia et al., Current Blockades of Proteins inside Nanopores for Real-Time Metabolome Analysis. ACScs Nano. Feb. 25, 2020; 14(2): 2296-2307. EPub Jan. 31, 2020. doi: 10.1021/acsnano. 9b09434.

U.S. Appl. No. 16/858,859, filed Apr. 27, 2020, Stoddart et al.

[No Author Listed] Enterobacteria phage vB_EcoM-ACG-C40, complete genome. Genbank Acc. No. NC 019399.1. 97 pages.

[No Author Listed], *Escherichia coli* HS curli production assembly/transport subunit. Accession No. ABV05494. Sep. 11, 2007. 2 pages.

Eifler et al., Cytotoxin ClyA from *Escherichia coli* assembles to a 13-meric pore independent of its redox-state. EMBO J. Jun. 7, 2006;25(11):2652-61. doi: 10.1038/sj.emboj.7601130. Epub May 11, 2006.

Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.

Mueller et al., RCSB Protein Data Bank No. 2WCD. Mar. 11, 2009. doi: 10.2210/pdb2WCD/pdb. 5 pages.

Office Action for Application No. CN 201680034399.2, dated Oct. 10, 2020.

Rucker et al., Recombinant ferritin: modulation of subunit stoichiometry in bacterial expression systems. Protein Eng. 1997;10(8):967-973. doi:10.1093/protein/10.8.967.

Skocaj et al., The sensing of membrane microdomains based on pore-forming toxins. Curr Med Chem. 2013;20(4):491-501.

Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano. 9b09434. 19 pages.

U.S. Appl. No. 17/108,536, filed Dec. 1, 2020, Bruce et al.

U.S. Appl. No. 17/075,017, filed Oct. 20, 2020, Jayasinghe et al.

Boersma et al., Continuous stochastic detection of amino acid enantiomers with a protein nanopore. Angew Chem Int Ed Engl. Sep. 17, 2012;51(38):9606-9. doi: 10.1002/anie.201205687. Epub Aug. 29, 2012.

Goedhart et al., Quantitative co-expression of proteins at the single cell level—application to a multimeric FRET sensor. PLoS One. 2011;6(11):e27321. doi: 10.1371/journal.pone.0027321. Epub Nov. 17, 2011.

Guo et al., Nanopore sensor for copper ion detection using a polyamine decorated β-cyclodextrin as the recognition element. RSC Adv. 2017;7:15315. doi: 10.1039/c7ra00454k. 6 pages.

Nivala et al., Unfoldase-mediated protein translocation through an α-hemolysin nanopore. Nat Biotechnol. Mar. 2013;31(3):247-50. doi: 10.1038/nbt.2503. Epub Feb. 3, 2013.

Wu et al., Single-molecule detection of nitrogen mustards by covalent reaction within a protein nanopore. J Am Chem Soc. May 28, 2008;130(21):6813-9. doi: 10.1021/ja8004607. Epub Apr. 30, 2008.

\* cited by examiner

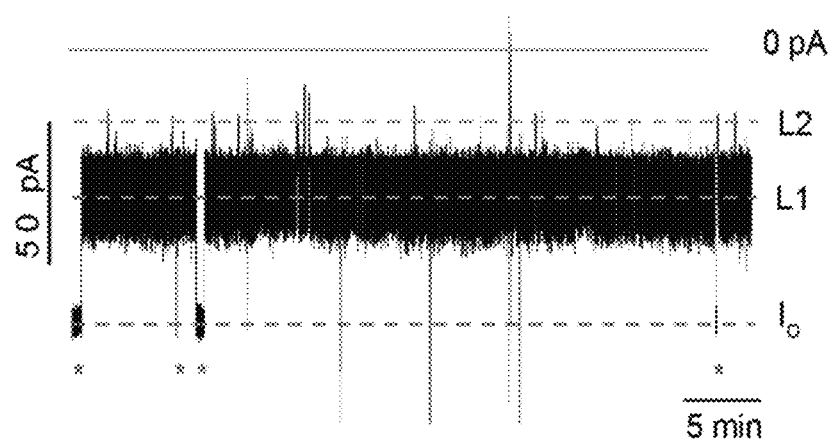
Figure 1C
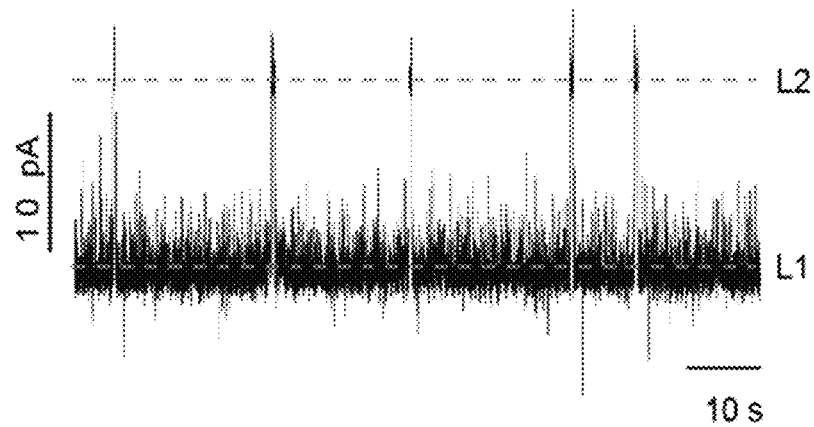

Figure 3A
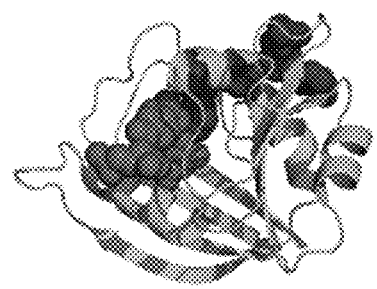
Figure 3B
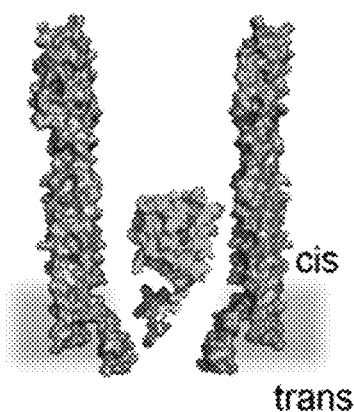
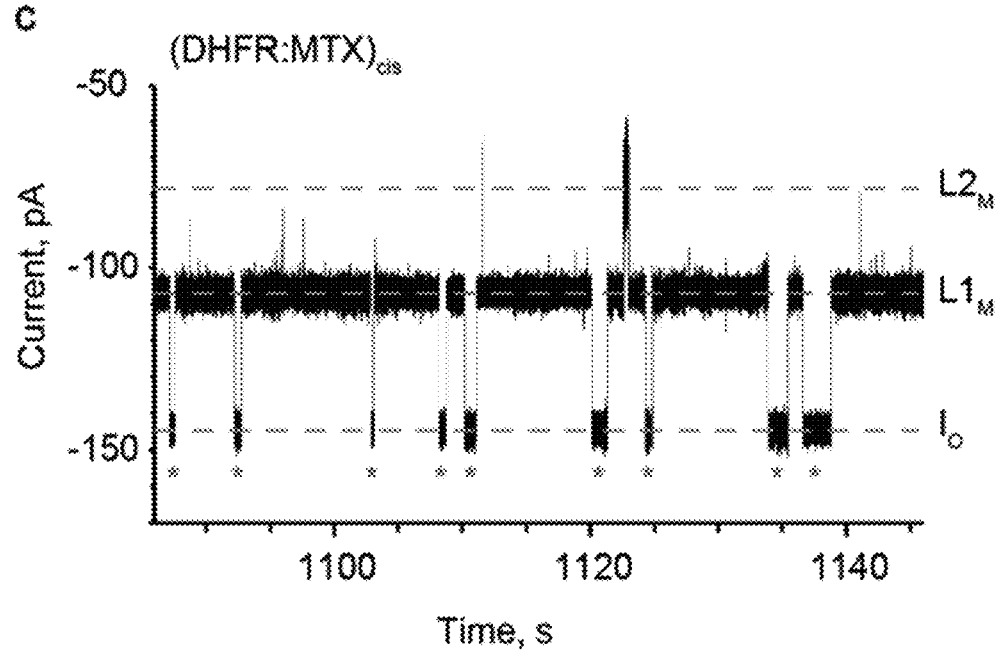
Figure 3C

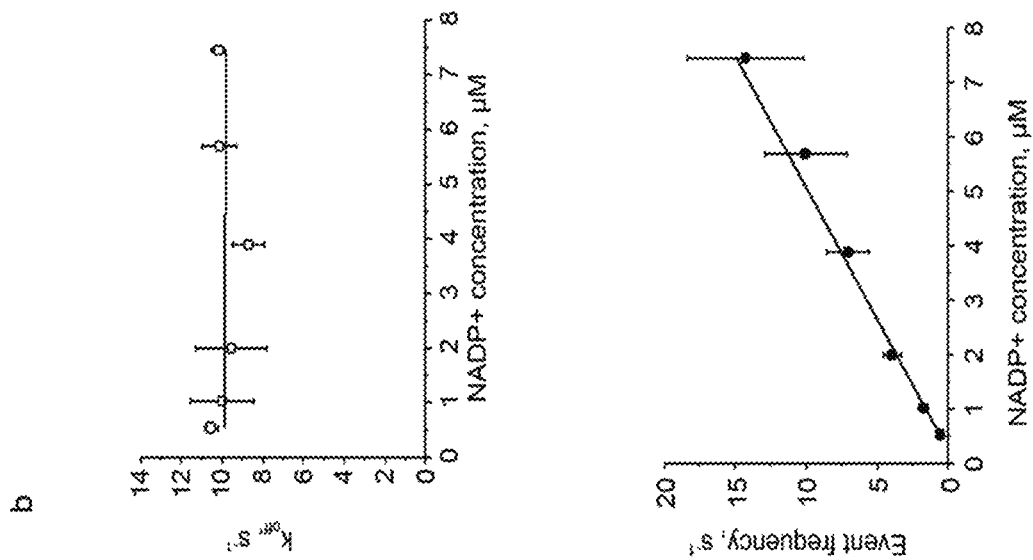
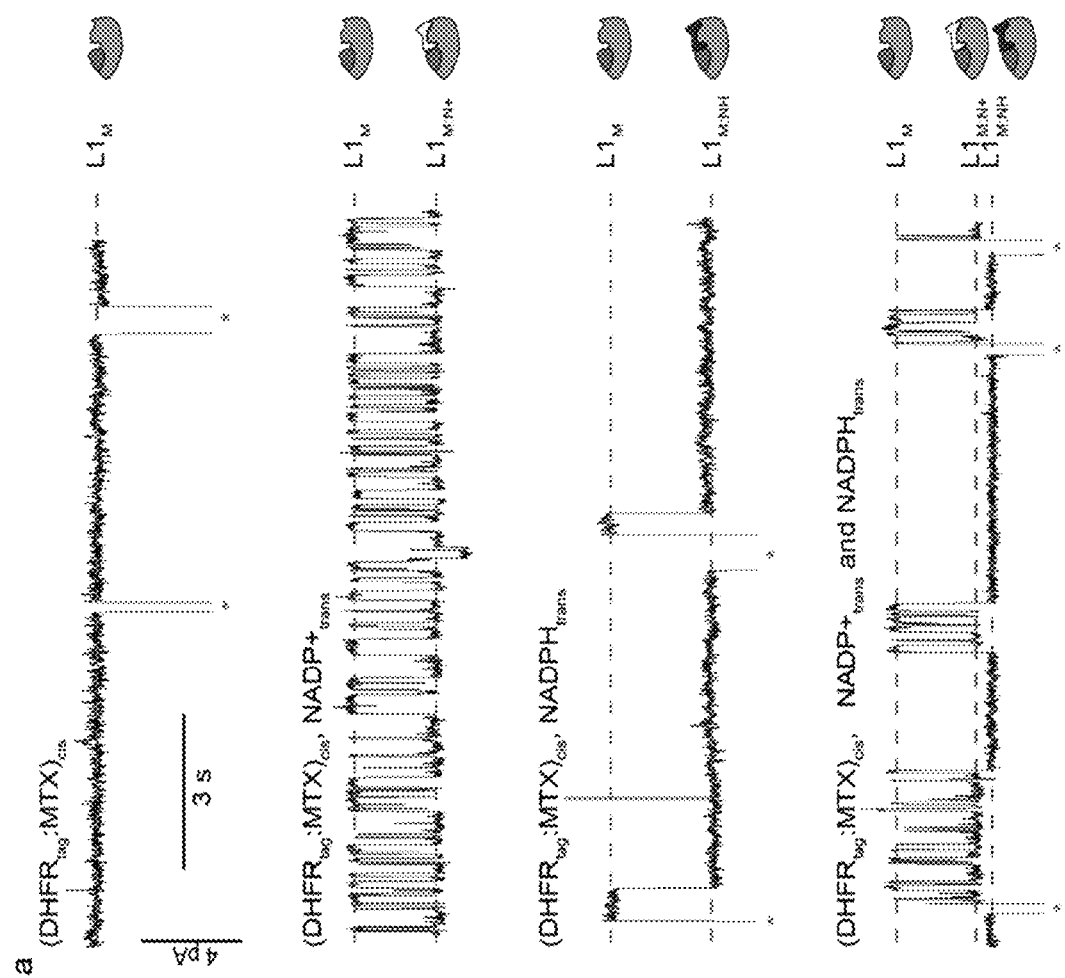
Figure 4A
Figure 4B

Figure 6B
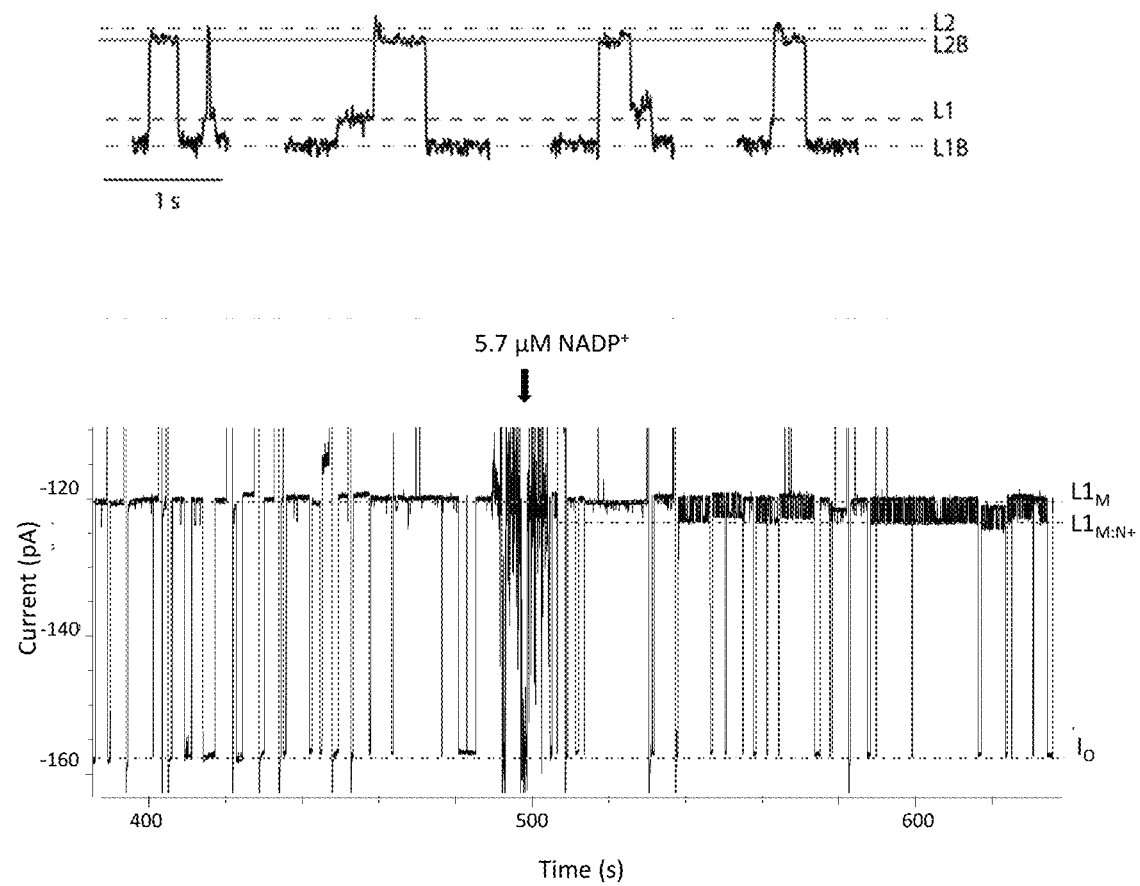
Figure 7
Figure 8

>DHFR10+ (SEQ ID NO:11)
```
          *  *..    *  _*    _     *      * *     * *      *** *
ERRGSSTRAKETAAAKFERQHMDSGSAKIAALKQKIAALKYKNAALKKKIAALKQGSAWSHPQF
_*
EK**
```

>DHFRtag (SEQ ID NO:12)
```
        *  ***     *              _*
ERRGSSTRAKKKIAALKQGSAWSHPQFEK**
```

>DHFR4+ (SEQ ID NO:13)
```
        *  **     *              _*
ERRGSSTRAKKIAALKQGSAWSHPQFEK**
```

>DHFR (SEQ ID NO:14)
```
        *              _*
ERRGSSTRAGSAWSHPQFEK**
```

NANOPORES WITH INTERNAL PROTEIN ADAPTORS

RELATED APPLICATIONS

This Application is a national stage filing under 35 U.S.C. 371 of International Patent Application Serial No. PCT/EP2016/058252, filed Apr. 14, 2016. Foreign priority benefits are claimed under 35 U.S.C. § 119(a)-(d) or 35 U.S.C. § 365(b) of British application number 1507264.8, filed Apr. 29, 2015 and British application number 1506307.6, filed Apr. 14, 2015. The entire contents of each of these applications are incorporated herein by reference.

REFERENCE TO SEQUENCE LISTING SUBMITTED VIA EFS-WEB

This application includes an electronically submitted sequence listing in .txt format. The .txt file contains a sequence listing entitled "19893-28 2018-04-16 Corrected Sequence Listing.txt" created on Apr. 16, 2018 and is 24 bytes in size. The sequence listing is being electronically submitted via EFS-Web on Apr. 16, 2018, and is hereby incorporated by reference herein in its entirety.

FIELD OF INVENTION

The present invention relates to nanopore sensors comprising nanopore proteins and protein adaptors internalized in the lumen of the nanopores. The protein adaptor retains both its binding specificity for specific substrates and its functional activity, so that the nanopore sensor may be used for detecting analytes and characterizing unique properties of bound analytes.

BACKGROUND

Over the past two decades nanopore analysis has emerged as a promising analytical tool for single-molecule analysis [Howorka, S. & Siwy, Z. (2009) Chem Soc Rev 38, 2360-2384; Bayley, H. (2015) Clin. chem. 61, 25-31; Luchian, T et al. (2003) Angew. Chem. 42, 3766-3771; Bezrukov, S. M. et al. (1994) Nature 370, 279-281]. Nanopore technology allows the investigation of native molecules with high sampling bandwidth without the need for labelling, chemical modifications or surface immobilisation. Further, the ionic current output signal can be easily interfaced with miniaturised and portable electronic devices. For instance, arrays of nanopores integrated into a MinION™ sequencer have been recently used for the profiling of genomic DNA [Ashton, P. M. et al. (2014) Nat. Biotechnol. 33, 296-300; Mikheyev, A. S. & Tin, M. M. (2014) Mol. ecol. res. 14, 1097-1102; Quick, J. et al. (2014) GigaScience 3, 22.]. Furthermore, biological nanopores have been reconstituted into bilayers formed on glass nanopipettes (White, R. J. et al (2007). J Am Chem Soc 129, 11766-11775) and on glass tips for scanning ion-conductance microscopy (Zhou, Y. et al (2014) Langmuir 30, 15351-15355). Therefore, nanopore-functionalized nanopipettes that can detect and quantify metabolites are promising platforms for measurement in single cells.

Previous studies showed that small molecules binding to cyclodextrin (Gu, L. Q. et al. (1999) Nature 398, 686-690) and cyclic peptide adaptors (Sanchez-Quesada, (2000) J. Am. Chem. Soc. 122, 11757-11766) or cucurbiturils carriers (Braha, O. et al. (2005) Chemphyschem, 6, 889-892). ("guest adaptors") could be detected by ionic current recordings using the α-hemolysin (αHL) nanopore. However, these guest adaptors and carriers do not bind selectively to host molecules, complicating the identification of specific analytes, especially in a complex mixture of compounds like a biological sample. Thus, there remains a need in the art for new nanopore sensors that confer highly-selective binding to target analytes.

It is well-known that proteins bind selectively to targets, and a further study demonstrated that electroosmotic and electrophoretic forces allow small proteins such as thrombin to become trapped inside nanopores [Soskine, M. et al. (2013) J Am Chem Soc, 135, 13456-13463; Soskine, M. (2012) Nano Lett. 12, 4895-4900], suggesting that proteins might be used as adaptors inside nanopores. However, building such hybrid devices is challenging. Most proteins are too large to be incorporated into the αHL and other biological nanopores [Jung, Y. et al. (2005) Biochem. 44, 8919-8929; Movileanu, L. (2000) Nat. Biotechnol. 18, 1091-1095. Fahie, M. et al. (2015) ACS nano, 9, 1089-1098] and translocate through solid-state nanopores too fast to be properly sampled (Plesa, C. et al. (2013) Nano Lett., 13, 658-663). Moreover, analysis in solid-state nanopores indicates that proteins would not be expected to retain their structure or function in the lumen of a nanopore. In solid-state nanopores, proteins are stretched by an electrical field (Oukhaled, A. et al. (2011) ACS nano 5, 3628-3638) and unfolded under applied potentials higher than +200 mV (Freedman, K. J. (2013). J. Scientific reports 3, 1638). If proteins are stretched or unfolded, their target binding sites and function are likely lost.

SUMMARY OF INVENTION

Described herein is a nanopore sensor based on a nanopore and a protein adaptor that is internalized in the lumen of the nanopore. Different types of proteins, including enzymes, can be used. The protein adaptor remains in the lumen of the nanopore without the use of covalent chemistry or other immobilization techniques, and surprisingly, the protein adaptor retains its folded structure, function and/or binding properties. The binding of analytes to the internalized protein adaptor is reflected by changes in the nanopore conductance. Accordingly, methods for detecting analytes using the sensor are also described, and uses of the sensor in the discovery of new therapeutics and the detection of biomarker analytes in biological samples is disclosed.

A first aspect of the present invention relates to a nanopore sensor comprising a nanopore and a protein adaptor internalized in the lumen of the nanopore, wherein the protein adaptor is a functional enzyme or ligand-binding protein.

In some embodiments, a first opening in the nanopore has a wider diameter than a second opening in the nanopore.

In certain embodiments, the nanopore sensor is cytolysin A (ClyA) or a mutant or variant thereof.

In some embodiments, the protein adaptor is globular. The protein adaptor may be a functional enzyme selected from a demethylase and a reductase. In certain embodiments, the protein adaptor comprises a tag. The tag may have a net overall positive or negative charge.

In certain embodiments, the protein adaptor forms a complex with one or more additional molecules. In some embodiments, the protein adaptor binds to a target analyte. The target analyte may be selected from a small molecule analyte, a protein analyte, and a nucleic acid analyte. In some embodiments, the target analyte is charged.

In some embodiments, the nanopore sensor is ClyA, and comprises a plurality of subunits, each subunit comprising an amino acid sequence represented by SEQ ID NO:3.

In certain embodiments, the nanopore sensor is a demethylase, for example, AlkB demethylase. In certain embodiments, the nanopore sensor is a reductase, for example, dihydrofolate reductase. In a specific embodiment the demethylase is AlkB demethylase comprising an Asn120Asp mutation.

Another aspect of the present invention relates to methods for detecting an analyte in a sample, comprising the steps of:
a) obtaining a nanopore sensor comprising a nanopore and a protein adaptor internalized in the lumen of the nanopore, wherein the protein adaptor is a functional enzyme or ligand-binding protein.
b) adding a sample comprising an analyte to the cis side or the trans side of the nanopore, and
c) measuring conductance across the nanopore, wherein a change in conductance after addition of the sample indicates the binding of the analyte to the protein adaptor and the presence of the analyte in the sample.

The present invention thus discloses a method for detecting an analyte in a sample, comprising (a) obtaining a nanopore sensor comprising a nanopore and a protein adaptor internalized in the lumen of the nanopore, (b) adding the sample to the cis side or the trans side of the nanopore, and (c) measuring conductance across the nanopore, wherein a change in conductance after adding the sample indicates the analyte is present in the sample and has bound to the protein adaptor.

The present invention thus discloses a method for identifying a ligand for a protein adaptor, comprising (a) obtaining a nanopore sensor comprising a nanopore and a protein adaptor internalized in the lumen of the nanopore, (b) adding a test compound to the cis side or the trans side of the nanopore, and (c) measuring the conductance across the nanopore, wherein a change in conductance after adding the test compound indicates that the test compound is a ligand that binds to the protein adaptor.

Herein the nanopore has a first and a second opening whereby the first opening has a wider diameter than the second opening.

In specific embodiments, the nanopore is cytolysin A (ClyA) or a mutant or variant thereof such as cytolysin A (ClyA) mutant Gln56Trp.

In specific embodiments, ClyA comprises a plurality of subunits, each subunit comprising an amino acid sequence represented by SEQ ID NO:3.

In specific embodiments, the protein adaptor is globular.

In specific embodiments, wherein the protein adaptor is a demethylase enzyme or a reductase enzyme, such as AlkB demethylase (for example AlkB demethylase comprising an Asn120Asp mutation) or dihydrofolate reductase.

In specific embodiments the protein adaptor comprises a tag, which may have a net overall positive or negative charge.

In specific embodiments wherein the protein adaptor forms a complex with one or more additional molecules.

In specific embodiments the analyte is a small molecule, a protein, or a nucleic acid.

In specific embodiments the analyte is charged.

Another aspect of the present invention is the use of a nanopore sensor as described above the detection of an analyte in a sample.

In specific embodiments the analyte is a small molecule, a protein, or a nucleic acid.

In specific embodiments, the analyte is charged.

BRIEF DESCRIPTION OF DRAWINGS

FIGS. 1a-1c show internalization of AlkB-$Fe^{++}$ into ClyA-AS. FIG. 1a shows a cartoon representation of *E. coli* AlkB (green) containing a metal ion ($Co^{2+}$, sphere) and binding to the cofactor (2-OG, labeled). The DNA binding site is depicted by an orange line. PDB_ID 3KHB. FIG. 1b shows the representation of a single AlkB-$Fe^{++}$ enzyme confined in a ClyA-AS nanopore (shown as cross-section) embedded in a planar lipid bilayer (labeled) under a negative applied potential. The dimensions of the pore consider the Van der Waals radii of the atoms. FIG. 1c, (top panel) shows typical current blockades provoked by AlkB-$Fe^{++}$ molecules (~4 nM, cis) entering a ClyA-AS nanopore at −60 mV. The open pore current ($I_O$) is represented by a blue dashed line, while Level 1 and Level 2 are shown by dashed lines, respectively. The asterisks represent the restoration of Jo upon the exiting of AlkB-$Fe^{++}$ from the pore. The bottom panel shows the detail of a single AlkB-$Fe^{++}$ blockade, showing Level 1 and Level 2 current levels. The current traces were collected by applying a Bessel-low pass filter with a 2 kHz cut-off and sampled at 10 kHz. An additional Bessel 8-pole filter with 50 Hz cut-off was digitally applied to the traces shown in FIG. 1c (bottom panel). All recordings were carried out in 150 mM NaCl, 15 mM Tris HCl pH 8.0, at 28° C., and the AlkB was added to the cis compartment.

FIGS. 2a-2b show binding of ligands to AlkB-$Fe^{++}$ confined inside ClyA-AS. FIG. 2a shows a typical ligand-induced blockades to individual AlkB-$Fe^{++}$ enzymes confined inside ClyA-AS at −60 mV. The ligand used is shown on the right of the trace. The bound Level 1 current levels ($L_{1O}$, $L_{1N}$, $L_{1S}$) are represented by the lowermost dashed lines. The substrate concentration was 0.6 mM for 2-OG, 0.6 mM for N-OG and 2 mM for SUC binding to wild type AlkB-$Fe^{++}$, and 7.2 mM for 2-OG binding to N120D-AlkB-$Fe^{++}$. FIG. 1b (left panel) shows dissociation rate constants ($k_{off}$) as a function of the ligand concentration at −60 mV; while FIG. 2b (right panel) shows Event frequency ($1/\tau_{on}$) as a function of the ligand concentration at −60 mV. 2-OG is shown in squares, SUC in circles and N-OG in triangles. All values for $k_{off}$ and f are based on >350 binding events in total collected from N>3 single channel experiments with each experiment typically analysing n>8 AlkB blockades. All current traces were collected by applying a Bessel-low pass filter with a 2 kHz cut-off and sampled at 10 kHz. An additional Bessel 8-pole filter with 50 Hz cut-off was digitally applied to the current traces. All recordings were carried out in 150 mM NaCl, 15 mM Tris HCl pH 8.0, at 28° C., and the ligands were added to the cis compartment. Errors are given as standard deviations.

FIGS. 3a-3c show DHFR as a protein adaptor. FIG. 3a is a cartoon representation of *E. coli* DHFR (labeled) with bound methotrexate (MTX, spheres) and NADPH (spheres), PDB_ID 1RH3. FIG. 3b shows a representation of a single $DHFR_{tag}$ enzyme in complex with MTX confined in a ClyA-AS nanopore (shown as cross-section) embedded in a planar lipid bilayer (labeled) under a negative applied potential. The positively charged polypeptide tag added at the C-terminus of DHFR is labeled. FIG. 3c shows typical current blockades provoked by the capture of $DHFR_{tag}$: MTX complexes (20 nM $DHFR_{tag}$, 400 nM MTX, cis) by the ClyA-AS nanopore at −90 mV. The open pore current ($I_O$) is represented by the lowermost dashed line, while $L_{1m}$ and $L_{2M}$ are shown by the middle and uppermost dashed lines, respectively. Asterisks represent restoration of Jo upon the exiting of $DHFR_{tag}$:MTX from the pore. The current traces were collected in 150 mM NaCl, 15 mM Tris HCl pH 7.5, at 28° C. by applying a Bessel-low pass filter with a 2 kHz cut-off and sampled at 10 kHz.

FIGS. 4a-4b show current enhancements upon ligand binding to DHFR$_{tag}$. FIG. 4a shows ligand-induced current enhancements to individual DHFR$_{tag}$:MTX blockades at −90 mV. NADP+ and NADPH were added to the trans compartment after addition of 20 nM DHFR$_{tag}$ and 400 nM MTX to the cis compartment. From top to bottom: no ligand; 5.7 μM of NADP+; 0.7 μM of NADPH; 7.4 μM of NADP+ together with 0.7 of NADPH. Free and bound Level 1 (L1 and L1o) are shown by dashed lines. Asterisks represent restoration of I$_O$ upon the exit of DHFR$_{tag}$:MTX from the pore. On the right of the current traces is the schematic representation of the interaction of DHFR$_{tag}$ with MTX, NADP+ or NADPH. FIG. 4b (top panel) shows dissociation rate constants (k$_{off}$) as a function of the NADP+ concentration added to the trans compartment at −90 mV. FIG. 4b (bottom panel) shows event frequency (1/τ$_{on}$) as a function of the NADP+ concentration added to the trans compartment at −90 mV. Errors are shown as standard deviations. All values for k$_{off}$ and f are based on >2000 binding events in total collected from N>8 single channel experiments with each experiment typically analysing n>20 DHFR$_{tag}$:MTX blockades. All current traces were collected by applying a Bessel-low pass filter with a 2 kHz cut-off and sampled at 10 kHz. An additional Bessel 8-pole filter with 50 Hz cut-off was digitally applied to the traces shown in FIG. 4a. All recordings were carried out in 150 mM NaCl, 15 mM Tris HCl pH 7.5, at 28° C.

FIGS. 6a-6b show 2-OG induced current levels to AlkB-Fe$^{++}$. FIG. 6a shows an extended current trace showing L1, L1B, L2 and L2B current levels induced by the binding of 2-OG to a single confined AlkB-Fe$^{++}$. In FIG. 6b are selected traces showing the details of the ligand-induced current levels. Transitions were always from L1B to L2B or from L1 to L2, or from L2 to L1 or from L2B to L1B. Current traces were recorded in presence of 4.8 mM 2-OG at −60 mV applied potential in 150 mM NaCl, 15 mM Tris.HCl pH 8.0 at 28° C. using 2 kHz filtering and 10 kHz sampling rate, and filtered digitally with a Bessel (8-pole) low-pass filter with 50 Hz cut-off.

FIG. 7 shows NADP+ induced binding events to DHFR$_{tag}$:MTX. The current trace shows DHFR$_{tag}$:MTX (added to the cis compartment, 50 nM of DHFR$_{tag}$ and 400 nM MTX) blockades before (left) and after (right) the addition of 5.7 μM NADP+ (arrow) to the trans compartment. The binding of NADP+ results in reversible current enhancements from L1$_M$ (uppermost dashed line) to L1$_{M:N+}$ (labeled). The grey dashed line (lowermost dashed line) corresponds to the open pore current (I$_o$). The trace was recorded at −90 mV applied potential in 150 mM NaCl, 15 mM Tris.HCl pH 7.5 at 28° C. using 2 kHz filtering and 10 kHz sampling rate, and filtered digitally with a Bessel (8-pole) low-pass filter with 50 Hz cut-off.

FIG. 8 shows the effect of the cognate Anti-AlkB aptamer on the AlkB-Fe$^{++}$-induced current blockades. The addition of 40 μM cognate aptamer (TGCCTAGCGTTTCAT-TGTCCCTTCTTATTAGGTGATAATA, SEQ ID NO: 27, Table 5) reduced the frequency of the AlkB-Fe$^{++}$ blockades to ClyA-AS caused by 21 nM AlkB_Fe$^{++}$ due to electrostatic repulsion and/or steric hindrance between the AlkB:aptamer complexes and the negatively charged ClyA-AS lumen (Soskine, M. (2012) Nano Lett. 12, 4895-4900). The recordings were carried out in 150 mM NaCl, 15 mM Tris HCl pH 8.0 at 28° C. and −35 mV applied potential.

In FIGS. 9a and 9b, the current traces show the capture of DHFR$_{tag}$:MTX inside ClyA-AS (50 nM of DHFR$_{tag}$ and 400 nM of MTX added to the cis compartment), after the addition of 0.74 μM NADPH to the trans compartment. The uppermost dashed line represents the DHFR$_{tag}$:MTX L1$_M$ level. The asterisks indicate "short" (i.e. low affinity) NADPH binding events, while the solid lines indicate "long" (i.e. high affinity) NADPH induced binding events. The arrows show the capture of a new DHFR$_{tag}$:MTX complex. The current trace in (a) shows DHFR$_{tag}$:MTX blockades displaying either "short" or "long" NADPH binding events. The current trace in (b) shows the switching between "short" and "long" binding modes within the same DHFR$_{tag}$:MTX blockade. FIGS. 9c and 9d show DHFR$_{tag}$:MTX blockades (50 nM DHFR$_{tag}$ and 400 nM MTX in cis) after the addition of 5.7 μM NADP+ in trans. The dashed line represents the DHFR$_{tag}$:MTX L1M level, the non-responsive state of the binary complex towards NADP+ is indicated by a solid line. The arrows indicate the capture of a new DHFR$_{tag}$:MTX complex. The current trace in (c) shows DHFR$_{tag}$:MTX blockades that are either responsive or non-responsive towards NADP+ addition. The current trace in (d) shows the switching between non-responsive and responsive states within the same DHFR$_{tag}$:MTX blockade. The traces were recorded at −90 mV applied potential in 150 mM NaCl, 15 mM Tris.HCl pH 7.5 at 28° C. using 2 kHz filtering and 10 kHz sampling rate, and filtered digitally with a Bessel (8-pole) low-pass filter with 50 Hz cut-off.

FIG. 11b: DHFR$_{10+}$, FIG. 11c: DHFR$_{4+}$, FIG. 11d: DHFR$_{tag}$ added to the cis compartment. Every set of three panels shows DHFR$_{n+}$ blockades recorded without ligands (left panel), after the addition of 400 nM MTX to the cis compartment (centre panel) and after further addition of 20 μM of NADPH in cis (a) or 0.7 μM of NADPH to the trans compartment (FIGS. 11b, 11c, 11d) (right panel). The arrows indicate NADPH binding events to the binary DHFR$_{10+}$:MTX complexes. The asterisks indicate the transition of DHFR$_{10+}$:MTX to a lower conductance level. Current traces were recorded at −90 mV applied potential in 150 mM NaCl, 15 mM Tris.HCl pH 7.5 at 28° C. using 2 kHz filtering and 10 kHz sampling rate, and filtered digitally with a Gaussian low-pass filter with 500 Hz cut-off.

DETAILED DESCRIPTION OF INVENTION

Figure 1A:
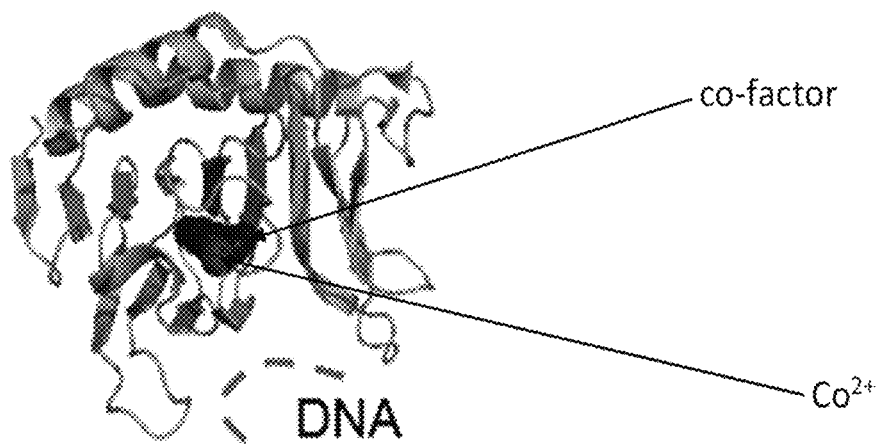

Proteins have evolved to identify their ligands with high specificity in a sea of very similar chemical species. Accordingly, a nanopore which has incorporated protein adaptors in the lumen of the nanopore is well-suited for use in detecting ligand analytes. When the internalized protein adaptor binds to its target analyte, the conformational change in the protein adaptor and/or presence of the target analyte bound to the protein adaptor is measured as a change in nanopore conductance, for example, as an increase in the ionic current blockade events in the nanopore.

Accordingly, one aspect of the present disclosure relates to nanopore sensors comprising a nanopore (also called "pore," "pore protein," or "nanopore protein") and a protein adaptor (or "adaptor" or "internalized protein" or "protein") which is fully or partially internalized (or "contained," "incorporated," "trapped," "set," "accommodated," "residing," "embedded," or "confined") within the lumen of the nanopore.

Nanopores

Exemplary nanopores include, but are not limited to cytolysins, hemolysins, porins, DNA packaging protein, and motor proteins. In some embodiments, the nanopore is Phi29 (Wendell, D. et al. (2009) *Nat. nanotech.* 4, 765-772), pneumolysin (Gilbert, R. J. et al. (1999) *Cell* 97, 647-655), FhuA (Niedzwiecki D J et al. (2012) *Biophys J.* 103, 2115-2124) or a solid-state nanopores.

In certain embodiments, the nanopore is a pore-forming cytotoxic protein, for example, a bacterial cytolysin. In certain embodiments, the nanopore is a cytolysin from a gram-negative bacteria such as *Salmonella* or *Escherichia coli* (*E. coli*). In some embodiments, the nanopore is Cytolysin A (ClyA) from *Salmonella typhi* (*S. typhi*) or *Salmonella paratyphi* (*S. paratyphi*). In some embodiments, the nanopore is a mutant or variant of ClyA, such as a modified variant of ClyA like ClyA-CS or ClyA-AS as described in WO2014153625.

In certain embodiments, the nanopore is cylindrically shaped with at least 2 openings, for example, a cis opening and a trans opening. A first opening may have a larger diameter than a second opening in the nanopore. In some embodiments, the cis opening has a larger diameter than the trans opening. Thus, the "cis diameter" is wider than the "trans diameter." Alternatively, the trans opening may have a larger diameter than the cis opening. Typically, a nanopore is an oligomeric structure comprising subunits (or "monomers"), and the size of the pore lumen depends on the number and/or composition of subunits in the oligomeric structure. In some embodiments, the nanopore may comprise at least 7 monomers, for example, 7, 8, 9, 10, 11, 12, 13, 14, 15, 16, 17, 18, 19, or 20 monomer subunits. In some embodiments, the nanopore comprises at least 20 monomer subunits, for example, 20-25, 25-30, 35-40, or 45-50 subunits. In certain embodiments, the nanopore comprises 12 subunits. In further embodiments, the nanopore comprises 13 subunits, or 14 subunits. The subunits may preferentially assemble in 12mers and/or 13mers, depending on the amino acid sequence of the subunits.

The nanopores comprise subunits which may be assembled into different oligomeric forms. Within a single nanopore (for example a ClyA nanopore), each of the subunits may be identical, or the subunits may be different, so that subunits in a pore may comprise sequences that differ from sequences of other polypeptide subunits in the same nanopore. In certain embodiments, nanopores as disclosed herein, such as ClyA nanopores or variants such as ClyA-CS and ClyA-AS, may form more than one subtype depending on subunit composition. For example, there may be at least 2 or 3 different subtypes of subunits in the nanopore, depending on the composition of the subunits. ClyA-AS [Mueller, M. et al. (2009) *Nature,* 459, 726-730; Soskine, M. et al. (2013) *J Am Chem Soc,* 135, 13456-13463] (SEQ ID NO:3) may be assembled into at least 3 oligomeric forms (Type I, Type II and Type III ClyA) (Soskine, M. et al. (2013) *J Am Chem Soc,* 135, 13456-13463) that are large enough to accommodate proteins or protein-DNA complexes (Van Meervelt, V. et al (2014) *ACS nano,* 8, 128262-12835). Any nanopore that is assembled from individual subunits may have different oligomeric forms, and the oligomeric forms may vary in properties such as size and voltage dependent opening and closing (gating) of the nanopore. Subtypes may be preferentially formed by subunits of a particular polypeptide sequence.

In some embodiments, the nanopore is ClyA from *Salmonella typhi* and comprises a plurality of subunits, wherein each subunit comprises a polypeptide represented by an amino acid sequence at least 80% identical to SEQ ID NO: 1. In certain embodiments, the subunits are represented by an amino acid sequence at least 85% identical, 90% identical, 95% identical, 99% identical or 100% identical to SEQ ID NO:1. Identical may refer to amino acid identity, or may refer to structural and/or functional identity. Accordingly, one or more amino acids may be substituted, deleted, and/or added, as compared with SEQ ID NO:1. Modifications may alter the pore lumen in order to alter the size, binding properties, and/or structure of the pore. Modifications may also alter the ClyA nanopore outside of the lumen.

In certain embodiments, the ClyA nanopore comprises a plurality of subunits, wherein each subunit comprises a polypeptide represented by an amino acid sequence of SEQ ID NO:1 (or a sequence that is at least 85%, 90%, 95%, 96%, 96%, 98%, or 99% identical to SEQ ID NO:1), and wherein exactly one Cys residue is substituted with Ser. The Cys residue may be Cys 87 and/or Cys 285 in SEQ ID NO:1. In some embodiments, the Cys residue is Cys285. The remaining amino acid residues may also be substituted, for example, with amino acids that share similar properties such as structure, charge, hydrophobicity, or hydrophilicity. In certain embodiments, substituted residues are one or more of L99, E103, F166, and K294. For example, the substituted residues may be one or more of L99Q, E103G, F166Y, and K294R. An exemplary subunit may comprise substitutions L99Q, E103G, F166Y, K294R, and C285S. Thus, each subunit may comprise a polypeptide represented by an amino acid sequence of SEQ ID NO:2. An exemplary ClyA nanopore comprising subunits in which exactly one Cys residue is substituted with Ser may be called ClyA-CS.

Other ClyA mutants of the present invention are variants with a mutation at Ser110, Lys125, Val67, Val60, Gln56 or Arg49. Specific embodiments of such variants are Lys125Trp, Val60Trp and Gln56Trp.

In some embodiments, the ClyA nanopore comprises a plurality of subunits, wherein each subunit comprises a polypeptide represented by an amino acid sequence of SEQ ID NO:1 (or a sequence that is at least 85%, 90%, 95%, 96%, 96%, 98%, or 99% identical to SEQ ID NO:1), and wherein exactly one Cys residue is substituted with Ala. The cysteine residue may be Cys 87 or Cys 285 in SEQ ID NO:1. In some embodiments, each subunit comprises a polypeptide represented by an amino acid sequence of SEQ ID NO:1 (or a sequence that is at least 85%, 90%, 95%, 96%, 96%, 98%, or 99% identical to SEQ ID NO:1), wherein one Cys residue is substituted with Ser and/or exactly one Cys residue is substituted with Ala. The cysteine residues may be Cys87 or Cys285 in SEQ ID NO:1. Other amino acid residues may be substituted, for example, with amino acids that share similar properties such as structure, charge, hydrophobicity, or hydrophilicity. In certain embodiments, substituted residues are one or more of L99, E103, F166, K294, L203 and H207. For example, the substituted residues may be L99Q, E103G, F166Y, K294R, L203V, and H207Y. An exemplary subunit may comprise L99Q, E103G, F166Y, K294R, L203V, and H207Y, and C285S. Accordingly, each subunit may comprise a polypeptide represented by an amino acid sequence of SEQ ID NO:3. An exemplary ClyA nanopore comprising subunits in which exactly one Cys residue is substituted with Ser and exactly one Cys residue is substituted with Ala may be called ClyA-AS.

The present disclosure further relates to nucleic acids encoding the modified ClyA nanopores. In some embodiments, a nucleic acid encoding a modified ClyA nanopore is represented by a nucleotide sequence that is at least 80%, 90%, 95%, 96%, 96%, 98%, or 99% identical to SEQ ID NO:4. A nucleic acid may be represented by SEQ ID NO: 5 or SEQ ID NO:6. Nucleotide sequences may be codon optimized for expression in suitable hosts, for example, *E. coli*.

In some embodiments, the lumen of the nanopore is large enough to accommodate a protein adaptor that is folded and is either (1) not bound or (2) bound to a target such as a specific target analyte. The protein adaptor may be complexed with one or more additional molecules such as a co-factor or substrate or inhibitor to form a protein adaptor complex (or "adaptor complex"). The protein adaptor may bind non-specifically and/or with low affinity to non-targets before binding with high affinity to its target, particularly if the non-targets are chemically similar to the target. In heterogeneous biological samples, the protein adaptor may be exposed to a variety of analytes that are not its target analyte. The protein adaptor may also undergo conformational changes within the lumen of the nanopore upon binding to its target analyte.

In certain embodiments, the lumen of the nanopore is at least 3 nm in diameter, for example, the diameter may measure 3 nm, 3.5 nm, 4 nm, 4.5 nm, 5 nm, 5.5 nm, 6 nm, 6.5 nm, 7 nm, or greater. The cis diameter of the nanopore lumen may be at least 3.5 nm and/or the trans diameter of the nanopore may be at least 6 nm. In general, cis refers to the end of the modified pore to which an analyte is added, while trans refers to the end of the modified nanopore through which the analyte exits after translocating the length of the nanopore lumen. In artificial lipid bilayers, for example, the trans end of a pore may be inserted in the lipid bilayer, while the cis end of the nanopore remains on the same side of the lipid bilayer. Accordingly, the cis diameter of the nanopore is the diameter of the opening at the cis end of the nanopore, while the trans diameter of the nanopore is the diameter at the opening of the opposite trans end of the nanopore. An analyte may be added to either side of the nanopore, for example, an analyte may be added to the cis opening of the nanopore so that it transverses the nanopore and exits from the trans side. Alternatively, an analyte may be added to the trans side of the nanopore. Nanopores are typically arrayed in a membrane such as a lipid bilayer, across which a potential can be applied. In general, the applied potential across the membrane refers to the potential of the trans electrode. Nanopores may be inserted into lipid bilayers from the cis compartment, which are connected to a ground electrode.

Protein Adaptors

A variety of protein adaptors may be fully or partially incorporated in the lumen of nanopores to form the nanopore sensors. In some embodiments, the protein adaptors are globular proteins (also called "spheroproteins"). The protein adaptors may be roughly spherical and may form colloids in water. For example, the protein adaptors may be characterized by apolar (hydrophobic) amino acids that are bounded towards the molecule's interior while polar (hydrophilic) amino acids are bound outwards.

In some embodiments, the protein adaptor is a single protein. In certain embodiments, the protein adaptor is a protein domains, oligomers, and/or fragment of a protein. The protein adaptor may also be a complex or combination of single proteins and/or fragments. In certain embodiments, the protein adaptor complex comprises a protein (or fragments or domains) complexed with a small analyte such as a small molecule and/or an inhibitor. In certain embodiments, the protein adaptor is a functional enzyme. In certain embodiments, the protein adaptor is a ligand-binding domain.

The protein adaptor must have dimensions that fit into a nanopore, for example, the protein adaptor may have a diameter that is smaller than the cis-diameter of the nanopore but larger than the trans-diameter of the nanopore. In some exemplary nanopores, the cis-diameter is wider than the trans-diameter, so the protein adaptor may pass through the cis end of the nanopore but not through the trans end. The protein adaptor may remain internalized for at least 0.1-1 μs, 1-10 μs, or 10-100 μs.

The cis-diameter of the nanopore may be at least 4.5 nm, 5.0 nm, 5.5 nm, 6.0 nm, 6.5 nm, or 7 nm, while the trans-diameter of the nanopore is at least 1.5 nm, 2.0 nm, 3.0 nm, 3.3 nm, 3.5 nm, or 4.0 nm. In certain embodiments, the cis-diameter of the nanopore is 5.5 nm and the trans-diameter of the nanopore is about 3.0 nm, for example 3.3 nm. A protein adaptor suitable for internalization in the nanopore may have an average diameter that is smaller than the cis-diameter of the nanopore (for example, smaller than 5.5 nm) but larger than the trans-diameter of the nanopore (for example, larger than 3.0 nm or 3.3 nm). Accordingly, such a protein adaptor added to the cis side of the nanopore would be able to enter the nanopore but would not exit from the trans side of the nanopore. Conversely, if the trans-diameter were larger than the cis-diameter, then a protein adaptor added to the trans side of the nanopore would enter through the trans-opening but would not exit from the cis-opening.

The average diameter of the protein adaptor may be determined by examination of the crystal structure, if available, or by estimation based on measurements such as molecular weight. For example, a protein with a molecular weight of about 20 kDa may be expected to have an average diameter of less than 3.5 nm, while a protein with a molecular weight of about 25 kDa may be expected to have an average diameter of more than 3.5 nm.

Nanopores typically have lumens that are either negatively or positively charged, as the charge is required for the electroosmotic flow of charged molecules (e.g., analytes) through the nanopore when an electric field is applied across the nanopore. For example, when a nanopore has a negatively-charged lumen and a negative potential is applied to one side of the nanopore (e.g., the trans side of the nanopore), then a positively charged molecule will pass freely through the nanopore from the cis end to the trans end. Accordingly, for nanopores with negatively-charged lumen, protein adaptors suitable for internalization in the nanopore may be positively- or negatively-charged. Charges are not limiting for the incorporation of the protein adaptor. For example, moderately negatively-charged molecules (pI>4-isoelectric point) can be incorporated.

Some protein adaptors are either too small to remain internalized in the nanopore and/or have a charge is not suitable for entry into the nanopore (i.e., a nanopore has a negatively-charged lumen but the protein has a highly negative charge). For example, if a protein has an average diameter that is smaller than both diameters of the nanopore, the protein may not be expected to remain internalized in the nanopore lumen. A protein that has an average diameter of less than 3.5 nm would not be expected to remain internalized for longer than a few milliseconds in a nanopore whose cis diameter is about 6.5 nm and whose trans diameter is about 3.5 nm. In some embodiments, a protein adaptor is tagged in order to be internalized in the nanopore and/or to be retained in the lumen of the nanopore. The tag may be a charged tag. For example, a protein may have a positively-charged tag in order to be internalized in a negatively-charged nanopore. The tag may be attached covalently or by other chemical means, or the tag may be present as a fusion with the protein adaptor, for example, the protein adaptor and tag may have been genetically encoded. In some embodiments, a tag comprises at least 4, 5, 6, 7, 8, 9, or 10 positively charged amino acid residues. Tags may comprise positively charged coils, spacers (e.g., flexible linkers), and/or labels for purification (e.g., strep tags). In some embodiments, the presence of a tag increases the retention time of the tagged protein adaptor by 100-fold or 1000-fold. Accordingly, the tagged protein adaptor may remain internalized in the nanopore for seconds whereas the untagged protein adaptor alone would only be internalized for milliseconds.

In some embodiments, the protein adaptor is an enzyme (also called an "enzyme adaptor"). The enzyme may be an oxidoreducase (Enzyme Commission (EC) 1), transferase (EC2), hydrolase (EC3), lyase (EC4), isomerase (EC5), or ligase (EC6). The enzyme may be selected from a demethylase or a reductase. In some embodiments, the enzyme is a demethylase. For example, the enzyme may be AlkB demethylase. In certain embodiments, the enzyme is a reductase, such as dihydrofolate reductase (DHFR). The protein adaptor may be complexed with a molecule such as a small molecule (e.g., co-factor, inhibitor, and/or any other small molecule that binds to the protein adaptor) to form an adaptor complex, and this adaptor complex may bind to a target analyte. For example, DHFR may be complexed with methotrexate (MTX) to form an adaptor complex.

In some embodiments, the protein adaptor comprises protein subunits, fragments, and/or domains of proteins. A protein subunit, fragment, or domain may be suitable for internalization, or may be made suitable by adding tags to increase size and/or charge. A protein adaptor complex may comprise a protein subunit, fragment, or domain.

Other exemplary protein adaptors include but are not limited to antibodies, nanobodies, artificially designed binding elements, ligand binding proteins (for example, venus fly trap domains), transcription factors, metal-binding proteins, intrinsically unfolded binders, and more.

Uses of Nanopore Sensors (a) Detection and Identification of Analytes

Any analyte (or "target," "target analyte," "ligand," "substrate," or "binding partner") that binds to a protein adaptor may be detected using the nanopore sensors described herein. Analytes include small molecules, including organic and inorganic molecules, and biological molecules such as proteins and nucleic acids. Analytes may be charged or may be uncharged molecules. In some embodiments, the analytes detected by the nanopore sensors disclosed herein are charged molecules. The charged molecules may be proteins or small molecules.

Analytes may be known targets of the protein adaptor, for example, if the nanopore is used to determine whether a known binding partner of the protein adaptor is present in a mixture. Alternatively, new binding partners for the protein adaptor may be identified, for example, by screening a library of compounds or molecules which were not previously known to bind to the protein adaptor.

Accordingly, one aspect of the present invention relates to a method for detecting an analyte in a sample, comprising obtaining a nanopore sensor comprising a nanopore and a protein adaptor internalized in the lumen of the nanopore, adding the sample to the cis side or the trans side of the nanopore, and measuring conductance across the nanopore, wherein a change in conductance after adding the sample indicates that the analyte is present in the sample and has bound to the protein adaptor. In some embodiments, conductance is measured continuously before, during, and after addition of the analyte.

A further aspect relates to a method for identifying a ligand for a protein adaptor, comprising obtaining a nanopore sensor comprising a nanopore and a protein adaptor internalized in the lumen of the nanopore, adding a test compound to the cis side or the trans side of the nanopore, and measuring the conductance across the nanopore, wherein a change in conductance after adding the test compound indicates that the test compound is a ligand that binds to the protein adaptor.

In some embodiments, the change in conductance is a change in the current blockades ($I_B$), i.e., residual currents calculated as a percentage of the open pore current (IRES %). Thus, binding of an analyte to the protein adaptor may cause an increase in current blockades. In some embodiments, the current blockade is decreased. In certain embodiments, the change in current conductance is a measurable change in the noise pattern.

Conductance across the nanopore is sensitive and highly specific to the identity of the ligand that binds to the protein adaptor. Conductance measurements may be used to differentiate between two ligands that differ from one another by a single atom. For example, the binding of a protein adaptor (or adaptor complex) to a specific substrate has a different conductance than the binding of the protein adaptor (or adaptor complex) to the substrate that lacks a hydride ion. Thus, binding of an internalized protein to NADPH may be distinguished from binding of the internalized protein to NADP+.

(b) Enzyme Binding and Activity

A protein adaptors may be an enzyme ("enzyme adaptor," "internalized enzyme," or "enzyme"), and various aspects of enzyme binding, activity, and function may be studied using a nanopore sensor comprising a nanopore and an enzyme adaptor. A further aspect of the present disclosure relates to a method for measuring enzyme kinetics, comprising obtaining a nanopore sensor comprising a nanopore and an enzyme adaptor internalized in the lumen of the nanopore, adding a ligand to the cis side or the trans side of the nanopore, measuring a first conductance change across the nanopore which reflects binding of the ligand to the enzyme adaptor, and measuring additional conductance changes across the nanopore which reflect enzyme kinetics such as association and dissociation of the ligand and the enzyme adaptor. In some embodiments, the measurements are obtained continuously over time while the ligand concentration is varied (e.g., increased).

In certain embodiments, the method further comprises increasing the applied potential across the nanopore until the ligand dissociates from the enzyme adaptor, and the dissociation is measured by a change in conductance (for example, a decrease or increase in $I_B$). In certain embodiments, the method further comprises decreasing the applied potential across the nanopore until the ligand binds to the enzyme adaptor, and the binding is measured by a change in conductance (for example, an increase or decrease in $I_B$). In some embodiments, dissociation rate constants ($k_{off}$) is measured from the inverse of the dwell times of the ligand-binding events ($1/\tau_{off}$), and does not depend on the concentration of the ligand. In certain embodiments, the frequencies of the ligand-induced events ($f=1/\tau_{on}$) increase linearly with the concentration of the ligand, from which slopes the association rate constants ($k_{on}$) are calculated.

Notably, the enzyme adaptor retains its structure, binding sites, and activity. The ligand of the enzyme adaptor may be a substrate for the enzyme. Thus, an additional aspect of the present disclosure relates to a method for measuring activity of an enzyme adaptor on a substrate, comprising obtaining a nanopore sensor comprising a nanopore and an enzyme adaptor internalized in the lumen of the nanopore, adding the substrate to the cis side or the trans side of the nanopore, and measuring conductance across the nanopore, wherein a change in conductance after adding the ligand indicates activity of the enzyme adaptor on the substrate. The activity may be binding, cleavage, conformational changes, and/or other changes mediated by enzymes acting on their substrate.

In some embodiments, competitive binding between two substrates can be monitored by conductance changes as the substrates bind and dissociate with the enzyme adaptor.

All publications and patents mentioned herein are hereby incorporated by reference in their entirety as if each individual publication or patent was specifically and individually indicated to be incorporated by reference. In case of conflict, the present application, including any definitions herein, will control.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention is now illustrated with examples which disclose specific embodiments of the invention.

EXAMPLES

Example 1

Material & Methods

Unless otherwise specified all chemicals were bought from Sigma-Aldrich. DNA was purchased from Integrated DNA Technologies (IDT), enzymes from Fermentas and lipids from Avanti Polar Lipids. Stocks of NADPH and NADP+ (prepared in 15 mM Tris.HCl pH 7.5 150 mM NaCl) were kept at −20° C. and defrosted for single use. All errors in this work are given as standard deviations. The standard deviations (SD) for the values calculated from linear fits (FIG. 1e, FIG. 2e) were calculated from standard errors (SE) given by the fit by applying the formula $$SE = \frac{SD}{\sqrt{N}}$$

where N is the number of independent data points in the graph.

AlkB Cloning

To allow cloning, a Nco I site (CCATGG) was introduced in the wild type AlkB from *E. coli* at the beginning of the gene (5' end). To keep the gene in reading frame an additional two bases were inserted after the Nco I site, resulting in an additional alanine residue after the starting methionine. For purification purposes, at the C-terminus of AlkB, a strep-tag was attached via a flexible glycine-serine-alanine linker and the open reading frame was terminated by two consecutive stop codons, followed by a Hind III restriction site (3' end). The attachment of the strep-tag was carried out in two consecutive PCR reactions. During the first PCR reaction, the AlkB gene was amplified directly from the genomic DNA of a single BL21(DE3) *E. coli* (Lucigen) colony using Phire Hot Start II DNA polymerase (Finnzymes), 6 µM fAlkB (Table 5) and AlkBr1 (Table 5) primers in a 50 µL reaction volume. The PCR reaction cycling protocol was as follows: pre-incubation step at 98° C. for 30 s and then 30 cycles of denaturation at 98° C. for 5 s and extension at 72° C. for 1 min. The amplified product was purified using QIAquick PCR Purification Kit (Qiagen) and served as a template for the second PCR reaction, which used ~100 ng of the purified PCR product amplified by Phire Hot Start II DNA polymerase using 6 µM of fAlkB (Table 5) and AlkBr2 (Table 5) primers in 300 µL volume. The cycling protocol was the same as in the previous step. The resulting PCR product containing the strep-tagged AlkB gene was purified with QIAquick PCR Purification Kit (Qiagen) and digested with Nco I and Hind III (FastDigest, Fermentas). The gel purified insert (QIAquick Gel Extraction Kit, Qiagen) was cloned under control of the T7 promoter into the pT7-SC1 expression plasmid using sticky-end ligation (T4 ligase, Fermentas) via Nco I (5') and Hind III (3') sites. 0.6 µL of the ligation mixture was transformed into 50 µL of E. Cloni® 10G cells (Lucigen) by electroporation. The transformed bacteria were grown overnight at 37° C. on ampicillin (100 µg/ml) LB agar plates. The identity of the clones was confirmed by sequencing. The DNA and proteins sequences of strep-tagged AlkB are included in the sequence listing (see Table 6).

Construction of the $DHFR_{n+}$ Genes

The synthetic gene encoding for *E. coli* DHFR was made by GenScript. The wild-type gene was modified by the substitution of the two Cys residues at positions 85 and 152 with Ala and Ser respectively (referred to as DHFR throughout SI and main text). Those substitutions were shown to be functionally tolerated by DHFR (Plesa, C. et al. (2013) *Nano Lett.*, 13, 658-663). Further, the DNA sequence encoding for Met-Ala-Ser-Ala was added at the beginning of the gene in order to introduce a Nco I restriction site. To facilitate construction steps, a Xho I restriction site was introduced between the C-terminal tags and DHFR.

As a first step the $DHFR_{10+}$ construct was built (FIG. 10, for DNA and protein sequence see below). 100 ng of the synthetic DHFR gene was amplified with 5 µM of DHf and DHr primers (Table 5) with Phire Hot Start II DNA polymerase (Finnzymes) in 400 µL final volume (pre-incubation at 98° C. for 30 s, then cycling: denaturation at 98° C. for 5 s, extension at 72° C. for 1 min for 30 cycles). The synthetic fragment encoding for the 10+ tag (made by IDT, for sequence see below) was amplified as described above using Cof and Cor primers (Table 5). DHf and Cof primers contain sequences that are the reverse-complement of each other, introducing sequence overlap between DHFR and 10+ tag PCR products, necessary for the next step, where both PCR products (2 µeach, gel-purified, QIAquick Gel Extraction Kit, Qiagen) were assembled together using Phire Hot Start II DNA polymerase (Finnzymes) in 50 µL final volume (pre-incubation at 98° C. for 30 s, then cycling: denaturation at 98° C. for 5 s, extension at 72° C. for 1 min for 7 cycles). ~100 ng of the purified (QIAquick PCR Purification Kit (Qiagen)) assembly product was amplified with 5 µM of DHf and Cor primers (Table 5), using Phire Hot Start II DNA polymerase (Finnzymes) in 400 µL final volume (pre-incubation at 98° C. for 30 s, then cycling: denaturation at 98° C. for 5 s, extension at 72° C. for 1 min for 30 cycles). PCR product encoding for the whole length $DHFR_{10+}$ was purified using the QIAquick PCR Purification Kit (Qiagen) and digested with Nco I and Hind III (FastDigest, Fermentas). The resulting insert was gel purified and cloned under control of the T7 promoter into the pT7-SC1 expression plasmid [Miles, G. et al. (2001) *Biochem.* 40, 8514-8522] using sticky-end ligation (T4 ligase, Fermentas) via Nco I (5') and Hind III (3') sites. 0.6 µL of the ligation mixture was transformed into E. Cloni® 10G cells (Lucigen) by electroporation. The transformed bacteria were selected overnight at 37° C. on ampicillin (100 µg/ml) LB agar plates. The identity of the clones was confirmed by sequencing. The DNA and protein sequence of $DHFR_{10+}$ is provided below with the 10+ tag sequence indicated by capital letters in the DNA sequence.

DHFR, $DHFR_{4+}$ and $DHFR_{tag}$ constructs (FIG. 10) were built by deleting parts of the 10+ tag via whole plasmid PCR amplification followed by Xho I digestion and unimolecular ligation as follows: ~100 ng of the DHFR_10+ tag plasmid was amplified using 5 μM of dcr and delF (to produce DHFR), or 2 dcF (DHFR$_{4+}$) or dcf (DHFR$_{tag}$) using Phire Hot Start II DNA polymerase (Finnzymes) in 100 μL final volume (pre-incubation at 98° C. for 30 s, then cycling: denaturation at 98° C. for 5 s, extension at 72° C. for 1.5 min for 30 cycles, primer sequences see Table 5). PCR products were purified with QIAquick PCR Purification Kit (Qiagen), digested with Xho I (FastDigest, Fermentas) and ligated with T4 ligase (Fermentas). 0.6 μL of the ligation mixture was transformed into E. Cloni® 10G cells (Lucigen) by electroporation. The transformed bacteria were selected overnight at 37° C. on ampicillin (100 μg/ml) LB agar plates. The identity of the clones was confirmed by sequencing.

Construction of N120D AlkB Mutant

The AlkB gene was amplified using 120D (forward) and T7 terminator (reverse) primers (Table 5). The PCR conditions were: 0.3 mL final volume of PCR mix (150 μl of RED Taq ReadyMix, 6 μM of forward and reverse primers, ~400 ng of template plasmid), cycled for 27 times (after a pre-incubation step at 95° C. for 3 min, a cycling protocol was then applied: denaturation at 95° C. for 15 s, annealing at 55° C. for 15 s, extension at 72° C. for 3 min). The resulting PCR product was gel purified (QIAquick Gel Extraction Kit, Qiagen) and cloned into a pT7 expression plasmid (pT7-SC1) by MEGAWHOP procedure [Miyazaki, K. (2011) Methods Enzymol 498, 399-406]: ~500 ng of the purified PCR product was mixed with ~300 ng of the WT AlkB circular DNA template and the amplification was carried out with Phire Hot Start II DNA polymerase (Finnzymes) in 50 μL final volume (pre-incubation at 98° C. for 30 s, then cycling: denaturation at 98° C. for 5 s, extension at 72° C. for 1.5 min for 30 cycles). The circular template was eliminated by incubation with Dpn I (1 FDU) for 2 hr at 37° C. 0.6 μL of the resulted mixture was transformed into 50 μL of E. Cloni® 10G cells (Lucigen) by electroporation. The transformed bacteria were grown overnight at 37° C. on ampicillin (100 μg/ml) LB agar plates. The identity of the clones was confirmed by sequencing.

Purification of the Strep-Tagged AlkB-Fe$^{++}$ pT7-SC1 plasmids containing the strep-tagged AlkB gene were transformed into E. Cloni® EXPRESS BL21(DE3) cells (Lucigen). Transformants were selected on LB agar plates supplemented with 100 μg/ml ampicillin grown overnight at 37° C. The resulting colonies were grown at 37° C. (200 rpm shaking) in 2x YT medium supplemented with 100 μg/ml ampicillin until the O.D. at 600 nm was ~0.8. The cultures were then supplemented with 25 μM FeSO$_4$ and 100 μM L(+)-ascorbic acid (Merck) from fresh stock solutions (25 mM FeSO$_4$ and 100 mM L(+)-ascorbic acid in ddH$_2$O) and the protein expression was induced by supplementing with 0.5 mM IPTG. Bacteria were further grown overnight at 25° C., 200 rpm shaking. The next day the bacteria were harvested by centrifugation at 6000xg at 4° C. for 25 min. The resulting pellets were frozen at −80° C. until further use.

Figures 10, 12, 13:
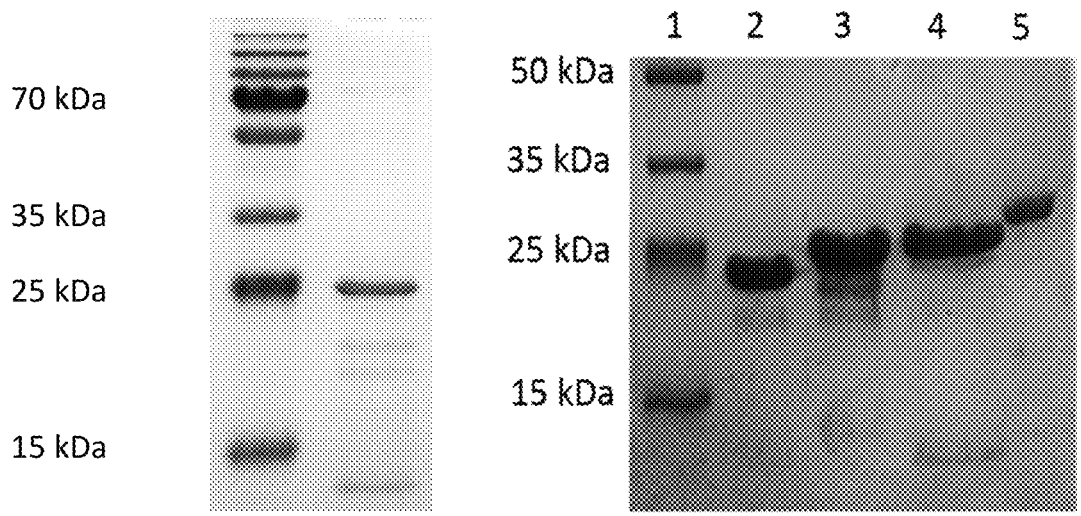
FIG. 10 shows sequences of the 1+, 4+, tag (5 positive charges) and 10+ fusions to the DHFR C-terminus. The C-terminus of DHFR, the sequences of the S-tag, the positive coil and the Strep-tag are colored green, gray, cyan and yellow, respectively. The sequences of the flexible linkers are underlined. The positively charged amino acids in the polypeptide tags are indicated by an asterisk (*) and the negatively charged amino acids by a minus sign (−).
FIG. 12 shows the purity of the strep-tagged purified wild type AlkB-Fe$^{++}$ assayed by a 12% SDS PAGE. In the left lane is a protein marker (Page Ruler Plus Prestained Protein Ladder, Thermo scientific); in the right lane is 5 µg of the purified AlkB-Fe$^{++}$.
FIG. 13 shows the purity of the strep-tagged purified DHFR$_{n+}$ assayed by a 15% SDS PAGE. In lane 1 is a protein marker (Page Ruler Plus Prestained Protein Ladder, Thermo scientific). Lanes 2-4 contain ~5 µg each of purified DHFR (lane 2), DHFR$_{4+}$ (lane 3), DHFR$_{tag}$ (lane 4) and lane 5 contains ~10 µg of purified DHFR$_{10+}$.

AlkB-Fe$^{++}$ was purified as following: bacterial pellets originating from 100 ml culture were resuspended in 30 ml lysis buffer (150 mM NaCl, 15 mM Tris.HCl pH 8.0, 1 mM MgCl$_2$, 0.2 units/ml DNase, 10 μg/ml lysozyme) supplemented with 5 μl β-mercaptoethanol (Merck) and 25 μM FeSO$_4$ and 100 μM L(+)-ascorbic acid, and incubated at RT for 20 min. Bacteria were further disrupted by probe sonication, and the crude lysate was clarified by centrifugation at 6000xg at 4° C. for 30 min. The supernatant was allowed to bind to ~150 μl (bead volume) of Strep-Tactin® Sepharose® (IBA) pre-equilibrated with the wash buffer (150 mM NaCl, 15 mM Tris.HCl pH 8.0) supplemented with 25 μM FeSO$_4$ and 100 μM L(+)-ascorbic acid, for 1 hr at 4° C. ("end over end" mixing). Then the resin was loaded on a column (Micro Bio Spin, Bio-Rad) and washed with ~20 column volumes of the wash buffer supplemented with 25 μM FeSO$_4$ and 100 μM L(+)-ascorbic acid followed by ~3 column volumes of 150 mM NaCl, 15 mM Tris.HCl pH 8.0 (metal ions might interfere with the ClyA recordings, unpublished results, thus excess of iron was avoided). AlkB-Fe$^{++}$ was subsequently eluted from the column in ~300 μl of elution buffer (150 mM NaCl, 15 mM Tris.HCl pH 8.0, 5 mM D-desthiobiotin (IBA)). Purified AlkB-Fe$^{++}$ remained active for weeks, in agreement with the fact that self-inactivation of AlkB requires the presence of 2-OG.[32] The concentration of AlkB-Fe$^{++}$ was measured using Bradford assay and the purity was checked using a 12% SDS-PAGE (FIG. 12).

Purification of the Strep-Tagged DHFR$_{n+}$

After transformation of pT7-SC1 plasmids containing the strep-tagged DHFR$_{n+}$ gene into E. Cloni® EXPRESS BL21 (DE3) cells (Lucigen), transformants were selected on LB agar plates supplemented with 100 μg/ml ampicillin after overnight growth at 37° C. The resulting colonies were grown at 37° C. (200 rpm shaking) in 2x YT medium supplemented with 100 μg/ml ampicillin until the O.D. at 600 was ~0.8, after which DHFR$_{n+}$ expression was induced by addition of 0.5 mM IPTG, and subsequent switching to 25° C. for overnight growth. The next day the bacteria were harvested by centrifugation at 6000xg at 4° C. for 25 min and the resulting pellets were frozen at −80° C. until further use.

For purification, bacterial pellets originating from 100 ml culture were resuspended in 30 ml lysis buffer (150 mM NaCl, 15 mM Tris.HCl pH 7.5, 1 mM MgCl$_2$, 0.2 units/ml DNase, 10 μg/ml lysozyme) and incubated at RT for 20 min. Bacteria were further disrupted by probe sonication, and the crude lysate was clarified by centrifugation at 6000xg at 4° C. for 30 min. The supernatant was allowed to bind to ~150 μl (bead volume) of Strep-Tactin® Sepharose® (IBA) pre-equilibrated with the wash buffer (150 mM NaCl, 15 mM Tris.HCl pH 7.5)—"end over end" mixing. The resin was then loaded on a column (Micro Bio Spin, Bio-Rad) and washed with ~20 column volumes of the wash buffer. DHFR$_{n+}$ was subsequently eluted from the column in ~300 μl of elution buffer (150 mM NaCl, 15 mM Tris.HCl pH 7.5, 5 mM D-Desthiobiotin (IBA)). The concentration of DHFR$_{n+}$ was measured using Bradford assay and the purity was checked using a 12% SDS-PAGE (FIG. 13). Proteins were stored at 4° C. (up to 3 weeks) until use.

ClyA-AS Protein Overexpression and Purification

E. Cloni® EXPRESS BL21 (DE3) cells were transformed with the pT7-SC1 plasmid containing the ClyA-AS gene. ClyA-AS contains eight mutations relative to the S. Typhi ClyA-WT: C87A, L99Q, E103G, F166Y, I203V, C285S, K294R and H307Y (the H307Y mutation is in the C-terminal hexahistidine-tag added for purification).[18] Transformants were selected after overnight growth at 37° C. on LB agar plates supplemented with 100 mg/L ampicillin. The resulting colonies were inoculated into 2x YT medium containing 100 mg/L of ampicillin. The culture was grown at 37° C., with shaking at 200 rpm, until it reached an OD$_{600}$ of ~0.8. The expression of ClyA-AS was then induced by the addition of 0.5 mM IPTG and the growth was continued at 25° C. The next day the bacteria were harvested by centrifugation at 6000xg for 25 min at 4° C. and the pellets were stored at −80° C.

The pellets containing monomeric ClyA-AS were thawed and resuspended in 20 mL of wash buffer (10 mM imidazole, 150 mM NaCl, 15 mM Tris.HCl, pH 8.0), supplemented with 1 mM $MgCl_2$ and 0.05 units/mL of DNase I and the bacteria were lysed by sonication. The crude lysates were clarified by centrifugation at 6000×g for 20 min at 4° C. and the supernatant was mixed with 200 µL of Ni-NTA resin (Qiagen) in wash buffer. After 1 hr, the resin was loaded into a column (Micro Bio Spin, Bio-Rad) and washed with ~5 ml of the wash buffer. ClyA-AS was eluted with approximately ~0.5 mL of wash buffer containing 300 mM imidazole. Protein concentration was determined by the Bradford assay. Because ClyA-AS monomers were not active upon freezing, they were stored at 4° C. until further use.

Type I ClyA-AS oligomers were obtained by incubation of ClyA-AS monomers with 0.5% β-dodecylmaltoside (DDM, GLYCON Biochemicals, GmbH) at 25° C. for 15 min. ClyA-AS oligomers were separated from monomers by blue native polyacrylamide gel electrophoresis (BN-PAGE, Bio-rad) using 4-20% polyacrylamide gels. The bands corresponding to Type I ClyA-AS were excised from the gel and were placed in 150 mM NaCl, 15 mM Tris.HCl pH 8.0 supplemented with 0.2% DDM and 10 mM EDTA to allow diffusion of the proteins out of the gel.

Electrical Recordings in Planar Lipid Bilayers

The applied potential refers to the potential of the trans electrode. ClyA-AS nanopores were inserted into lipid bilayers from the cis compartment, which was connected to the ground electrode. The two compartments were separated by a 25 µm thick polytetrafluoroethylene film (Goodfellow Cambridge Limited) containing an orifice of ~100 µm in diameter. The aperture was pretreated with ~5 µl of 10% hexadecane in pentane and a bilayer was formed by the addition of ~10 µL of 1,2-diphytanoyl-sn-glycero-3-phosphocholine (DPhPC) in pentane (10 mg/mL) to both electrophysiology chambers. Typically, the addition of 0.01-0.1 ng of oligomeric ClyA-AS to the cis compartment (0.5 mL) was sufficient to obtain a single channel. ClyA-AS nanopores displayed a higher open pore current at positive than at negative applied potentials, which provided a useful tool to determine the orientation of the pore. Electrical recordings were carried out in 150 mM NaCl, 15 mM Tris.HCl pH 8.0 (AlkB experiments) or 150 mM NaCl, 15 mM Tris.HCl pH 7.5 (DHFR experiments). The temperature of the recording chamber was maintained at 28° C. by water circulating through a metal case in direct contact with the bottom and sides of the chamber.

Data Recording and Analysis

Electrical signals from planar bilayer recordings were amplified using an Axopatch 200B patch clamp amplifier (Axon Instruments) and digitized with a Digidata 1440 A/D converter (Axon Instruments). Data were recorded by using the Clampex 10.4 software (Molecular Devices) and the subsequent analysis was carried out with the Clampfit software (Molecular Devices). Electrical recordings were performed in 150 mM NaCl, 15 mM Tris.HCl pH 8.0 (AlkB) or pH 7.5 (DHFR) by applying a 2 kHz low-pass Bessel filter and a 10 kHz sampling rate. For further analysis traces were filtered digitally with a Bessel (8-pole) low-pass filter with a 50 Hz cut-off. Residual current values ($I_{RES}$%) were calculated from blocked pore current values ($I_B$) and open pore current values ($I_O$) as $I_{RES\ \%}=100*I_B/I_O$. $I_B$ and $I_O$ were determined from Gaussian fits to all point current histograms (0.05 pA bin size) for at least 15 individual protein blockades. $\Delta I_{RES\ \%}$ values were calculated from $I_{RES\ \%}$ using propagation of errors.

Current transitions from level 1 were analyzed with the "single-channel search" function in Clampfit. The detection threshold to collect the ligand-induced events for AlkB was set to 4 pA and events shorter than 10 ms were ignored. For NADP+ and "short" NADPH binding events to $DHFR_{tag}$:MTX, the detection threshold was also set to 4 pA and events shorter than 1 ms were neglected. The resulting event dwell times ($t_{off}$) and the time between events ($t_{on}$) were binned together as cumulative distributions and fitted to a single exponential to retrieve the ligand-induced lifetimes ($\tau_{off}$) and the ligand-induced event frequencies ($f=1/\tau_{on}$). The process of event collection was monitored manually. For AlkB, final values of $\tau_{on}$ and $\tau_{off}$ were based on average values derived from at least 3 single channel experiments at each concentration. Each experiment analysed more than 8 AlkB blockades. At the low ligand concentrations (0.2 mM) about 100 ligand-binding events were measured. Otherwise more than 150 events were collected. In total, 500-1200 events were considered for 2-OG, 350-2100 events for SUC (350 events were collected at the lowest concentration, all other concentrations more than 800 events) and 500-1300 events for N-OG. For $DHFR_{tag}$:MTX, >500 NADPH and >2000 NADP+ binding events were used in total to determine the values of $\tau_{on}$ and $\tau_{off}$, where individual values for $t_{on}$ and $t_{off}$ were derived for at least five single channel experiments, each analysing more than 40 $DHFR_{tag}$:MTX blockades and more than 2000 ligand-binding events. Since the life time of the "long" NADPH binding events to $DHFR_{tag}$:MTX binary complex exceeded the residence time of the binary complex in the ClyA-AS nanopore (the dissociation of "long" NADPH was only occasionally observed), $t_{off}$ values could not be determined. $t_{on}$ values for NADPH were determined by collecting the times between the capture of the $DHFR_{tag}$:MTX binary complex in the nanopore and the transition to the ~4 pA higher current level within the same blockade lasting longer than 0.2 s. Subsequently, the $t_{on}$ values were binned together as cumulative distributions and fitted to a single exponential fit to retrieve characteristic $\tau_{on}$ values. The values for $k_{off}$ represented in FIG. 2b and FIG. 4b were determined by taking the average±standard deviations of $1/t_{off}$ of at least 3 single channel experiments. The values of the association rate constants ($k_{on}$) were determined from the slope of the linear regression curves calculated from the dependency of the event frequencies ($f=1/\tau_{on}$) on the ligand concentration (OriginLab, FIGS. 2b and 4b). Graphs were made with Origin (OriginLab Corporation) or Clampfit software (Molecular Devices).

Example 2

A Demethylase as a Protein Adaptor

As a first model protein we selected *E. coli* AlkB demethylase (Mw=25 kDa), a globular protein that is expected to pass the cis entry of ClyA, but is too large to traverse the trans exit of the nanopore (FIG. 1a,b). In complex with iron ions (AlkB-$Fe^{++}$) AlkB co-oxidises methylated DNA and its cofactor 2-oxoglutarate (2-OG), producing succinate (SUC), carbon dioxide and formaldehyde (Aravind, L. & Koonin, E. V. (2001) *Genome biol.* 2, RESEARCH0007; Trewick, S. C. (2002) *Nature* 419, 174-178), 2-oxoglutarate is an important metabolite that influences aging and age-related diseases (Chin, R. M. et al. (2014) *Nature,* 510, 397-401), and is a biomarker for non-alcoholic fatty liver disease (Rodriguez-Gallego, E. (2015) *Int. j. obesity* 39, 279-287), heart failure and cardiorenal syndrome (Nikolaidou, T. et al. (2010)

*Heart*, 96, e14). The level of succinate in urine is a biomarker for kidney damage (Peti-Peterdi, J. (2014) U.S. Pat. No. 8,652,771).

Figure 1B:
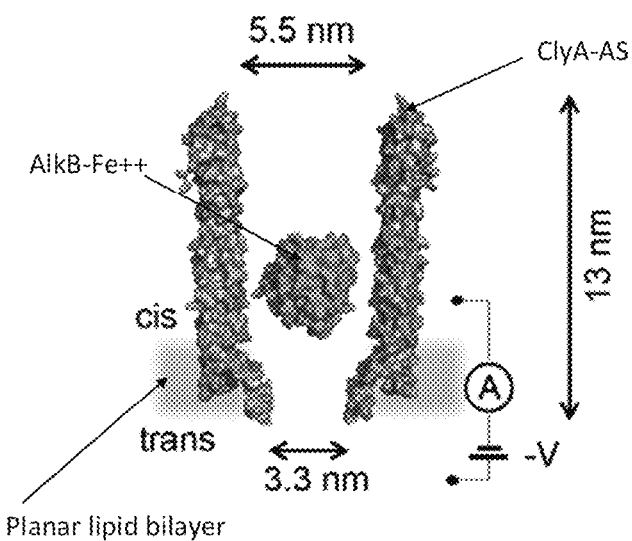

Individual AlkB-Fe$^{++}$ molecules were studied using Type I ClyA-AS (ClyA-AS hereafter). In 150 mM NaCl, 15 mM Tris HCl and pH 8.0 ClyA-AS formed nanopores with a steady open pore conductance ($I_O$=−1.7±0.1 nSi, average±SD, N=38, −60 mV, 28° C.) under a wide range of applied potentials. Here and hereafter N indicates the number of independent single nanopore experiments, np the number of individual protein block-ades and nl the total number of ligand binding events analysed. The addition of AlkB-Fe$^{++}$ (~4 nM) to the cis side of ClyA-AS provoked current blockades ($I_B$), quoted here as residual currents calculated as a percentage of the open pore current ($I_{RES\%}$), due to the electroosmotic confinement of AlkB-Fe$^{-+}$ between the wider cis entrance and the narrower trans exit of the protein nanopore (FIG. 1b)[18,20]. Conveniently, AlkB-Fe$^{++}$ remained trapped inside the nanopore for several minutes (FIG. 1c). The signal induced by AlkB-Fe$^{++}$ fluctuated between two distinctive current levels, L1 ($I_{RES\%}$=52.6±2.0%, n=15, N=7) and L2 ($I_{RES\%}$=39.0±1.0%, $n_p$=15, N=7, FIG. 1c), possibly due to two residence sites for the protein within the lumen of the ClyA-AS nanopores (Soskine, M. (2012) *Nano Lett.* 12, 4895-4900).

Figure 2A:
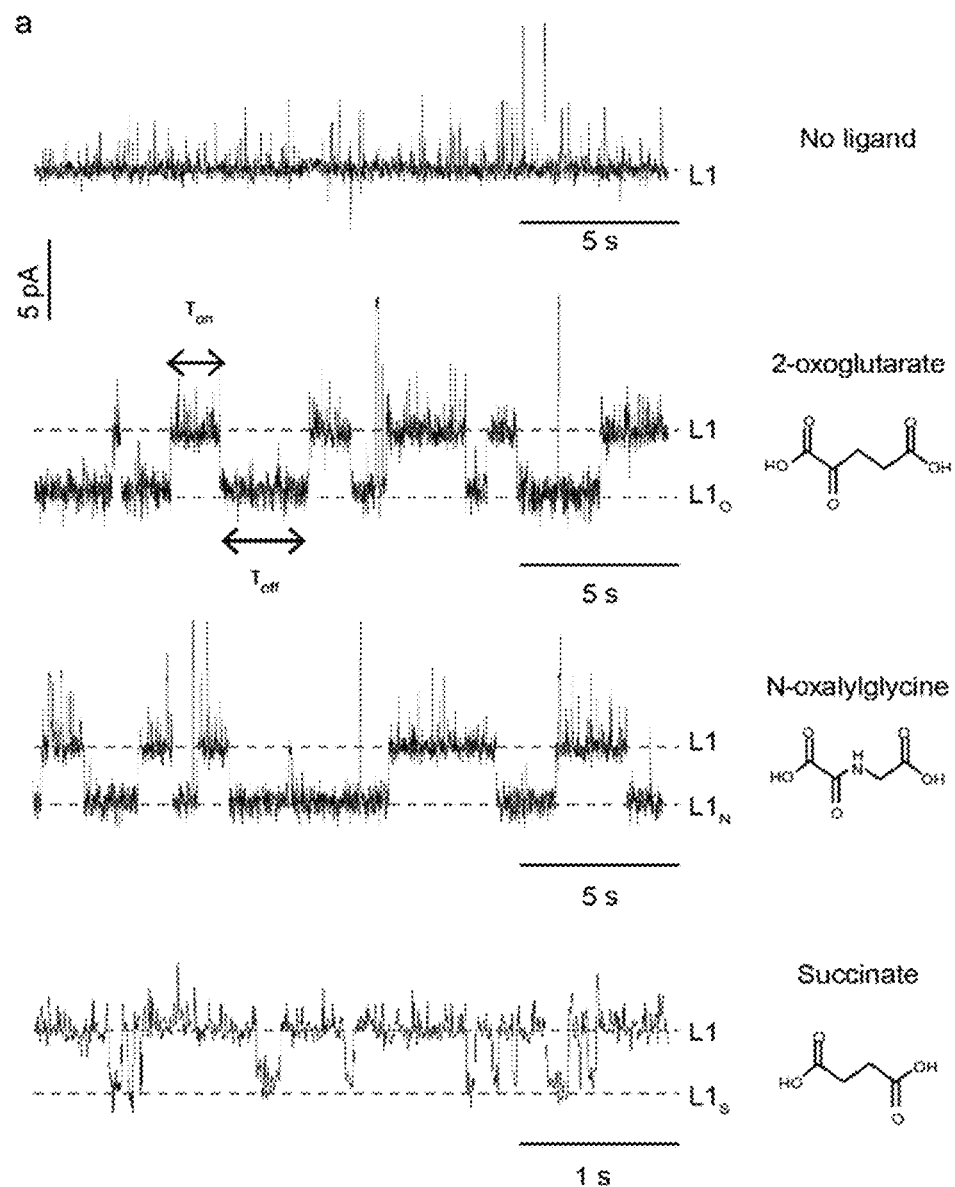
Figure 5:
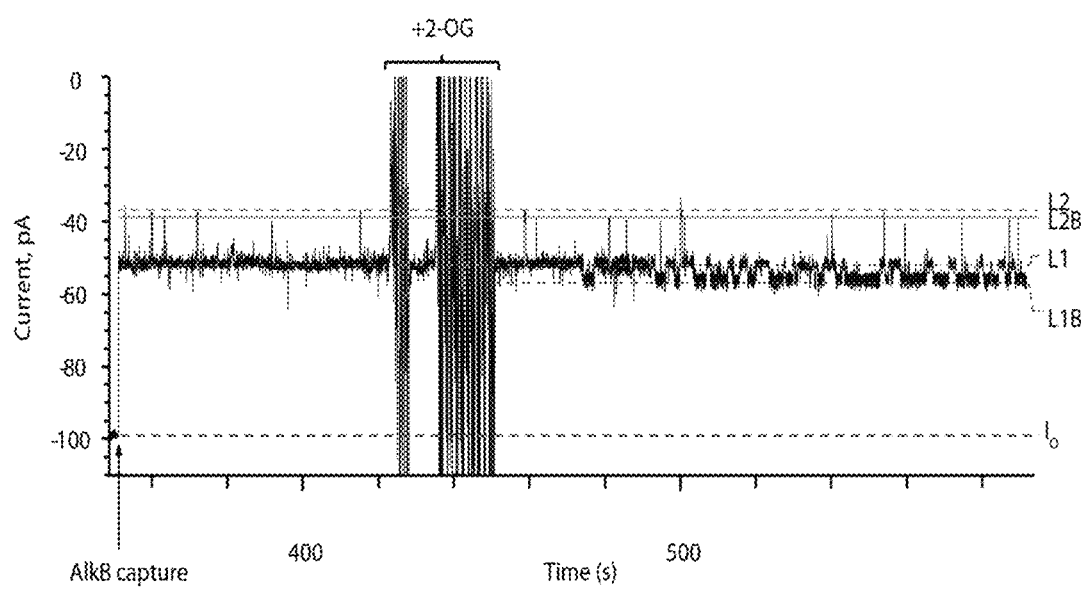
FIG. 5 shows 2-OG induced binding events to a single AlkB-Fe$^{++}$ molecule. The current trace shows the capture of an AlkB-Fe$^{++}$ molecule (arrow) previously added to the cis compartment followed by the addition of 2-OG to the cis compartment. Confined AlkB-Fe$^{++}$ showed L1 and L2 current levels, while 2-OG binding induced L1B and L2B ionic current levels. (All current levels are labeled). The grey dashed line corresponds to the open pore current (I$_o$). The trace was recorded at −60 mV applied potential in 150 mM NaCl, 15 mM Tris.HCl pH 8.0 at 28° C. using 2 kHz filtering and 10 kHz sampling rate, and filtered digitally with a Bessel (8-pole) low-pass filter with 50 Hz cut-off.
Figure 6A:
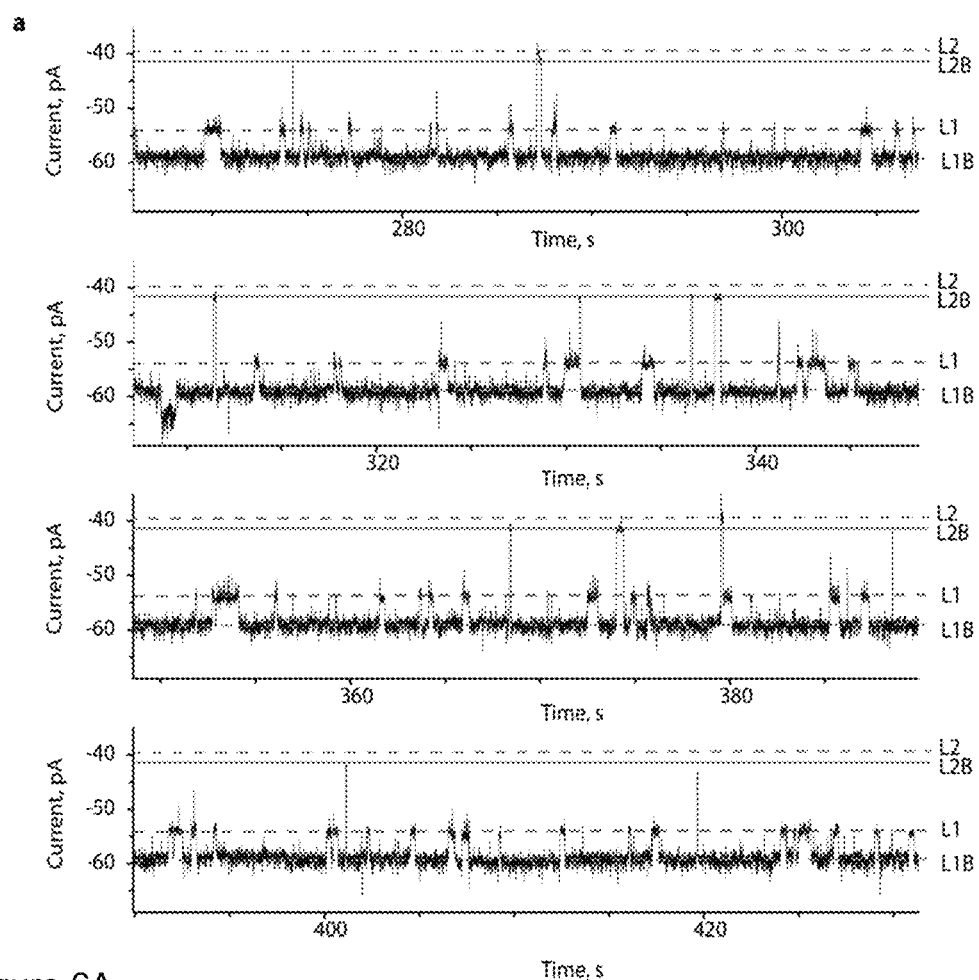

At −60 mV the addition to the cis reservoir of the cofactor (2-OG), an isosteric inhibitor (N-oxalylglycine, N-OG) or the processed cofactor (SUC) induced reversible current enhancements within the AlkB-Fe$^{++}$ blockades ($\Delta I_{RES\%}$= +4.7±1.3%, +4.9±1.0 and +4.6±1.3, respectively, n=15 AlkB blockades with each AlkB blockade typically $n_p$>15, $n_l$>75 ligand binding events, N>4, N>4 single channel experiments, FIG. 2a, FIGS. 5 and 6, and Table 1) that showed a mean duration ($t_{off}$) of 1.7±0.5 s, 1.8±0.4 s and 61±11 ms, respectively (>4500 ligand binding events, N>8 single channel experiments, with each experiment typically analysing n>10 AlkB blockades).

Figure 2B:
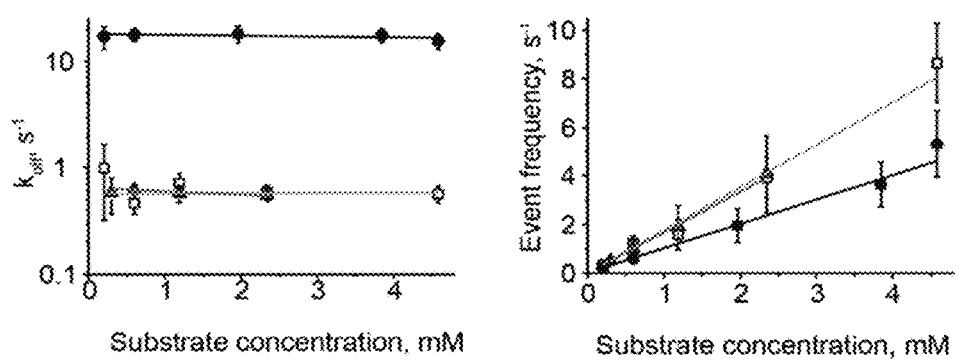

51, 3334-3341]. To confirm this hypothesis we tested an AlkB mutant where the asparagine at position 120, which has been reported to be involved in the binding of 2-OG to AlkB, was substituted by aspartate (N120D). The addition of 7.2 mM of 2-OG did not induce current transitions to the N120D-AlkB-Fe$^{++}$ blockades (N=4), suggesting that the affinity of this AlkB mutant for 2-OG is strongly reduced. As expected for a protein-ligand association process the dissociation rate constants ($k_{off}$, Table 2), measured from the inverse of the dwell times of the ligand-binding events (1/$\tau_{off}$), did not depend on the concentration of the ligand, while the frequencies of the ligand-induced events (f=1/$\tau_{on}$) increased linearly with the concentration of the three ligands, from which slopes the association rate constants ($k_{on}$) could be calculated (FIG. 2b, Table 2).

TABLE 2

Kinetic parameters for ligand binding to AlkB—Fe$^{++}$.
All data were collected in 150 mM NaCl, 15 mM Tris•HCl pH 8.0 at 28° C. Errors are given as standard deviations.
Proteins and ligands were added to the cis chamber.

|  | 2-OG | SUC | N-OG |
|---|---|---|---|
| $k_{off}^{-60\,mV}$ (s$^{-1}$) | 0.66 ± 0.33 | 16.6 ± 2.6 | 0.57 ± 0.10 |
| $k_{on}^{-60\,mV}$ (s$^{-1}$ M$^{-1}$) | 1.8 ± 0.3 × 10$^3$ | 9.2 ± 1.3 × 10$^2$ | 1.2 ± 0.3 × 10$^3$ |

AlkB Blockades

About 30% of the AlkB-Fe$^{++}$-induced current blockades did not show ligand-induced transitions, suggesting that the trapped enzymes might have a preferred orientation inside the ClyA-AS lumen. An alternative explanation is that sub-populations of AlkB-Fe$^{++}$ might be inactive as a consequence of self-inactivation (Welford, R. W. et al. (2003) *J Biol Chem* 278, 10157-10161), proteolysis, loss of iron, misfolding, etc. AlkB blockades not showing ligand-induced current transitions were ignored and the enzyme was ejected from the pore by reversing the potential to +60 mV. The AlkB-Fe$^{++}$ blockades were nearly eliminated upon addition

TABLE 1

$I_{RES\%}$ values of AlkB—Fe$^{++}$-induced current blockades. All data were collected at −60 mV applied potential in 150 mM NaCl, 15 mM Tris•HCl pH 8.0 at 28° C. Values were calculated from 15 individual AlkB blockades. Errors are given as standard deviations. The ClyA-AS open-pore conductance ($I_o$) was 1.7 ± 0.1 nSi (N = 38 single channels). $\Delta I_{RES\%}$ is the difference between the $I_{RES\%}$ of the AlkB—Fe$^{++}$ protein blockades and the $I_{RES\%}$ induced by the ligand (L1B or L2B).
Proteins and ligands were added to the cis chamber.

|  | No ligand | | 2-OG | | SUC | | N-OG | |
|---|---|---|---|---|---|---|---|---|
|  | L1 $I_{RES\%}$ | L2 $I_{RES\%}$ | L1B $\Delta I_{RES\%}$ | L2B $\Delta I_{RES\%}$ | L1B $\Delta I_{RES\%}$ | L2B $\Delta I_{RES\%}$ | L1B $\Delta I_{RES\%}$ | L2B $\Delta I_{RES\%}$ |
| AlkB—Fe$^{++}$ WT | 52.6 ± 2.0% | 39.0 ± 1.02% | +4.7 ± 1.3% | +1.7 ± 1.2% | +4.6 ± 1.3% | +2.1 ± 1.0% | +4.9 ± 1.0% | +1.7 ± 1.0% |
| AlkB—Fe$^{++}$ N120D | 55.0 ± 1.1% | 39.3 ± 1.24% | / | / | / | / | / | / |

The current enhancements were also observed from the current level L2 (FIG. 6). We hypothesised that such current events reflected the conformational changes occurring during the transition from the open conformation of the apo-enzyme to the closed state of the ligand-bound form of AlkB-Fe$^{++}$ (FIG. 2a) [Bleijlevens, B. et al. (2008) *EMBO rep.* 9, 872-877; Bleijlevens, B. et al. (2012) *Biochem.* 2012, of 40 μM of cognate aptamer (FIG. 8, Table 5), indicating that, as previously reported for other proteins [Soskine (2012) cited above], AlkB-Fe$^{++}$ formed complexes with the aptamer, which cannot be captured by ClyA nanopores as a result of electrostatic repulsion and/or steric hindrance (Franceschini, L. et al. (2013) *Nat. Comm.* 4, 2415). This suggests that the majority of captured AlkB proteins are natively folded, as such aptamer was evolved to bind to folded AlkB (Krylova, S. M. et al. (2011) *Anal Biochem* 414, 261-265).

Example 3

A Reductase as a Protein Adaptor

*E. coli* dihydrofolate reductase (DHFR, Mw=19 kDa) was selected as a second model protein adaptor (FIG. 3a,b). During the DHFR catalytic cycle dihydrofolate is reduced to tetrahydrofolate and the cofactor NADPH is oxidised to NADP+. Tetrahydrofolate is a cofactor in many metabolic reactions, thus inhibitors of DHFR such as methotrexate (MTX) are antibiotic and anticancer agents. The ratio of the NADP+ and NADPH intracellular concentrations is used to monitor the oxidative stress in cells (Ogasawara, Y. et al. (2009) *Biol. & pharmaceut. bull.* 32, 1819-1823). We found that apo-DHFR, which is smaller than AlkB, dwelled inde ClyA-AS only for a few milliseconds. Upon the addition of MTX to the cis solution the frequency and the dwell time of the protein blockades decreased, while the residual current increased. The blockades were then abolished by the subsequent addition of NADPH to the same side (FIG. 11). Since both the inhibitor and the cofactor are negatively charged, these results suggested that the additional negative charges increased the electrophoretic/electrostatic drag force opposing DHFR entry and residence inside the nanopore. In order to increase the residence time of the protein, we engineered DHFR by introducing a polypeptide tag containing four additional positive charges at the C-terminus of the protein ($DHFR_{tag}$, FIG. 10). In complex with MTX, $DHFR_{tag}$ added to the cis compartment, induced current blockades with a mean dwell of 3.1±1.4 s (N=5, $n_p$=230, FIG. 3c) that was three orders of magnitude longer than $DHFR_{tag}$ or DHFR:MTX blockades mean dwell times. A possible explanation to this result is that, tuned by the additional positive charges, the binary $DHFR_{tag}$:MTX complex is at a potential minimum inside the nanopore where the electroosmotic, electrophoretic and electrostatic forces are balanced. The dissociation of MTX from the binary complex was slower than the residence time of the complex inside the nanopore and could not be observed by ionic current recordings. As shown before with apo-AlkB-Fe$^{++}$, $DHFR_{tag}$:MTX blockades showed a main current level L1 ($L1_M$, $I_{RES \%}$=74.7±0.5%, $n_p$=25, N=5) that rarely visited a second current level L2 ($L2_M$, $I_{RES \%}$=53.5±0.9%, $n_p$=25, N=5, FIG. 3c).

At −90 mV the addition of the oxidised cofactor NADP+ to the trans compartment of ClyA-AS produced reversible current enhancements to the $DHFR_{tag}$:MTX complex blockades formed in the cis solution ($L1_{M:N+}$, $\Delta I_{RES \%}$=+2.3±0.5%, $n_p$=15 blockades, $n_f$>225, N=3; and $\tau_{M:N+}$=102±11 ms, $n_f$=19,000, N=9 $n_p$>800, FIG. 4a, Table 3, FIG. 7). Association and dissociation rate constants could be measured from titration experiments (FIG. 4b, Table 4).

NADPH added to the trans compartment also induced additional current enhancements to the binary complex blockades (FIG. 4a). Remarkably, the current events induced by NADPH showed a slightly higher residual current ($L1_{M:NH}$, $\Delta I_{RES \%}$=+2.7±0.7%, $n_p$=15 $n_f$=15, N=4, Table 3) than the NADP+ blockades ($\Delta I_{RES \%}$=+2.3±0.5%) and had a dwell time longer than the residence time of the ternary complex inside the nanopore (FIG. 4a). As a consequence, despite the minute difference between NADPH and NADP+ (a hydride ion), the binding of the two ligands to $DHFR_{tag}$:MTX could be clearly differentiated (FIG. 4a).

TABLE 3

$I_{RES \%}$ values of $DHFR_{tag}$:MTX ligand-induced current blockades. All data were collected at −90 mV applied potential in 150 mM NaCl, 15 mM Tris•HCl pH 7.5 at 28° C. Values were calculated from at least 15 individual $DHFR_{tag}$:MTX blockades. Errors are given as standard deviations. The ClyA-AS open-pore conductance ($I_o$) was 1.6 ± 0.1 nSi (N = 15 single channels). $\Delta I_{RES \%}$ is the difference between the $I_{RES \%}$ of the $DHFR_{tag}$:MTX blockades and the $I_{RES \%}$ induced by the ligand (L1B or L2B). 50 nM of $DHFR_{tag}$ and 400 nM MTX were added to the cis chamber, NADPH and NADP+ were added to the trans chamber.

| | No ligand | | NADP+ | | NADPH | |
|---|---|---|---|---|---|---|
| | L1 $I_{RES \%}$ | L2 $I_{RES \%}$ | L1B $\Delta I_{RES \%}$ | L2B $\Delta I_{RES \%}$ | L2B $\Delta I_{RES \%}$ | L2B $\Delta I_{RES \%}$ |
| $DHFR_{tag}$:MTX | 74.7 ± 0.5% | 53.5 ± 0.9% | +2.3 ± 0.5% | +4.7 ± 0.9% | +2.7 ± 0.7% | +5.4 ± 1.0% |

TABLE 4

Kinetic parameters for ligand binding to $DHFR_{tag}$:MTX. All data were collected in 150 mM NaCl, 15 mM Tris•HCl pH 7.5 at 28° C. Errors are given as standard deviations. 50 nM of $DHFR_{tag}$ and 400 nM MTX were added to the cis chamber, NADPH and NADP+ were added to the trans chamber.

| | NADP+ | NADPH |
|---|---|---|
| $k_{off}^{-90 mV}$ (s$^{-1}$) | 10 ± 1 | NA |
| $k_{on}^{-90 mV}$ (s$^{-1}$ M$^{-1}$) | 2.1 ± 0.3 × 10$^6$ | 4.8 ± 1.2 × 10$^6$ |

Figure 9A:
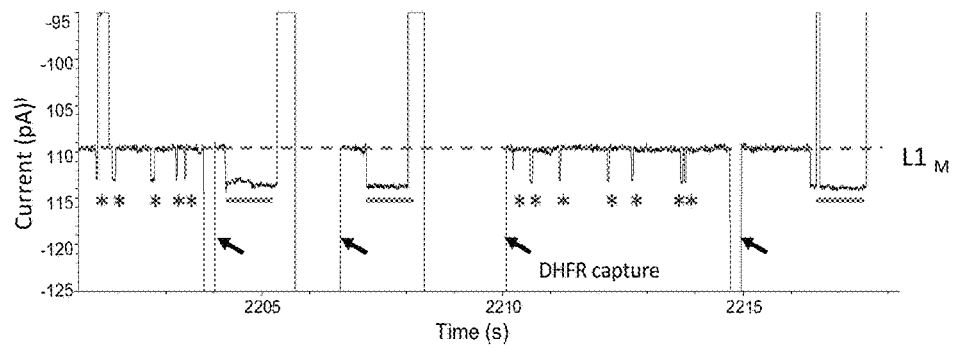
FIGS. 9a-9d show heterogeneity of NADPH and NADP+ binding to DHFR$_{tag}$:MTX.
Figure 9B:
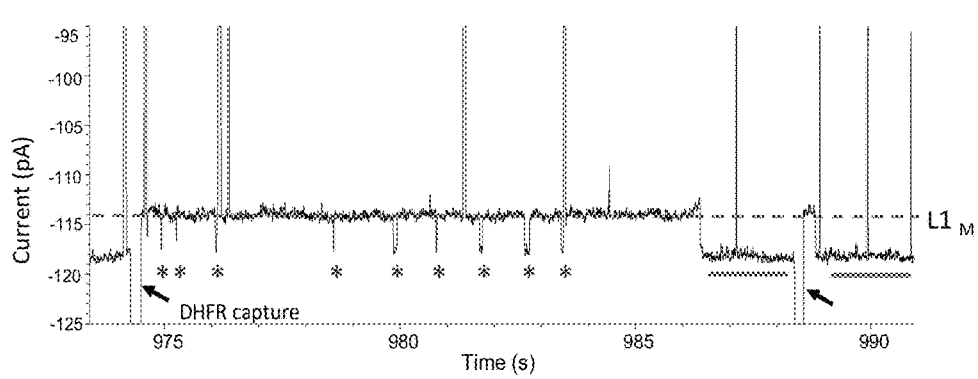
Figure 9C:
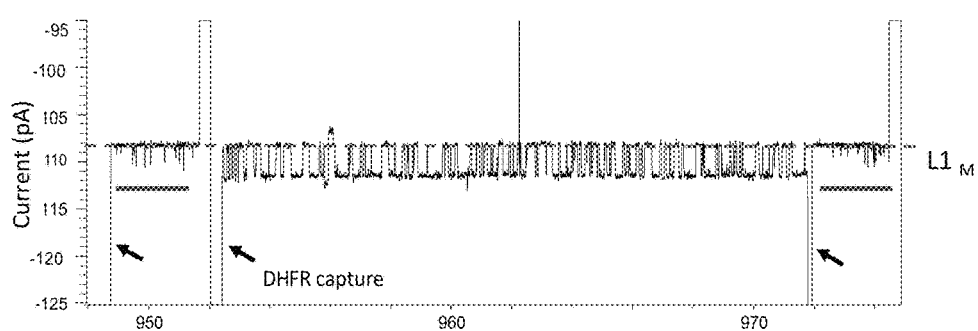
Figure 9D:
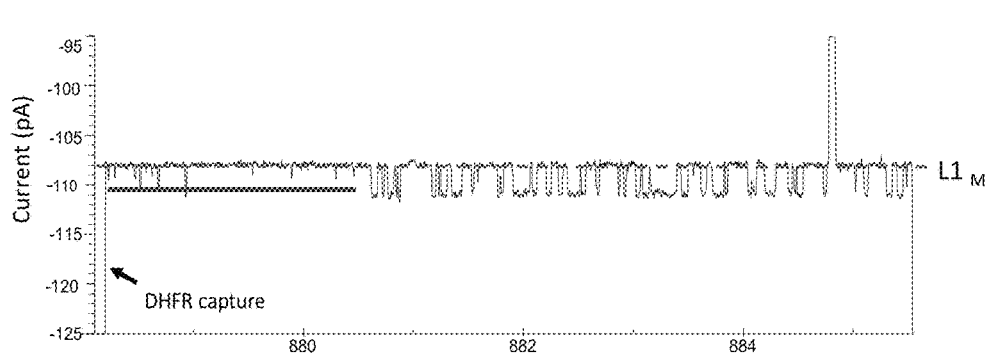

Although the bulk kinetic constants for the binding of NADP+ and NADPH to MTX:DHFR could not be retrieved from the literature, the equilibrium dissociation constant for the binding of 2-OG to AlkB-Mn$^{++}$ was recently measured by an intrinsic tryptophan fluorescence quenching assay ($K_D^{bulk}$=4.1±0.6 10$^{-6}$ M at 24° C.) (Ergel, B. et al. (2014) *J biol chem* 289, 29584-29601). By comparison, the equilibrium dissociation constant of 2-OG for AlkB-Fe$^{++}$ inside the nanopore measured from the ratio of the association and dissociation constants ($K_D^{pore}$=$k_{off}$/$k_{on}$) was about two orders of magnitude higher than the bulk value ($K_D^{pore}$=3.7±1.9 10$^{-4}$ M, −60 mV, 28° C.). This effect is likely to be related to the confinement of AlkB-Fe$^{++}$ inside the nanopore and to the effect of the applied potential. ClyA nanopores have a negatively charged interior and are, therefore, cation selective (Ludwig, A. et al. (1999) *Mol. Microbiol.* 31, 557-567). Thus, under negative applied potentials (trans) the diffusion of the negatively charged ligands added to the cis solution through the nanopore is likely to be opposed. This is probably to be further accentuated by the unfavourable electrostatic interaction between the ligands and the wall of the nanopore lumen. This complication might be overcome by using nanopores with an internal charge with an opposite sign to Heterogeneities in DHFR$_{tag}$:MTX Blockades and NAPDH Binding Events Approximately 45% of the DHFR$_{tag}$:MTX blockades did not respond to the addition of NADP+ (added in trans, FIG. 9c,d). Since all the observed DHFR$_{tag}$ molecules captured by ClyA-AS were bound to MTX, this effect is not likely due to misfolded DHFR molecules. Besides, when NADPH was added to the trans chamber, two distinct populations of DHFR$_{tag}$:MTX blockades were observed: the first (~55% of blockades) gave rise to NADPH binding events with a lifetime longer than the residence time of the complex within ClyA-AS (lifetime >3 seconds, "long" NADPH events), the second population (~45% of blockades) corresponded to DHFR$_{tag}$:MTX blockades that displayed NADPH binding events with a lifetime of 38.5±0.8 ms ("short" NADPH events). Most blockades showed either "long" or "short" NADPH events (FIG. 9a). Rarely, however, the same DHFR$_{tag}$:MTX blockade switched between the two NADPH binding behaviours (FIG. 9b). "Long" and "short" NADPH events showed similar association rate constants ($k_{on}$=4.8±1.2 s$^{-1}$ μM$^{-1}$ and $k_{on}$=5.8±1.2 s$^{-1}$ μM$^{-1}$, respectively) and similar $\Delta I_{RES\ \%}$ values (2.7±0.7% and 2.2±0.9%, respectively, FIG. 9a,b). Although "short" NADPH binding events could arise from NADP+ contaminations, this is unlikely since fresh NADPH aliquots (>95% purity) were used for every experiment. Furthermore, the lifetime of "short" NADPH events was significantly shorter than the lifetime of NADP+ events. In addition, the fact that most of the DHFR$_{tag}$:MTX blockades showed only one binding behaviour, suggests that the observed heterogeneity is not arising from impurities in the substrate samples but from heterogeneity in the protein adaptor (FIG. 9). This variability in binding behaviour could then arise from different configurations of DHFR$_{tag}$:MTX inside the ClyA-AS nanopore and/or from different conformations of the DHFR$_{tag}$:MTX complex. Although the first hypothesis cannot be easily tested, it is interesting to note that previous studies revealed that MTX can bind to two different DHFR conformations with different binding affinities towards NADP+ and NADPH (Rajagopalan, P. T. et al. (2002) *Proc Natl Acad Sci USA* 99, 13481-13486).

Tailoring the DHFR Nanopore Adaptor for Optimal Nanopore Residence

Figures 11A, 11B, 11C, 11D:
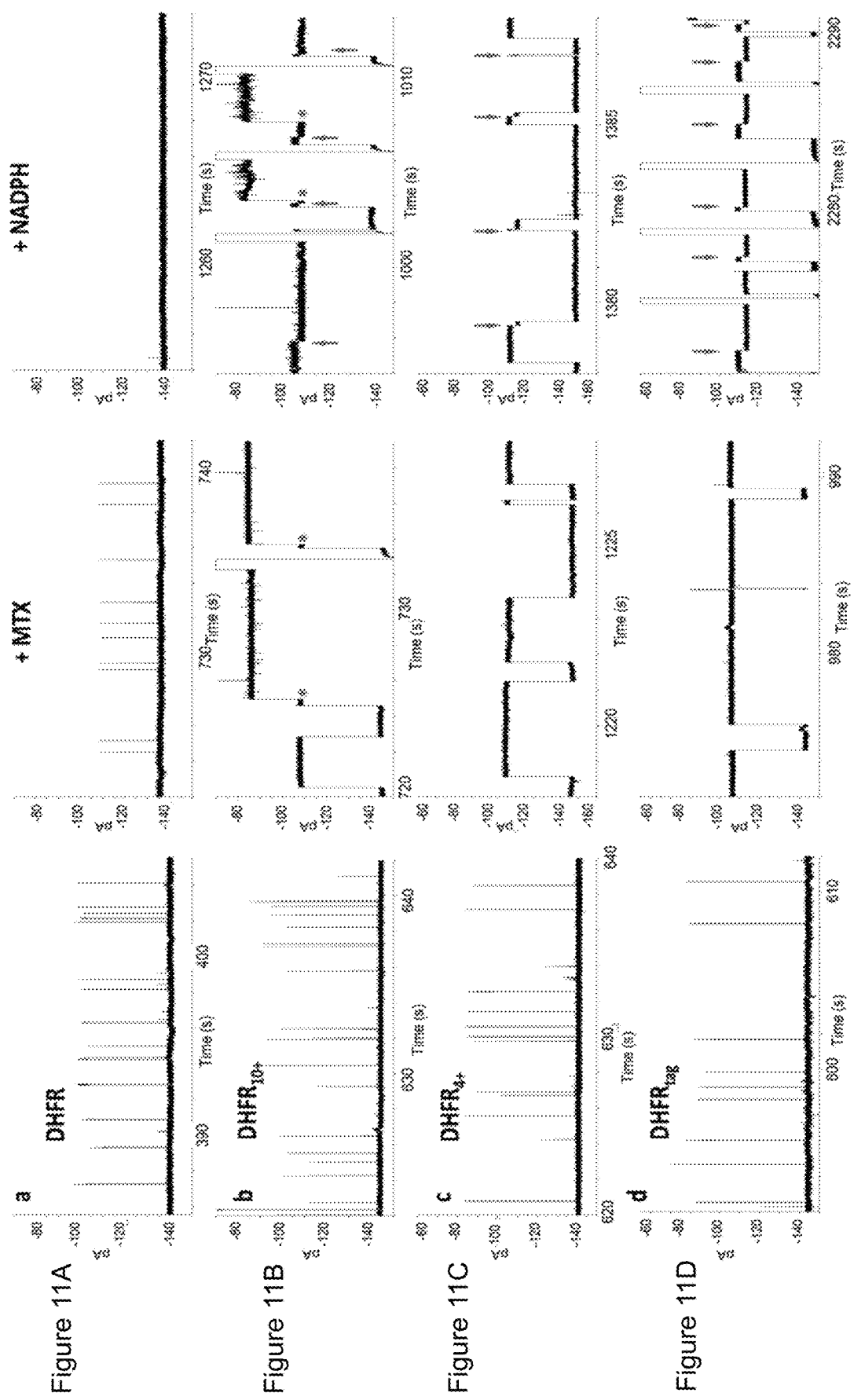
FIGS. 11a-11d show DHFR$_{n+}$, DHFR$_{n+}$:MTX and DHFR$_{n+}$:MTX:NADPH induced current blockades to ClyA-AS nanopores. Representative traces recorded in presence of ~50 nM of FIG. 11a: DHFR.

Our initial DHFR construct consisted of DHFR from *E. coli* with the cysteine residues at positions 85 and 152 substituted with alanine and serine, respectively, and with a C-terminal Strep-tag, inserted for purification purposes, spaced by a 9 amino acid long linker (see later). The fusion tag polypeptide chain contained one additional net positive charge with respect to the wild type sequence (originating from the introduction of a Xho I restriction site in the DNA sequence of the protein). The addition of DHFR (50 nM, FIG. 10) to the cis compartment induced transient blockades to the ClyA-AS open pore current with $I_{RES\ \%}$ of 71.5±0.8% and a lifetime of 21±2 ms (n=200 blockades, N=4 single channels) under −90 mV applied potential (FIG. 11a, left). Subsequent addition of 400 nM of MTX to the cis compartment resulted in blockades with increased $I_{RES\ \%}$ values ($I_{RES\ \%}$=78.4±0.6%) and decreased lifetime (3.3±0.7 ms, n=300 blockades, N=3 single channels, FIG. 11a, centre). Further addition of 20 μM NADPH to the same compartment resulted in the nearly total elimination of the DHFR blockades (FIG. 11a, right), suggesting that the DHFR: MTX:NADPH complex was mostly excluded from the ClyA-AS nanopore. Thus, although we could observe the interaction between the ligands and DHFR, the protein did not remain inside the ClyA-AS nanopore for a time long enough to determine the binding kinetics, prompting us to design DHFR constructs that would have a longer residence time within the ClyA-AS nanopore.

In order to increase the residence time of DHFR into ClyA, we have designed and tested three DHFR constructs that were decorated with a different number of positive charges incorporated into flexible C-terminal fusion tags. We expected the additional charges would prolong the dwell times of the ternary complex within the ClyA-AS nanopore because of the decreased electrostatic repulsion between the negatively charged protein (the pI of DHFR is 4.8) and the negatively charged nanopore lumen (Soskine (2013), cited above), and the reduced electrophoretic drag on DHFR under negative applied potentials. Initially we tested DHFR$_{10+}$, which consisted of the DHFR gene with a C-terminal recombinant tag baring 10 net positive charges with respect to wild type DHFR. The sequence of the 10+ tag comprised of a S-tag (KETAAAKFERQHMDS) (SEQ ID NO:16) derived from pancreatic RNase A, followed by a positively charged coil (KIAALKQKIAALKYKNAALKK-KIAALKQ, adapted from Ref. 40) (SEQ ID NO: 17) (Table 6) and, a Strep-tag for easy purification. DHFR and the three tags were spaced by flexible linkers (FIG. 10). Since we could not predict what would be the effect of the positively charged tag and linker length on the DHFR blockades, we have also designed two constructs with shorter tags and smaller number of additional positive charges: DHFR$_{4+}$ and DHFR$_{tag}$ baring 4 and 5 net positive charges, respectively (FIG. 10).

DHFR$_{10+}$, DHFR$_{4+}$ and DHFR$_{tag}$ induced fast current blockades to ClyA-AS nanopores that converted into second-long blockades upon binding to MTX (FIG. 11). DHFR$_{10+/4+/tag}$:MTX blockades were remarkably longer than DHFR:MTX blockades (e.g. the lifetime of DHFR$_{tag}$: MTX blockades was ~1000 fold that of DHFR:MTX blockades), indicating that the positively charged tags efficiently counterbalanced the electrostatic and electrophoretic effects induced by MTX binding (FIG. 11). Although the blockades induced by the DHFR$_{10+/4+/tag}$:MTX complexes reported the binding of NADPH through ~4 pA enhancements of the residual ionic current (FIG. 11b,c,d, right), DHFR$_{10+}$ and DHFR$_{4+}$ blockades produced non-ideal output signals. The residual current of DHFR$_{10+}$ blockades often switched to a level of lower conductance (FIG. 11b, centre and right), while the binding of NADPH to DHFR$_{4+}$:MTX prompted the quick release of the complex from the pore, indicating that 4 additional positive charges are not enough to keep ternary complex within the pore (FIG. 11c, right). On the other hand, DHFR$_{tag}$:MTX:NADPH was internalised for sufficient time for accurate kinetic analysis and therefore it was chosen for thorough characterization as our nanopore-adaptor.

Example 5

Detection of Analytes with Venus Flytrap Domains

Figure 14:
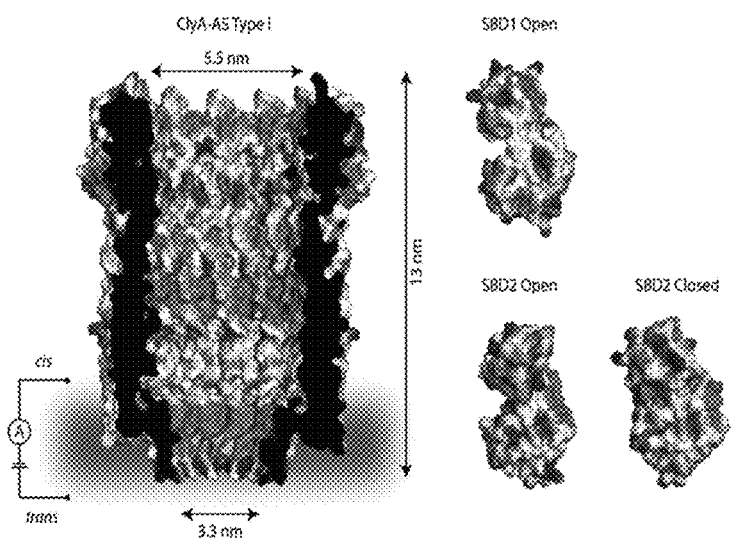
FIG. 14 SBD (substrate-binding domains) proteins with the ClyA nanopore. Left. Type I ClyA-AS nanopore embedded in the lipid bilayer. The dimensions of the ClyA nanopores are indicated considering the van der Waals radii of the atoms. Right. Upper part, surface representation of SBD1 in the open configuration (PDB ID=4LA9). Lower part, surface representation of SBD2 in the open (PDB ID=4KR5) and closed, Gln-bound (PDB ID=4KQP) configuration. The proteins are colored according to their "in vacuum" electrostatics (red for negative regions and blue for positive regions, Pymol).

Venus flytrap domain family of periplasmic binding proteins (PBP) might provide ideal protein adaptors because: 1) they have a domain that has an elongated shape that appears to fit well inside the nanopore and provides a quiet blocked pore signal (FIG. 14). 2) the domain comprises two lobes that upon binding close on the substrate through a large conformational change. 3) Periplasmic binding proteins (PBPs) scavenge or sense diverse nutrients in the environment by coupling to transporters in the inner cell membrane, thus they bind physiologically or technologically relevant substrates with high affinity and selectivity. 4) They bind hundreds of substrates and metabolites (B12 vitamin, many sugars, amino acids, neurotransmitters, etc).

5) Substrate binding appears to be modulated by an 8 residue motif, 15 thus targeted mutations might allow tuning the selectivity for target analytes to the experimental needs.

Results

Sensor for Asparagine

The interaction of SBD1 with asparagine was sampled using type I ClyA-AS nanopores. ClyA-AS (C87A/L99Q/E103G/F166Y/I203V/C285S/K294R/H307Y). In 150 mM NaCl and 15 mM Tris-HCl (pH 7.5), the addition of 74 nM of SBD1 to the cis compartment of Type I ClyA-AS induced transient current blockades at negative applied potentials (trans). At −60 mV the blockades showed one main level (Level I, FIG. 15A,B) with a residual current ($I_{res\ \%}=I_B/I_O \times 100$) of $I_{res\ \%}=67.6\pm0.1\%$ (N=5). Every $3.5\pm0.1$ s$^{-1}$ (mean±S.E., n=212) the current switched to Level II ($I_{res\ \%}=66.8\pm0.4\%$, N=5) with a lifetime of $109\pm1$ ms (mean±S.E., n=340). The protein blockades released spontaneously after $4.2\pm1.8$ s (mean±S.E., n=291). Upon addition of asparagine (concentrations ranging from 200 nM to 4 µM, FIG. 15B), the frequency of the level II increased (FIG. 15B), suggesting that the current blockades are due to the binding of arginine to the SBD1 adaptor inside the nanopore. An inactive SBD1 variant, containing the mutation E184W showed similar blockades to Type I ClyA-AS pores at −60 mV ($I_{res\ \%}=66.7$). However, addition of up to 1 mM asparagine did not show any Level II blockades, indicating that Level II blockades confirming to the asparagine-bound or closed conformation of SBD1.

Figure 15:
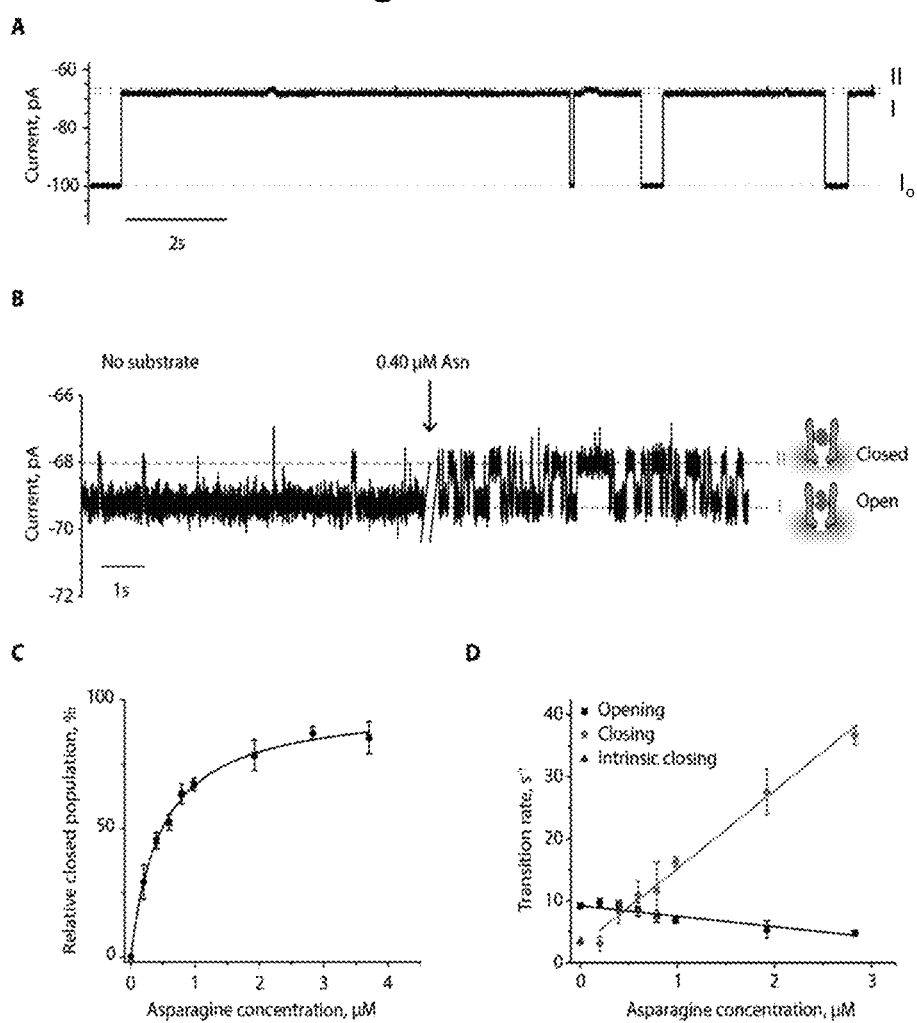
FIG. 15 shows the capture of SBD1 in Type I ClyA-AS Typical ionic current blockades provoked by the capture of SBD1 (substrate-binding domain 1) (74 nM, cis) by the type I ClyA-AS nanopore at −60 mV. The open pore, Level I and Level II current levels are indicated. (B) Detail of SBD1 current blockade before (upper part) and after addition of 0.40 µM asparagine (cis). The current traces were collected in 150 mM NaCl, 15 mM Tris-HCl, pH 7.5 at 24° C. by applying a Bessel low-pass filter with a 2 kHz cutoff and sampled at 10 kHz. A post-acquisition Gaussian filter of 100 Hz was applied. (C) K$_d$ values of SBD1 (74 nM, cis) for asparagine, obtained from the open (Level I) and closed ligand-bound (Level II) populations at the indicated substrate concentrations. Experiments were performed at −60 mV. (D) Opening (k$_{opening}$) and closing (k$_{closing}$) rate constants of SBD1 determined from the transition rates of SBD1 molecules trapped in the nanopore at −60 mV as a function of asparagine concentration. The k$_{closing}$ was obtained from the slope of the linear fit.

The dissociation constant was determined by titrating the substrate and plotting the relative closed population (CL/(O+CL)), determined from the area of the all point current histogram, versus the concentration. Fitting this curve to a one-site binding isotherm gave a $K_d$ value of $0.47\pm0.03$ µM (FIG. 15C), which is in agreement with previously described values obtained by smFRET and isothermal titration calorimetry (ITC) (Gouridis, G. et al. (2015) Nature struct. & mol. biol. 22, 57-64). The closing and opening rate constants were determined from the inverse of the open and closed state lifetimes respectively and were plotted versus the asparagine concentration. The closing rate was linearly dependent on the substrate concentration and the slope of the linear fit gave the $k_{closing}=1.2\times10^7$ s$^{-1}$ M$^{-1}$. The opening rate constant did not show concentration dependency and the value of $k_{opening}$ was determined by the intercept at zero 9.4 s$^{-1}$ (FIG. 15D).

Sensor for Glutamine

The interaction of SBD2 with glutamine was sampled using type I ClyA-AS nanopores at −100 mV. The addition of 72 nM of SBD2 induced a current blockade that fluctuated between two levels I ($I_{res\ \%}=63.6\pm0.3\%$, τ=256±5 ms, N=3) and level III ($I_{res\ \%}=61.0\pm0.2\%$, τ=145±13 ms, N=3). Protein blockades remained inside the nanopore for 3.9±0.7 s (mean±S.E., n=225). Rarely the current visited an additional ionic current level, Level II ($I_{res\ \%}=62.5\pm0.3\%$, τ=18±1 ms, n=856, N=3).

Figure 16:
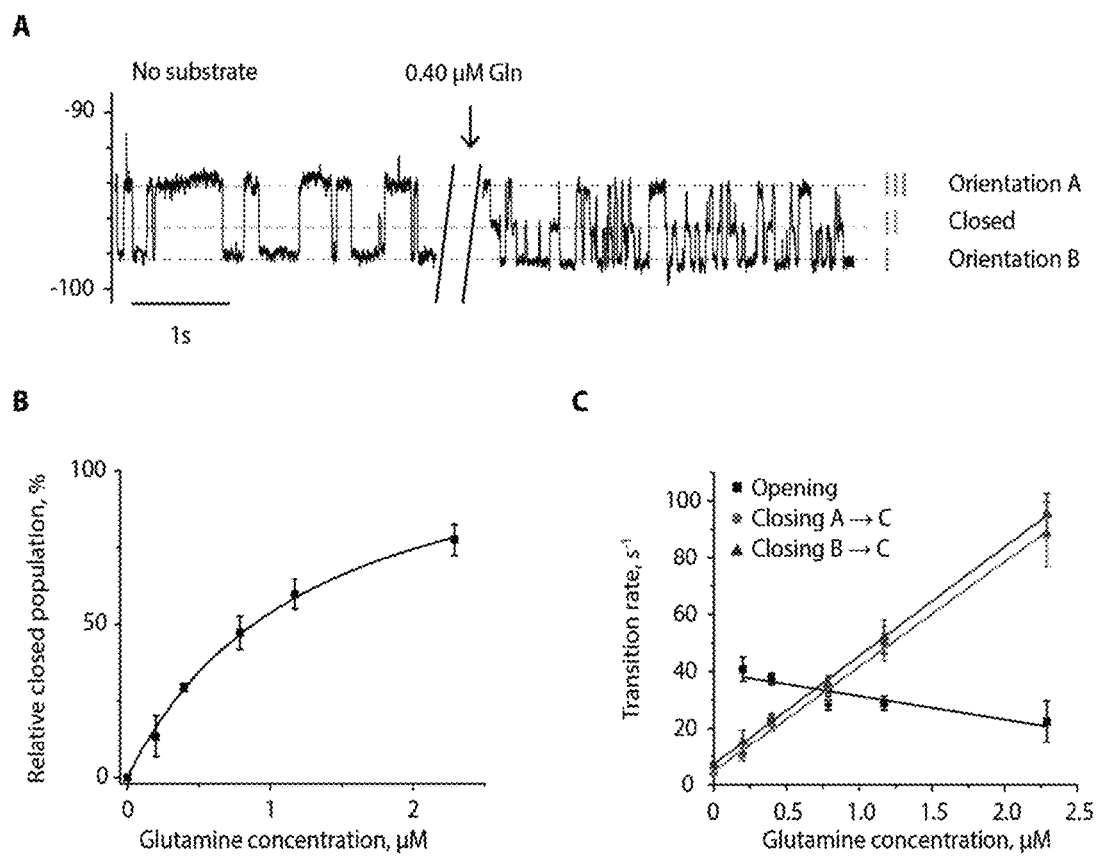
FIG. 16 shows capture of SBD2. Typical current blockade provoked by the capture of SBD2 (70 nM, cis) by the type I ClyA-AS nanopore at −100 mV before (left) and after addition of 0.40 µM glutamine cis. The current traces were collected in 150 mM NaCl, 15 mM Tris-HCl, pH 7.5 at 24° C. by applying a Bessel low-pass filter with a 2 kHz cutoff and sampled at 10 kHz. A post-acquisition Gaussian filter of 100 Hz was applied. (B) K$_d$ values of SBD2 (70 nM, cis) for glutamine, obtained from Level II (bound state), and level I and Level III at the indicated substrate concentrations. Experiments were performed at −100 mV. (C) Opening (k$_{opening}$) and closing (k$_{closing}$) rate constants of SBD2.
Figure 17:
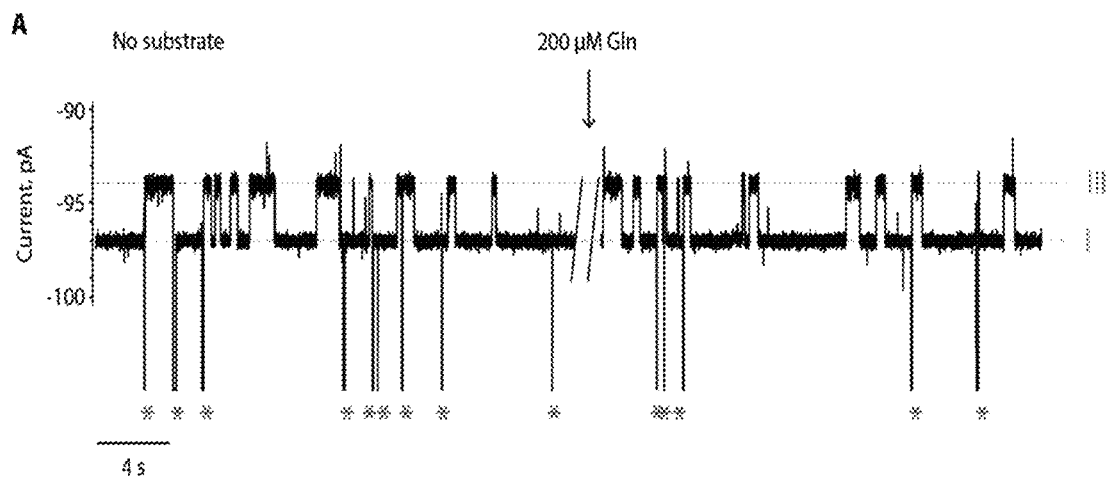
FIG. 17 shows that inactive SBD2 does not bind to glutamine. Typical current blockade provoked by the capture of E417W-SBD2 (cis) by the type I ClyA-AS nanopore at −100 mV before (left) and after addition of 200 µM glutamine cis. Red asteriks represent the restoration of I$_o$ upon the exiting of SBD2_D417F from the pore. Level I and Level II transition most likely represent the entry of SBD2 into ClyA nanopores in two different configurations.

We studied ligand binding by stepwise addition of glutamine at concentrations ranging from 200 nM to 3 µM. After addition of glutamine, the frequency of level II increased linearly with the concentration of glutamine, suggesting this level is the glutamine-bound state. Addition of up to 200 µM glutamine to the SBD2(D417F), a variant that cannot close, did not show any Level II blockades; although conversion between Level I and Level II were still observed (FIG. 17A). These results further suggests that Level II corresponds to the glutamine-bound (FIG. 16A), while the levels I and III might represent different configurations of the protein inside the nanopore. Binding rates were determined from the lifetimes as described above. Upon linear fitting of the binding rate curve the glutamine binding rates from Level I and III were determined. Glutamine binding from Level I showed a nearly identical on rate ($k_{on}=3.7\times10^7$ s$^{-1}$ M$^{-1}$) as binding from Level II ($k_{on}=3.8\times10^7$ s$^{-1}$ M$^{-1}$. FIG. 3C). The opening rate constant was determined by the intercept at zero $k_{off}=39.7$ s$^1$. The obtained $K_d$ value of glutamine binding to SBD2 ($1.27\pm0.14$ µM, FIG. 16B) is in agreement with previously described values obtained by smFRET and ITC (Gouridis, G. et al. (2015) Nature struct. & mol. biol. 22, 57-64).

Glucose Sensor

Figure 18:
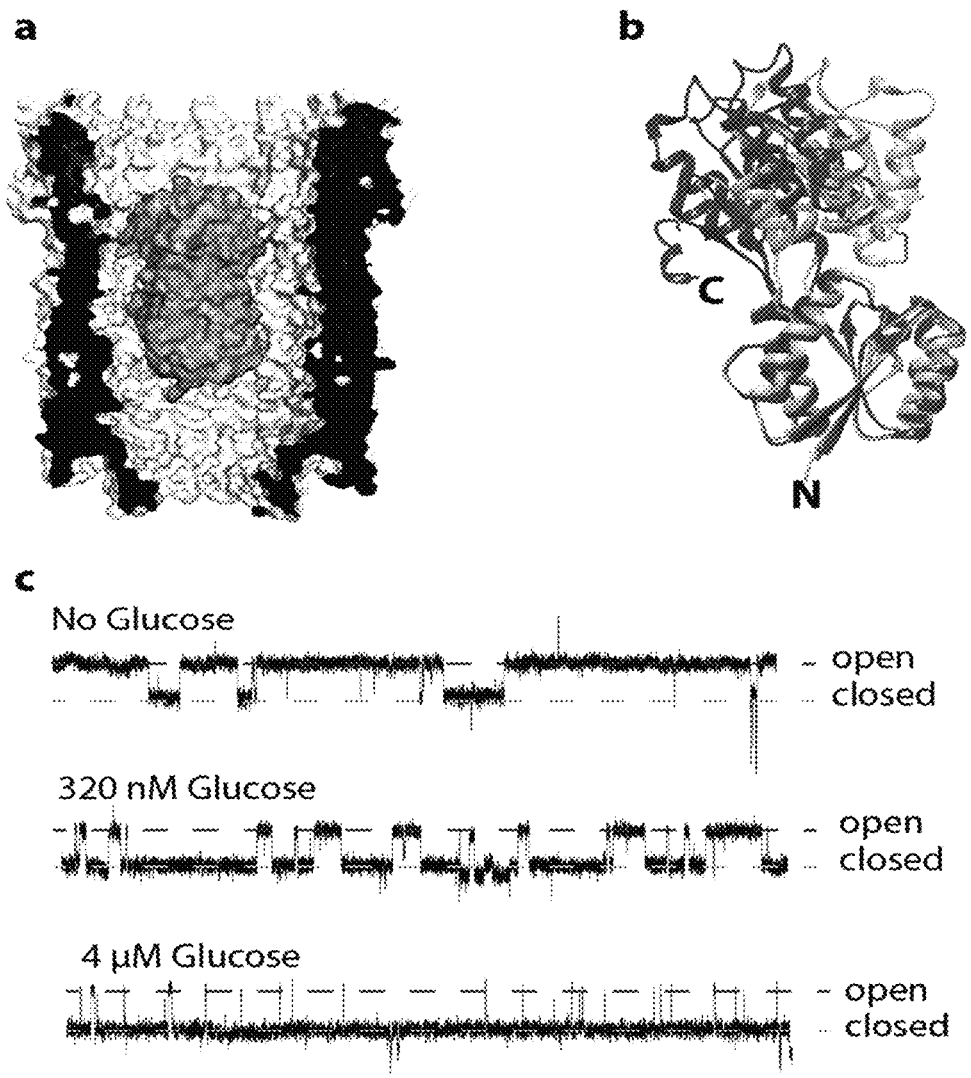
FIG. 18. Glucose sensing with a venus flytrap protein domain. a) Cut-through a ClyA nanopore containing a GBP. b) Cartoon representation of the open (blue) and closed (orange) configuration of the venus flytrap domain of GBP. c) Electrical recording of the GPB blocked current in the absence (top) and presence (middle and bottom) of increasing concentrations of glucose.

Preliminary results showed that the venus flytrap domain of a glucose binding protein (GBP) from E. coli might be a good protein adaptor for a glucose sensor. GBP showed a low background signal (FIG. 18) and an average residence time of ~2 s. Interestingly, in the absence of ligand we observed two current levels, which probably reflected the open and closed conformation of the protein (FIG. 18b-c). The addition of glucose to the cis solution increased the dwell time of one level (presumably the closed state, FIG. 18), suggesting that the conformational changes associated with the binding of ligands to the nanopore can be observed. According to the U.S.FDA recommendations, glucose sensors should detect glucose concentrations between 1.65 and 22 mM (Yoo, E.-H. & Lee, S.-Y. (2010) Sensors 10, 4558-4576). The sensitivity of GBP for glucose is ~1000 fold higher, suggesting that in a few seconds a GBP-based sensor could measure the concentration of glucose in blood. Further, glucose could be also measured in other body fluids such as saliva or sweat, where glucose concentration is much lower (8-210 µM[4] and 0.277-1.11 mM, respectively (Makaram, P. et al. (2014) Diagnostics 4, 27-46; Moyer, J. et al. (2012) Diabetes Technology & Therapeutics 14, 398-402). A device based on GBP would not require 'finger pricking'.

Example 6

Effect of ClyA Mutants on Protein Recognition

Figure 19:
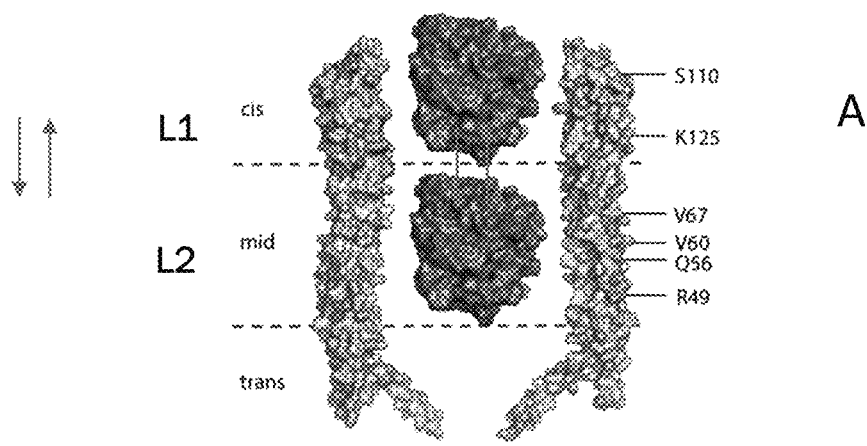
FIG. 19 shows protein recognition with ClyA variants. A). Cut through a ClyA-AS nanopore showing the incorporation of HT. The protein lodges in two sites inside the nanopore which are called L1 and L2. B) Ionic current blockades of HT inside ClyA-AS showing the movement of HT between L1 and L2 at −35 mV. C) Percentage of L1 and L2 residence inside ClyA-AS for different ClyA-AS mutants.
Figure 19:
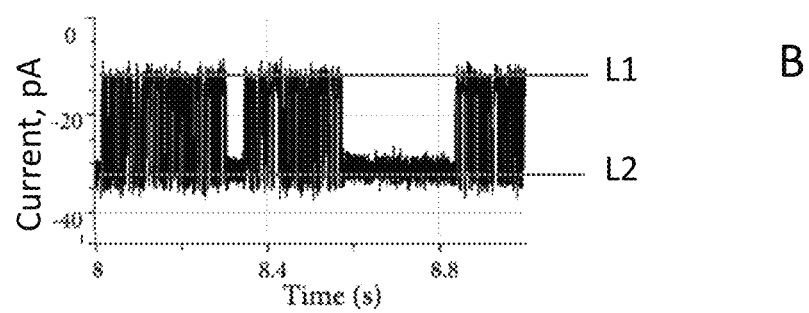
Figure 19:
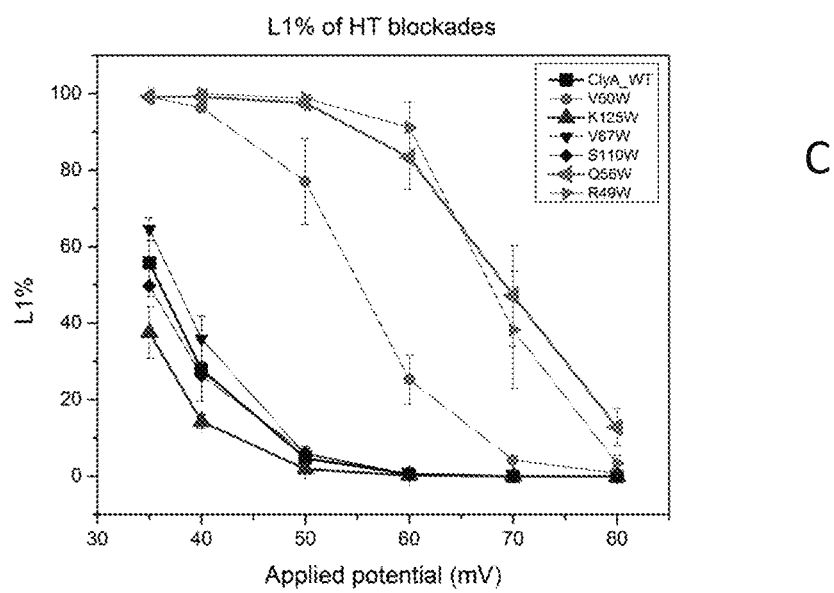

Several mutations inside the C1YA-AS nanopore (FIG. 19) were tested to find out which location within the nanopore allows better recognition. As a model system we used human thrombin (HT). When added on the cis side of the nanopore, HT enters the pore and switches between L1 and L2 binding sites (FIG. 19B). At high applied potential L2 is populated more than L1 (FIG. 19c). To test the recognition point in ClyA-AS, we substituted a tryptophan residue (W) to several position inside the nanopore (FIG. 19A). The occupancy of L1 and L2 at different potentials depended on the mutant tested (FIG. 19C). Substitutions at position 49, 56 and 60 had the strongest effect, revealing the potential binding site for HT inside the nanopore.

Figure 20:
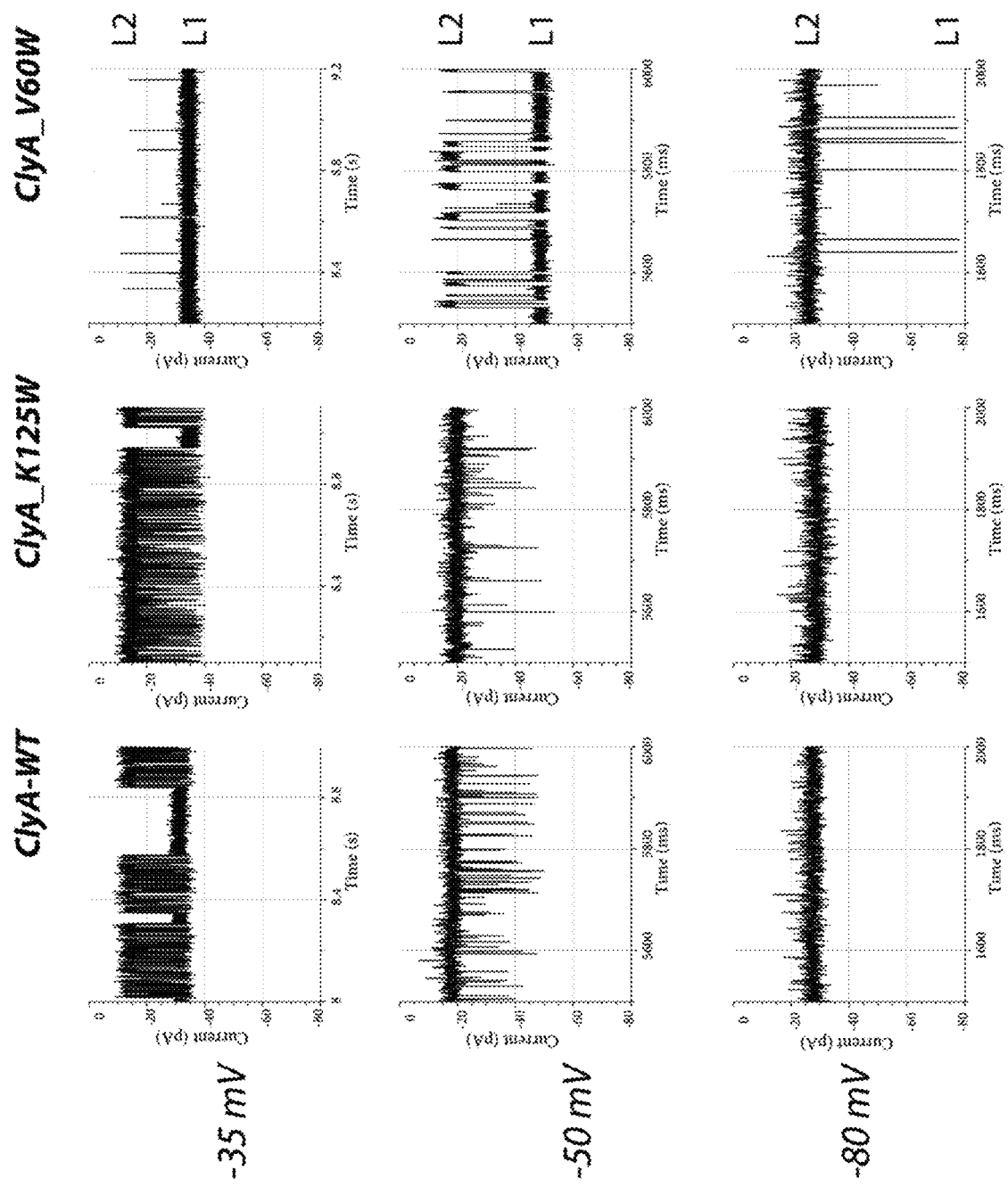
FIG. 20 Shows the effect of nanopore mutations on Human thrombin blockades. The figure indicate the blockades induced by human thrombin at −35, −50 and −80 mV (from top to bottom) to ClyA-AS-WT, CLyA-AS-125W and ClyA-AS-v60w (from left to right). THe blockades induced by human thrombin are similar for ClyA-AS-WT and CLyA-AS-125W, and differ for ClyA-AS-v60w, indicating that thrombin binding site is close to the position 60 inside the ClyA nanopore.
Figure 21:
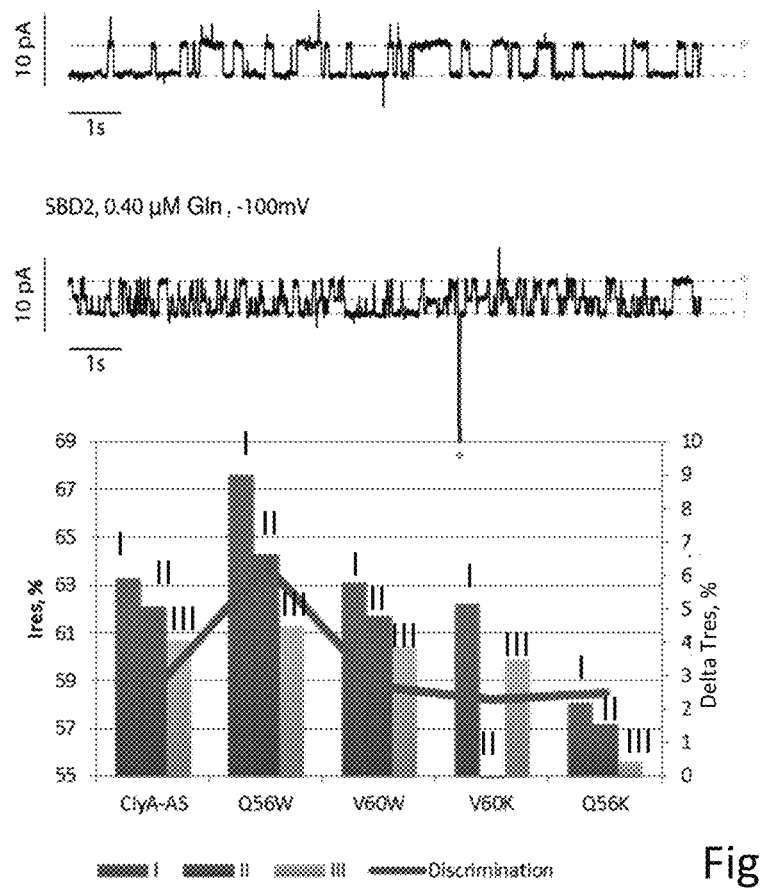
FIG. 21 shows analyte recognition with ClyA nanopores. A). Binding of Glutamine to SBD2 inside a ClyA-AS nanopore. Level I and Level III correspond to the open SBD2 configuration (see word file), while Level II corresponds to the ligand bound configuration.
B). mutant screened showing the difference between level I, Level II and Level III (as residual current %). Q56W provides the better recognition.
Figure 22:
FIG. 22 shows SBD2 blockades to ClyA-AS-q56w. The signal due to the binding of glutamine to the internalized adaptor (level L2) is enhanced when compared to the signal measured for the ClyA-WT pore (FIG. 21)
Figure 22:
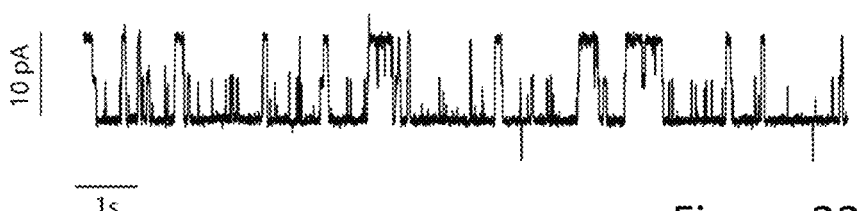

In addition the binding of analytes to a protein lodged inside the nanopore was tested (FIG. 20A, SBD2).

We found that the recognition of the substrate is enhanced by placing a tryptophan residue at position 56. Lysine residues at position 56 or 60 reduced recognition.

Example 7

Primer and Aptamer Sequences Disclosed in the Invention

| Primer name | Sequence | SEQ ID NO |
|---|---|---|
| fAlkB | AGATATAGCCATGGCGTTGGATCTGTTTGCCGATGCTGAAC | SEQ ID NO: 22 |
| AlkBr1 | CGGATGGCTCCACGCGCTGCCTTCTTTTTTACCTGCCTGACGGAATG | SEQ ID NO: 23 |
| AlkBr2 | TATATATAAGCTTATCATTTTTCAAACTGCGGATGGCTCCACGCGCTGCC | SEQ ID NO: 24 |
| 120D | GCCAGATGCTTGTCTTATCAACCGCTACGCTCCTGGCGCGAAACTGTCGC | SEQ ID NO: 25 |
| T7-terminator | GCTAGTTATTGCTCAGCGG | SEQ ID NO: 26 |
| Anti-AlkB aptamer | TGCCTAGCGTTTCATTGTCCCTTCTTATTAGGTGATAATA | SEQ ID NO: 27 |
| DHf | atatatatCCATGGCTTCGGCTATGATTTCTCTGATTGCG | SEQ ID NO: 28 |
| DHr | CGCGGTTTCTTTCGCTCGAGTACTGCTGCCacggcgttccaggatttcgaatgag | SEQ ID NO: 29 |
| Cof | ctcattcgaaatcctggaacgccgtGGCAGCAGTACTCGAGCGAAAGAAACCGCG | SEQ ID NO: 30 |
| Cor | atatatatAAGCTTATCATTTTTCAAACTGCGGATGGC | SEQ ID NO: 31 |
| dcr | atatatatCTCGAGTACTGCTGCCACGGCGTTCCAGGATTTCG | SEQ ID NO: 32 |
| delF | atatatatCTCGAgcgggcAGCGCGTGGAGCCATCCGCAGTTTG | SEQ ID NO: 33 |
| 2dcF | atatatatCTCGAGCGaagaagattgcggccctaaaacaggg | SEQ ID NO: 34 |
| dcf | atatatatCTCGAGCGaaaaagaagattgcggccctaaaacaggg | SEQ ID NO: 35 |

| Description | Sequence |
|---|---|
| Protein sequence for *S. typhi* ClyA (ClyA-WT) SEQ ID NO: 1 | MTGIFAEQTVEVVKSAIETADGALDLYNKYLDQVIPWKTFDETIKELSRFKQEYSQEASVLVGDIKVLLMDSQDKYFEATQTVYEWCGVVTQLLSAYILLFDEYNEKKASAQKDILIRILDDGVKKLNEAQKSLLTSSQSFNNASGKLLALDSQLTNDFSEKSSYFQSQVDRIRKEAYAGAAAGIVAGPFGLIISYSIAAGVIEGKLIPELNNRLKTVQNFFTSLSATVKQANKDIDAAKLKLATEIAAIGEIKTETETTRFYVDYDDLMLSLLKGAAKKMINTCNEYQQRHGKKTLFEVPDV |
| Protein sequence for ClyA with C285S substitution (ClyA-CS) SEQ ID NO: 2 | MTGIFAEQTVEVVKSAIETADGALDLYNKYLDQVIPWKTFDETIKELSRFKQEYSQEASVLVGDIKVLLMDSQDKYFEATQTVYEWCGVVTQLLSAYIQLFDGYNEKKASAQKDILIRILDDGVKKLNEAQKSLLTSSQSFNNASGKLLALDSQLTNDFSEKSSYYQSQVDRIRKEAYAGAAAGIVAGPFGLIISYSIAAGVIEGKLIPELNNRLKTVQNFFTSLSATVKQANKDIDAAKLKLATEIAAIGEIKTETETTRFYVDYDDLMLSLLKGAAKKMINTSNEYQQRHGRKTLFEVPDVGSSHhhhHHHHH* |
| Protein sequence for ClyA-AS SEQ ID NO :3 | MTGIFAEQTVEVVKSAIETADGALDLYNKYLDQVIPWKTFDETIKELSRFKQEYSQEASVLVGDIKVLLMDSQDKYFEATQTVYEWAGVVTQLLSAYIQLFDGYNEKKASAQKDILIRILDDGVKKLNEAQKSLLTSSQSFNNASGKLLALDSQLTNDFSEKSSYYQSQVDRIRKEAYAGAAAGIVAGPFGLIISYSIAAGVVEGKLIPELNNRLKTVQNFFTSLSATVKQANKDIDAAKLKLATEIAAIGEIKTETETTRFYVDYDDLMLSLLKGAAKKMINTSNEYQQRHGRKTLFEVPDVGSSYHHHHH* |

| Description | Sequence |
|---|---|
| Nucleotide sequence for *S. typhi* ClyA SEQ ID NO: 4 | CCTGCGTAGATAAGCAGGAAGCAGGCAGTATTTCCAGCT<br>TCTGGAATGTTAAAGCTACAAAAGTTGTCTGGAGGTAAT<br>AGGTAAGAATACTTTATAAAACAGGTACTTAATTGCAAT<br>TTATATATTTAAAGAGGCAAATGATTATGACCGGAATAT<br>TTGCAGAACAAACTGTAGAGGTAGTTAAAAGCGCGATC<br>GAAACCGCAGATGGGGCATTAGATCTTTATAACAAATAC<br>CTCGACCAGGTCATCCCCTGGAAGACCTTTGATGAAACC<br>ATAAAAGAGTTAAGCCGTTTTAAACAGGAGTACTCGCAG<br>GAAGCTTCTGTTTTAGTTGGTGATATTAAAGTTTTGCTTA<br>TGGACAGCCAGGACAAGTATTTTGAAGCGACACAAACT<br>GTTTATGAATGGTGTGGTGTCGTGACGCAATTACTCTCA<br>GCGTATATTTTACTATTTGATGAATATAATGAGAAAAAA<br>GCATCAGCCCAGAAAGACATTCTCATTAGGATATTAGAT<br>GATGGTGTCAAGAAACTGAATGAAGCGCAAAAATCTCT<br>CCTGACAAGTTCACAAAGTTTCAACAACGCTTCCGGAAA<br>ACTGCTGGCATTAGATAGCCAGTTAACTAATGATTTTTC<br>GGAAAAAAGTAGTTATTTCCAGTCACAGGTGGATAGAAT<br>TCGTAAGGAAGCTTATGCCGGTGCTGCAGCCGGCATAGT<br>CGCCGGTCCGTTTGGATTAATTATTTCCTATTCTATTGCT<br>GCGGGCGTGATTGAAGGGAAATTGATTCCAGAATTGAAT<br>AACAGGCTAAAAACAGTGCAAATTTCTTTACTAGCTTA<br>TCAGCTACAGTGAAACAAGCGAATAAAGATATCGATGC<br>GGCAAAATTGAAATTAGCCACTGAAATAGCAGCAATTG<br>GGGAGATAAAAACGGAAACCGAAACAACCAGATTCTAC<br>GTTGATTATGATGATTTAATGCTTTCTTTATTAAAAGGAG<br>CTGCAAAGAAAATGATTAACACCTGTAATGAATACCAAC<br>AAAGACACGGTAAGAAGACGCTTTTCGAGGTTCCTGACG<br>TCTGATACATTTTCATTCGATCTGTGTACTTTTAACGCCC<br>GATAGCGTAAAGAAAATGAGAGACGGAGAAAAAGCGAT<br>ATTCAACAGCCCGATAAACAAGAGTCGTTACCGGGCTGA<br>CGAGGTTATCAGGCGTTAAGCTGGTAG |
| Nucleotide sequence for ClyA with C285S substitution (ClyA-CS) SEQ ID NO: 5 | ATGACGGGTATCTTTGCGGAACAGACGGTGGAAGTTGTG<br>AAAAGTGCGATTGAAACGGCTGACGGTGCGCTGGACCT<br>GTATAATAAATATCTGGATCAGGTCATCCCGTGGAAAAC<br>CTTTGACGAAACGATTAAAGAACTGAGCCGTTTCAAACA<br>GGAATACAGTCAAGAAGCGTCCGTCCTGGTGGGCGATAT<br>CAAAGTGCTGCTGATGGATTCTCAGGACAAATATTTTGA<br>AGCTACCCAAACGGTTTACGAATGGTGTGGTGTGGTTAC<br>CCAGCTGCTGTCCGCATATATTCAGCTGTTCGATGGATA<br>CAACGAGAAAAAAGCGAGCGCGCAGAAAGACATTCTGA<br>TCCGCATTCTGGATGACGGCGTGAAAAAACTGAATGAA<br>GCCCAGAAATCGCTGCTGACCAGCTCTCAATCATTTAAC<br>AATGCCTCGGGTAAACTGCTGGCACTGGATAGCCAGCTG<br>ACGAACGACTTTTCTGAAAAAAGTTCCTATTACCAGAGC<br>CAAGTCGATCGTATTCGTAAAGAAGCCTACGCAGGTGCC<br>GCAGCAGGTATTGTGGCCGGTCCGTTCGGTCTGATTATC<br>TCATATTCGATTGCTGCGGGCGTTATCGAAGGTAAACTG<br>ATTCCGGAACTGAACAATCGTCTGAAAACCGTTCAGAAC<br>TTTTTCACCAGTCTGTCTGCTACGGTCAAACAAGCGAAT<br>AAAGATATCGACGCCGCAAAACTGAAACTGGCCACGGA<br>AATCGCTGCGATTGGCGAAATCAAAACCGAAACGGAAA<br>CCACGCGCTTTTATGTTGATTACGATGACCTGATGCTGA<br>GCCTGCTGAAAGGTGCCGCGAAGAAAATGATTAATACCT<br>CTAATGAATATCAGCAGCGTCACGGTAGAAAAACCCTGT<br>TTGAAGTCCCGGATGTGGGCAGCAGCCACCACCATCATC<br>ACCACTAAAAGCTTGGATCCGGCTGCTAACAAAGCCCGA<br>A |
| Nucleotide sequence for ClyA-AS SEQ ID NO: 6 | ATGACGGGTATCTTTGCGGAACAGACGGTGGAAGTTGTG<br>AAAAGTGCGATTGAAACGGCTGACGGTGCGCTGGACCT<br>GTATAATAAATATCTGGATCAGGTCATCCCGTGGAAAAC<br>CTTTGACGAAACGATTAAAGAACTGAGCCGTTTCAAACA<br>GGAATACAGTCAAGAAGCGTCCGTCCTAGTGGGCGATAT<br>CAAAGTGCTGCTGATGGATTCTCAGGACAAATATTTTGA<br>AGCTACCCAAACGGTTTACGAATGGGCGGGTGTGGTTAC<br>CCAGCTGCTGTCCGCATATATTCAGCTGTTCGATGGATA<br>CAATGAGAAAAAAGCGAGCGCGCAGAAAGACATTCTGA<br>TCCGCATTCTGGATGACGGCGTGAAAAAACTGAATGAA<br>GCCCAGAAATCGCTGCTGACCAGCTCTCAATCATTTAAC<br>AATGCCTCGGGTAAACTGCTGGCACTGGATAGCCAGCTG<br>ACGAACGACTTTTCTGAAAAAAGTTCCTATTACCAGAGC<br>CAAGTCGATCGTATTCGTAAAGAAGCCTACGCAGGTGCC<br>GCAGCAGGTATTGTGGCCGGTCCGTTCGGTCTGATTATC<br>TCATATTCAATTGCTGCGGGCGTTGTCGAAGGTAAACTG<br>ATTCCGGAACTGAACAATCGTCTGAAAACCGTTCAGAAC |

| Description | Sequence |
|---|---|
| | TTTTTCACCAGTCTGTCTGCTACGGTCAAACAAGCGAAT<br>AAAGATATCGACGCCGCAAAACTGAAACTGGCCACGGA<br>AATCGCTGCGATTGGCGAAATCAAAACCGAAACGGAAA<br>CCACGCGCTTTTATGTTGATTACGATGACCTGATGCTGA<br>GCCTGCTGAAAGGTGCCGCGAAGAAAATGATTAATACCT<br>CTAATGAATATCAGCAGCGTCACGGTAGAAAAACCCTGT<br>TTGAAGTCCCGGATGTGGGCAGCAGCTACCACCATCATC<br>ACCACTAAAAGCTT |
| AlkB-streptag<br>(protein<br>sequence,<br>additional amino<br>acid residues are<br>underlined)<br>SEQ ID NO: 7 | <u>MA</u>LDLFADAEPWQEPLAAGAVILRRFAFNAAEQLIRDIND<br>VASQSPFRQMVTPGGYTMSVAMTNCGHLGWTTHRQGYL<br>YSPIDPQTNKPWPAMPQ SFHNLCQRAATAAGYPDFQPDAC<br>LINRYAPGAKLSLHQDKDEPDLRAPIVSVSLGLPAIFQFGGL<br>KRNDPLKRLLLEHGDVVVWGGESRLFYHGIQPLKAGFHPL<br>TIDCRYNLTFRQAGKKE<u>GSAWSHPQFEK</u>** |
| >AlkB-streptag<br>(DNA sequence)<br>SEQ ID NO: 8 | Atggcgttggatctgtttgccgatgctgaaccgtggcaagagccactggcggctggtgcggt<br>aattttacggcgttttgctttaacgctgcggagcaactgatccgcgatattaatgacgttgccag<br>ccagtcgccgtttcgccagatggtcaccccggggatataccatgtcggtggcgatgacca<br>actgtgggcatctgggctggacgacccatcggcaaggttatctctattcgcccattgatccgca<br>aacaaataaaccgtggcccgccatgccacagagttttcataatttatgtcaacgtgcggctacg<br>gcggcgggctatccagatttccagccagatgcttgtcttatcaaccgctacgctcctggcgcg<br>aaactgtcgctgcatcaggataaagacgaaccggatctgcgcgcgccaattgttctgtttctct<br>gggcttacccgcgattttcaatttggcggcctgaaacgaaatgatccgctcaaacgtttgttgtt<br>ggaacatggcgatgtggtggtatggggcggtgaatcgcggctgttttatcacggtattcaacc<br>gttgaaagcggggtttcatccactcaccatcgactgccgctacaacctgacattccgtcaggc<br>aggtaaaaaagaaggcagcgcgtggagccatccgcagtttgaaaaatgatAAGCTT |
| > DHFR<sub>10+</sub><br>(DNA sequence)<br>SEQ ID NO :9 | Atggcttcggctatgatttctctgattgcgcactggctgtcgatcgtgttattggatggaaaac<br>gctatgccgtggaatctgccggctgatctggcgtggtttaaacgtaacactctggacaagccg<br>gtcattatgggccgccatacgtgggaaagcatcggtcgtccgctgccgggtcgcaaaaatatt<br>atcctgagcagccagccgggcaccgatgaccgtgtgacgtgggttaagagcgtcgatgaag<br>caattgcggcggcaggcgacgtgccggaaattatggttatcggcggtggccgcgtttatgaa<br>cagttcctgccgaaagcccaaaagctgtacctgacccatatcgatgcagaagtcgaaggtgat<br>acgcactttccggactatgaaccggatgactgggaaagtgtgttctccgaatttcacgacgcc<br>gacgctcagaacagccactcatactcattcgaaatcctggaacgccgtGGCAGCAGT<br>ACTCGAGCGAAAGAAACCGCGGCGGCGAAATTTGAACG<br>CCAGCATATGGATAGCGGCAGCGCGAAAATTGCCGCAC<br>TTAAACAAAAAATCGCGGCGCTGAAGTATAAAAATGCG<br>GCACTAAAAAAGAAGATTGCGGCCCTAAAACAGGGCAG<br>CGCGTGGAGCCATCCGCAGTTTGAAAAATGATAAGCTTG<br>GA |
| > DHFR<sub>10+</sub><br>(protein<br>sequence,<br>additional amino<br>acid residues are<br>underlined)<br>SEQ ID NO: 10 | <u>MASAM</u>ISLIAALAVDRVIGMENAMPWNLPADLAWFKRNT<br>LDKPVIMGRHTWESIGRPLPGRKNIILSSQPGTDDRVTWVK<br>SVDEAIAAAGDVPEIMVIGGGRVYEQFLPKAQKLYLTHIDA<br>EVEGDTHFPDYEPDDWESVFSEFHDADAQNSHSYSFEILER<br>R<u>GSSTRAKETAAAKFERQHMDSGSAKIAALKQKIAALKYK</u><br><u>NAALKKKIAALKQGSAWSHPQFEK</u>** |
| DHFR10+<br>SEQ ID NO: 11 | ERRGSSTRAKETAAAKFERQHMDSGSAKIAALKQKIAALK<br>YKNAALKKKIAALKQGSAWSHPQFEK |
| DHFRtag<br>SEQ ID NO: 12 | ERRGSSTRAKKKIAALKQGSAWSHPQFEK |
| DHFR4+<br>SEQ ID NO: 13 | ERRGSSTRAKKIAALKQGSAWSHPQFEK |
| DHFR<br>SEQ ID NO: 14 | ERRGSSTRAGSAWSHPQFEK |
| C-terminus of<br>DHFR | ERR |
| S-tag<br>SEQ ID NO: 16 | KETAAAKFERQHMDS |
| Positive coil<br>SEQ ID NO: 17 | KIAALKQKIAALKYKNAALKKKIAALKQ |
| Strep-tag<br>SEQ ID NO: 18 | WSHPQFEK |

| Description | Sequence |
|---|---|
| Flexible linker 1 SEQ ID NO: 19 | GSSTRA |
| Flexible linker 2 SEQ ID NO: 20 | GSA |
| Flexible linker 3 SEQ ID NO: 21 | GSSTRAGSA |

The invention claimed is:

1. A method for detecting an analyte in a sample, comprising the steps of:
   a) obtaining a complex comprising:
      (i) a protein nanopore comprising a subunit having a sequence that is at least 80% identical to the sequence set forth in SEQ ID NO: 1, wherein the nanopore comprises a cis side and a trans side connected by a lumen having a cis-diameter and a trans-diameter; and
      (ii) a globular enzyme protein adaptor,
      wherein the globular enzyme protein adaptor is smaller than the cis-diameter of the nanopore but larger than the trans-diameter of the nanopore or the globular enzyme protein adaptor is smaller than the trans-diameter of the nanopore but larger than the cis-diameter of the nanopore and retains its binding function,
      wherein the globular enzyme protein adaptor is selected from the group consisting of an oxidoreducase, a transferase, an hydrolase, a lyase, an isomerase, a ligase, a demethylase, a reductase, and thrombin, and
      wherein the globular enzyme protein adaptor is internalized within the lumen of the nanopore such that the protein adaptor is not covalently bound to the nanopore,
   b) contacting the complex with a sample comprising an analyte, wherein the contacting occurs on the cis side or the trans side of the nanopore, and
   c) measuring conductance across the nanopore, wherein a change in the conductance after addition of the sample indicates the binding of the analyte to the internalized globular enzyme protein adaptor and the presence of the analyte in the sample.

2. The method according to claim 1, wherein the subunit comprises a Trp substitution at an amino acid position corresponding to Gln56 of SEQ ID NO: 1.

3. The method according to claim 1, wherein the nanopore comprises a plurality of subunits, each subunit comprising an amino acid sequence represented by SEQ ID NO: 3.

4. The method according to claim 1, wherein the globular enzyme protein adaptor is a demethylase enzyme or a reductase enzyme.

5. The method according to claim 4, wherein the demethylase is AlkB demethylase.

6. The method according to claim 5, wherein the demethylase is AlkB demethylase comprising an Asn120Asp mutation.

7. The method according to claim 4, wherein the reductase is dihydrofolate reductase.

8. The method according to claim 1, wherein the globular enzyme protein adaptor comprises a tag, wherein the tag has a net overall positive or net overall negative charge.

9. The method according to claim 1, wherein the protein adaptor forms a complex with one or more additional molecules.

10. The method according to claim 1, wherein the analyte is a small molecule, a protein, or a nucleic acid.

11. The method according to claim 1, wherein the analyte is charged.

12. The method according to claim 1, wherein in the globular enzyme protein adaptor is smaller than the cis-diameter of the nanopore but larger than the trans-diameter of the nanopore, the cis-diameter of the nanopore is 4.5 to 7 nm, and the trans-diameter of the nanopore is 1.5 nm to 4.0 nm; and in b), the contacting occurs on the cis side of the nanopore.

13. The method according to claim 1, wherein the globular enzyme protein adaptor is classified under Enzyme Commission (EC) Number: EC1, EC2, EC3, EC4, EC5, or EC6.

14. The method according to claim 1, wherein the subunit comprises a Ser substitution at an amino acid position corresponding to Cys 87 or Cys 285 of SEQ ID NO: 1.

15. The method according to claim 1, wherein the subunit comprises:
   a) a Gln substitution at an amino acid position corresponding to L99 in SEQ ID NO: 1;
   b) a Gly substitution at an amino acid position corresponding to E103 in SEQ ID NO: 1;
   c) a Tyr substitution at an amino acid corresponding to F166 in SEQ ID NO: 1; and/or
   d) an Arg substitution at an amino acid corresponding to K294 in SEQ ID NO: 1.

16. A method for detecting an analyte in a sample, comprising the steps of:
   a) obtaining a complex comprising:
      (i) a protein nanopore comprising a subunit having a sequence that is at least 80% identical to the sequence set forth in SEQ ID NO: 1, wherein the nanopore comprises a cis side and a trans side connected by a lumen having a cis-diameter and a trans-diameter; and
      (ii) a protein adaptor selected from the group consisting of SBD1, SBD2, and glucose binding protein (GBP), wherein the protein adaptor is smaller than the cis-diameter of the nanopore but larger than the trans-diameter of the nanopore or the protein adaptor is smaller than the trans-diameter of the nanopore but larger than the cis-diameter of the nanopore and retains its binding function, and wherein the protein adaptor is internalized within the lumen of the nanopore such that the protein adaptor is not covalently bound to the nanopore,
   b) contacting the complex with a sample comprising an analyte, wherein the contacting occurs on the cis side or the trans side of the nanopore, and
   c) measuring conductance across the nanopore, wherein a change in the conductance after addition of the sample indicates the binding of the analyte to the internalized protein adaptor and the presence of the analyte in the sample.

17. The method of according to claim 16, wherein the subunit comprises:
   a) a Gln substitution at an amino acid position corresponding to L99 in SEQ ID NO: 1;
   b) a Gly substitution at an amino acid position corresponding to E103 in SEQ ID NO: 1;
   c) a Tyr substitution at an amino acid corresponding to F166 in SEQ ID NO: 1;
   d) an Arg substitution at an amino acid corresponding to K294 in SEQ ID NO: 1; and/or
   e) a Ser substitution at an amino acid corresponding to C285 in SEQ ID NO: 1.

* * * * *

UNITED STATES PATENT AND TRADEMARK OFFICE
CERTIFICATE OF CORRECTION

PATENT NO.       : 11,169,138 B2
APPLICATION NO.  : 15/566577
DATED            : November 9, 2021
INVENTOR(S)      : Giovanni Maglia et al.

It is certified that error appears in the above-identified patent and that said Letters Patent is hereby corrected as shown below:

On the Title Page

Under Item (30) Foreign Application Priority Data:
"Apr 14, 2015  (GB) .......................... 1506307
Apr 29, 2015   (GB) .......................... 1507264"

Should Read:
--Apr. 14, 2015 (GB) .......................... 1506307.6
Apr. 29, 2015  (GB) .......................... 1507264.8--

Signed and Sealed this
Twenty-fourth Day of May, 2022

Katherine Kelly Vidal
*Director of the United States Patent and Trademark Office*

SEQUENCE LISTING

<160> NUMBER OF SEQ ID NOS: 33

<210> SEQ ID NO 1
<211> LENGTH: 303
<212> TYPE: PRT
<213> ORGANISM: Salmonella typhi

<400> SEQUENCE: 1

```
Met Thr Gly Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
```

```
            275                 280                 285
Gln Gln Arg His Gly Lys Lys Thr Leu Phe Glu Val Pro Asp Val
    290                 295                 300

<210> SEQ ID NO 2
<211> LENGTH: 312
<212> TYPE: PRT
<213> ORGANISM: Salmonella typhi

<400> SEQUENCE: 2

Met Thr Gly Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Gln Leu Phe Asp Gly Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Tyr Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Ser Asn Glu Tyr
        275                 280                 285

Gln Gln Arg His Gly Arg Lys Thr Leu Phe Glu Val Pro Asp Val Gly
    290                 295                 300

Ser Ser His His His His His His
305                 310

<210> SEQ ID NO 3
<211> LENGTH: 312
<212> TYPE: PRT
<213> ORGANISM: Salmonella typhi
```

<400> SEQUENCE: 3

```
Met Thr Gly Ile Phe Ala Glu Gln Thr Val Glu Val Val Lys Ser Ala
1               5                   10                  15
Ile Glu Thr Ala Asp Gly Ala Leu Asp Leu Tyr Asn Lys Tyr Leu Asp
            20                  25                  30
Gln Val Ile Pro Trp Lys Thr Phe Asp Glu Thr Ile Lys Glu Leu Ser
        35                  40                  45
Arg Phe Lys Gln Glu Tyr Ser Gln Glu Ala Ser Val Leu Val Gly Asp
    50                  55                  60
Ile Lys Val Leu Leu Met Asp Ser Gln Asp Lys Tyr Phe Glu Ala Thr
65                  70                  75                  80
Gln Thr Val Tyr Glu Trp Ala Gly Val Val Thr Gln Leu Leu Ser Ala
                85                  90                  95
Tyr Ile Gln Leu Phe Asp Gly Tyr Asn Glu Lys Ala Ser Ala Gln
            100                 105                 110
Lys Asp Ile Leu Ile Arg Ile Leu Asp Asp Gly Val Lys Lys Leu Asn
        115                 120                 125
Glu Ala Gln Lys Ser Leu Leu Thr Ser Ser Gln Ser Phe Asn Asn Ala
    130                 135                 140
Ser Gly Lys Leu Leu Ala Leu Asp Ser Gln Leu Thr Asn Asp Phe Ser
145                 150                 155                 160
Glu Lys Ser Ser Tyr Tyr Gln Ser Gln Val Asp Arg Ile Arg Lys Glu
                165                 170                 175
Ala Tyr Ala Gly Ala Ala Ala Gly Ile Val Ala Gly Pro Phe Gly Leu
            180                 185                 190
Ile Ile Ser Tyr Ser Ile Ala Ala Gly Val Val Glu Gly Lys Leu Ile
        195                 200                 205
Pro Glu Leu Asn Asn Arg Leu Lys Thr Val Gln Asn Phe Phe Thr Ser
    210                 215                 220
Leu Ser Ala Thr Val Lys Gln Ala Asn Lys Asp Ile Asp Ala Ala Lys
225                 230                 235                 240
Leu Lys Leu Ala Thr Glu Ile Ala Ala Ile Gly Glu Ile Lys Thr Glu
                245                 250                 255
Thr Glu Thr Thr Arg Phe Tyr Val Asp Tyr Asp Asp Leu Met Leu Ser
            260                 265                 270
Leu Leu Lys Gly Ala Ala Lys Lys Met Ile Asn Thr Ser Asn Glu Tyr
        275                 280                 285
Gln Gln Arg His Gly Arg Lys Thr Leu Phe Glu Val Pro Asp Val Gly
    290                 295                 300
Ser Ser Tyr His His His His
305                 310
```

<210> SEQ ID NO 4
<211> LENGTH: 1194
<212> TYPE: DNA
<213> ORGANISM: Salmonella typhi

<400> SEQUENCE: 4

```
cctgcgtaga taagcaggaa gcaggcagta tttccagctt ctggaatgtt aaagctacaa    60
aagttgtctg gaggtaatag gtaagaatac tttataaaac aggtacttaa ttgcaattta   120
tatatttaaa gaggcaaatg attatgaccg gaatatttgc agaacaaact gtagaggtag   180
ttaaaagcgc gatcgaaacc gcagatgggg cattagatct ttataacaaa tacctcgacc   240
aggtcatccc ctggaagacc tttgatgaaa ccataaaaga gttaagccgt tttaaacagg   300
```

-continued

```
agtactcgca ggaagcttct gttttagttg gtgatattaa agttttgctt atggacagcc      360
aggacaagta ttttgaagcg acacaaactg tttatgaatg gtgtggtgtc gtgacgcaat      420
tactctcagc gtatatttta ctatttgatg aatataatga gaaaaagca tcagcccaga       480
aagacattct cattaggata ttagatgatg gtgtcaagaa actgaatgaa gcgcaaaaat      540
ctctcctgac aagttcacaa agtttcaaca acgcttccgg aaaactgctg cattagata      600
gccagttaac taatgatttt tcggaaaaaa gtagttattt ccagtcacag gtggatagaa      660
ttcgtaagga agcttatgcc ggtgctgcag ccggcatagt cgccggtccg tttggattaa      720
ttatttccta ttctattgct gcgggcgtga ttgaagggaa attgattcca gaattgaata      780
acaggctaaa aacagtgcaa aatttcttta ctagcttatc agctacagtg aaacaagcga      840
ataaagatat cgatgcggca aaattgaaat tagccactga aatagcagca attggggaga      900
taaaaacgga aaccgaaaca accagattct acgttgatta tgatgattta atgctttctt      960
tattaaaagg agctgcaaag aaaatgatta acacctgtaa tgaataccaa caaagacacg     1020
gtaagaagac gcttttcgag gttcctgacg tctgatacat tttcattcga tctgtgtact     1080
tttaacgccc gatagcgtaa agaaaatgag agacggagaa aaagcgatat tcaacagccc     1140
gataaacaag agtcgttacc gggctgacga ggttatcagg cgttaagctg gtag          1194
```

<210> SEQ ID NO 5
<211> LENGTH: 971
<212> TYPE: DNA
<213> ORGANISM: Salmonella typhi

<400> SEQUENCE: 5

```
atgacgggta tctttgcgga acagacggtg gaagttgtga aaagtgcgat tgaaacggct       60
gacggtgcgc tggacctgta taataaatat ctggatcagg tcatcccgtg gaaaaccttt      120
gacgaaacga ttaaagaact gagccgtttc aaacaggaat acagtcaaga agcgtccgtc      180
ctggtgggcg atatcaaagt gctgctgatg gattctcagg acaaatattt tgaagctacc      240
caaacggttt acgaatggtg tggtgtggtt acccagctgc tgtccgcata tattcagctg      300
ttcgatggat acaacgagaa aaagcgagc gcgcagaaag acattctgat ccgcattctg      360
gatgacggcg tgaaaaaact gaatgaagcc cagaaatcgc tgctgaccag ctctcaatca      420
tttaacaatg cctcgggtaa actgctggca ctggatagcc agctgacgaa cgactttttct    480
gaaaaaagtt cctattacca gagccaagtc gatcgtattc gtaaagaagc ctacgcaggt      540
gccgcagcag gtattgtggc cggtccgttc ggtctgatta tctcatattc gattgctgcg      600
ggcgttatcg aaggtaaact gattccggaa ctgaacaatc gtctgaaaac cgttcagaac      660
tttttcacca gtctgtctgc tacggtcaaa caagcgaata agatatcga cgccgcaaaa       720
ctgaaactgg ccacggaaat cgctgcgatt ggcgaaatca aaccgaaac ggaaccacg        780
cgcttttatg ttgattacga tgacctgatg ctgagcctgc tgaaaggtgc gcgaagaaa       840
atgattaata cctctaatga atatcagcag cgtcacggta gaaaaaccct gtttgaagtc      900
ccggatgtgg gcagcagcca ccaccatcat caccactaaa agcttggatc cggctgctaa      960
caaagcccga a                                                          971
```

<210> SEQ ID NO 6
<211> LENGTH: 945
<212> TYPE: DNA
<213> ORGANISM: Salmonella typhi

<400> SEQUENCE: 6

```
atgacgggta tctttgcgga acagacggtg gaagttgtga aaagtgcgat tgaaacggct      60
gacggtgcgc tggacctgta taataaatat ctggatcagg tcatcccgtg gaaaaccttt     120
gacgaaacga ttaaagaact gagccgtttc aaacaggaat acagtcaaga agcgtccgtc     180
ctagtgggcg atatcaaagt gctgctgatg gattctcagg acaaatattt tgaagctacc     240
caaacggttt acgaatgggc gggtgtggtt acccagctgc tgtccgcata tattcagctg     300
ttcgatggat acaatgagaa aaagcgagc gcgcagaaag acattctgat ccgcattctg      360
gatgacggcg tgaaaaaact gaatgaagcc cagaaatcgc tgctgaccag ctctcaatca     420
tttaacaatg cctcgggtaa actgctggca ctggatagcc agctgacgaa cgactttct      480
gaaaaaagtt cctattacca gagccaagtc gatcgtattc gtaaagaagc ctacgcaggt     540
gccgcagcag gtattgtggc cggtccgttc ggtctgatta tctcatattc aattgctgcg     600
ggcgttgtcg aaggtaaact gattccggaa ctgaacaatc gtctgaaaac cgttcagaac     660
ttttttcacca gtctgtctgc tacggtcaaa caagcgaata agatatcga cgccgcaaaa     720
ctgaaactgg ccacggaaat cgctgcgatt ggcgaaatca aaccgaaac ggaaaccacg      780
cgcttttatg ttgattacga tgacctgatg ctgagcctgc tgaaaggtgc cgcgaagaaa     840
atgattaata cctctaatga atatcagcag cgtcacggta gaaaaaccct gtttgaagtc     900
ccggatgtgg gcagcagcta ccaccatcat caccactaaa gctt                      945
```

<210> SEQ ID NO 7
<211> LENGTH: 228
<212> TYPE: PRT
<213> ORGANISM: Artificial Sequence
<220> FEATURE:
<223> OTHER INFORMATION: Synthetic construct

<400> SEQUENCE: 7

```
Met Ala Leu Asp Leu Phe Ala Asp Ala Glu Pro Trp Gln Glu Pro Leu
 1               5                  10                  15

Ala Ala Gly Ala Val Ile Leu Arg Arg Phe Ala Phe Asn Ala Ala Glu
             20                  25                  30

Gln Leu Ile Arg Asp Ile Asn Asp Val Ala Ser Gln Ser Pro Phe Arg
         35                  40                  45

Gln Met Val Thr Pro Gly Gly Tyr Thr Met Ser Val Ala Met Thr Asn
     50                  55                  60

Cys Gly His Leu Gly Trp Thr Thr His Arg Gln Gly Tyr Leu Tyr Ser
 65                  70                  75                  80

Pro Ile Asp Pro Gln Thr Asn Lys Pro Trp Pro Ala Met Pro Gln Ser
                 85                  90                  95

Phe His Asn Leu Cys Gln Arg Ala Ala Thr Ala Ala Gly Tyr Pro Asp
            100                 105                 110

Phe Gln Pro Asp Ala Cys Leu Ile Asn Arg Tyr Ala Pro Gly Ala Lys
        115                 120                 125

Leu Ser Leu His Gln Asp Lys Asp Glu Pro Asp Leu Arg Ala Pro Ile
    130                 135                 140

Val Ser Val Ser Leu Gly Leu Pro Ala Ile Phe Gln Phe Gly Gly Leu
145                 150                 155                 160

Lys Arg Asn Asp Pro Leu Lys Arg Leu Leu Leu Glu His Gly Asp Val
                165                 170                 175

Val Val Trp Gly Gly Glu Ser Arg Leu Phe Tyr His Gly Ile Gln Pro
            180                 185                 190
```

Leu Lys Ala Gly Phe His Pro Leu Thr Ile Asp Cys Arg Tyr Asn Leu
    195                 200                 205

Thr Phe Arg Gln Ala Gly Lys Lys Glu Gly Ser Ala Trp Ser His Pro
    210                 215                 220

Gln Phe Glu Lys
225

<210> SEQ ID NO 8
<211> LENGTH: 694
<212> TYPE: DNA
<213> ORGANISM: Artificial Sequence
<220> FEATURE:
<223> OTHER INFORMATION: Synthetic construct

<400> SEQUENCE: 8

```
atggcgttgg atctgtttgc cgatgctgaa ccgtggcaag agccactggc ggctggtgcg      60
gtaattttac ggcgttttgc ttttaacgct gcggagcaac tgatccgcga tattaatgac     120
gttgccagcc agtcgccgtt tcgccagatg gtcaccccg ggggatatac catgtcggtg      180
gcgatgacca actgtgggca tctgggctgg acgacccatc ggcaaggtta tctctattcg     240
cccattgatc cgcaaacaaa taaaccgtgg cccgccatgc cacagagttt tcataattta     300
tgtcaacgtg cggctacggc ggcgggctat ccagatttcc agccagatgc ttgtcttatc     360
aaccgctacg ctcctggcgc gaaactgtcg ctgcatcagg ataaagacga accggatctg     420
cgcgcgccaa ttgtttctgt ttctctgggc ttacccgcga ttttcaatt tggcggcctg      480
aaacgaaatg atccgctcaa cgtttgttg ttggaacatg gcgatgtggt ggtatggggc      540
ggtgaatcgc ggctgttta tcacggtatt caaccgttga agcggggtt tcatccactc       600
accatcgact gccgctacaa cctgacattc cgtcaggcag gtaaaaaaga aggcagcgcg     660
tggagccatc cgcagtttga aaatgataa gctt                                  694
```

<210> SEQ ID NO 9
<211> LENGTH: 691
<212> TYPE: DNA
<213> ORGANISM: Artificial Sequence
<220> FEATURE:
<223> OTHER INFORMATION: Synthetic construct

<400> SEQUENCE: 9

```
atggcttcgg ctatgatttc tctgattgcg gcactggctg tcgatcgtgt tattggtatg      60
gaaaacgcta tgccgtggaa tctgccggct gatctggcgt ggtttaaacg taacactctg     120
gacaagccgg tcattatggg ccgccatacg tgggaaagca tcggtcgtcc gctgccgggt     180
cgcaaaaata ttatcctgag cagccagccg ggcaccgatg accgtgtgac gtgggttaag     240
agcgtcgatg aagcaattgc ggcggcaggc gacgtgccgg aaattatggt tatcggcggt     300
ggccgcgttt atgaacagtt cctgccgaaa gcccaaaagc tgtacctgac ccatatcgat     360
gcagaagtcg aaggtgatac gcactttccg gactatgaac cggatgactg ggaaagtgtg     420
ttctccgaat tcacgacgc cgacgctcag aacagccact catactcatt cgaaatcctg      480
gaacgccgtg gcagcagtac tcgagcgaaa gaaccgcgg cggcgaaatt tgaacgccag      540
catatggata gcggcagcgc gaaaattgcc gcacttaaac aaaaaatcgc ggcgctgaag     600
tataaaaatg cggcactaaa aaagaagatt gcggccctaa acagggcag cgcgtggagc      660
catccgcagt ttgaaaaatg ataagcttgg a                                    691
```

```
<210> SEQ ID NO 10
<211> LENGTH: 226
<212> TYPE: PRT
<213> ORGANISM: Artificial Sequence
<220> FEATURE:
<223> OTHER INFORMATION: Synthetic construct

<400> SEQUENCE: 10

Met Ala Ser Ala Met Ile Ser Leu Ile Ala Ala Leu Ala Val Asp Arg
1               5                   10                  15

Val Ile Gly Met Glu Asn Ala Met Pro Trp Asn Leu Pro Ala Asp Leu
            20                  25                  30

Ala Trp Phe Lys Arg Asn Thr Leu Asp Lys Pro Val Ile Met Gly Arg
        35                  40                  45

His Thr Trp Glu Ser Ile Gly Arg Pro Leu Pro Gly Arg Lys Asn Ile
    50                  55                  60

Ile Leu Ser Ser Gln Pro Gly Thr Asp Asp Arg Val Thr Trp Val Lys
65                  70                  75                  80

Ser Val Asp Glu Ala Ile Ala Ala Gly Asp Val Pro Glu Ile Met
                85                  90                  95

Val Ile Gly Gly Gly Arg Val Tyr Glu Gln Phe Leu Pro Lys Ala Gln
            100                 105                 110

Lys Leu Tyr Leu Thr His Ile Asp Ala Glu Val Glu Gly Asp Thr His
        115                 120                 125

Phe Pro Asp Tyr Glu Pro Asp Asp Trp Glu Ser Val Phe Ser Glu Phe
    130                 135                 140

His Asp Ala Asp Ala Gln Asn Ser His Ser Tyr Ser Phe Glu Ile Leu
145                 150                 155                 160

Glu Arg Arg Gly Ser Ser Thr Arg Ala Lys Glu Thr Ala Ala Ala Lys
                165                 170                 175

Phe Glu Arg Gln His Met Asp Ser Gly Ser Ala Lys Ile Ala Ala Leu
            180                 185                 190

Lys Gln Lys Ile Ala Ala Leu Lys Tyr Lys Asn Ala Ala Leu Lys Lys
        195                 200                 205

Lys Ile Ala Ala Leu Lys Gln Gly Ser Ala Trp Ser His Pro Gln Phe
    210                 215                 220

Glu Lys
225

<210> SEQ ID NO 11
<211> LENGTH: 66
<212> TYPE: PRT
<213> ORGANISM: Artificial Sequence
<220> FEATURE:
<223> OTHER INFORMATION: Synthetic construct

<400> SEQUENCE: 11

Glu Arg Arg Gly Ser Ser Thr Arg Ala Lys Glu Thr Ala Ala Ala Lys
1               5                   10                  15

Phe Glu Arg Gln His Met Asp Ser Gly Ser Ala Lys Ile Ala Ala Leu
            20                  25                  30

Lys Gln Lys Ile Ala Ala Leu Lys Tyr Lys Asn Ala Ala Leu Lys Lys
        35                  40                  45

Lys Ile Ala Ala Leu Lys Gln Gly Ser Ala Trp Ser His Pro Gln Phe
    50                  55                  60

Glu Lys
65
```

<210> SEQ ID NO 12
<211> LENGTH: 29
<212> TYPE: PRT
<213> ORGANISM: Artificial Sequence
<220> FEATURE:
<223> OTHER INFORMATION: Synthetic construct

<400> SEQUENCE: 12

Glu Arg Arg Gly Ser Ser Thr Arg Ala Lys Lys Lys Ile Ala Ala Leu
1               5                   10                  15

Lys Gln Gly Ser Ala Trp Ser His Pro Gln Phe Glu Lys
            20                  25

<210> SEQ ID NO 13
<211> LENGTH: 28
<212> TYPE: PRT
<213> ORGANISM: Artificial Sequence
<220> FEATURE:
<223> OTHER INFORMATION: Synthetic construct

<400> SEQUENCE: 13

Glu Arg Arg Gly Ser Ser Thr Arg Ala Lys Lys Ile Ala Ala Leu Lys
1               5                   10                  15

Gln Gly Ser Ala Trp Ser His Pro Gln Phe Glu Lys
            20                  25

<210> SEQ ID NO 14
<211> LENGTH: 20
<212> TYPE: PRT
<213> ORGANISM: Artificial Sequence
<220> FEATURE:
<223> OTHER INFORMATION: Synthetic construct

<400> SEQUENCE: 14

Glu Arg Arg Gly Ser Ser Thr Arg Ala Gly Ser Ala Trp Ser His Pro
1               5                   10                  15

Gln Phe Glu Lys
            20

<210> SEQ ID NO 15
<211> LENGTH: 15
<212> TYPE: PRT
<213> ORGANISM: Artificial Sequence
<220> FEATURE:
<223> OTHER INFORMATION: Synthetic construct

<400> SEQUENCE: 15

Lys Glu Thr Ala Ala Ala Lys Phe Glu Arg Gln His Met Asp Ser
1               5                   10                  15

<210> SEQ ID NO 16
<211> LENGTH: 28
<212> TYPE: PRT
<213> ORGANISM: Artificial Sequence
<220> FEATURE:
<223> OTHER INFORMATION: Synthetic construct

<400> SEQUENCE: 16

Lys Ile Ala Ala Leu Lys Gln Lys Ile Ala Ala Leu Lys Tyr Lys Asn
1               5                   10                  15

Ala Ala Leu Lys Lys Lys Ile Ala Ala Leu Lys Gln
            20                  25

<210> SEQ ID NO 17

```
<211> LENGTH: 8
<212> TYPE: PRT
<213> ORGANISM: Artificial Sequence
<220> FEATURE:
<223> OTHER INFORMATION: Synthetic construct

<400> SEQUENCE: 17

Trp Ser His Pro Gln Phe Glu Lys
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic construct

<400> SEQUENCE: 18

Gly Ser Ser Thr Arg Ala
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic construct

<400> SEQUENCE: 19

Gly Ser Ser Thr Arg Ala Gly Ser Ala
1               5

<210> SEQ ID NO 20
<211> LENGTH: 41
<212> TYPE: DNA
<213> ORGANISM: Artificial Sequence
<220> FEATURE:
<223> OTHER INFORMATION: Synthetic construct

<400> SEQUENCE: 20
agatatagcc atggcgttgg atctgtttgc cgatgctgaa c                    41

<210> SEQ ID NO 21
<211> LENGTH: 47
<212> TYPE: DNA
<213> ORGANISM: Artificial Sequence
<220> FEATURE:
<223> OTHER INFORMATION: Synthetic contruct

<400> SEQUENCE: 21
cggatggctc cacgcgctgc cttcttttt acctgcctga cggaatg               47

<210> SEQ ID NO 22
<211> LENGTH: 50
<212> TYPE: DNA
<213> ORGANISM: Artificial Sequence
<220> FEATURE:
<223> OTHER INFORMATION: Synthetic construct

<400> SEQUENCE: 22
tatatataag cttatcattt ttcaaactgc ggatggctcc acgcgctgcc           50

<210> SEQ ID NO 23
<211> LENGTH: 50
<212> TYPE: DNA
<213> ORGANISM: Artificial Sequence
<220> FEATURE:
```

<223> OTHER INFORMATION: Synthetic construct

<400> SEQUENCE: 23
gccagatgct tgtcttatca accgctacgc tcctggcgcg aaactgtcgc          50

<210> SEQ ID NO 24
<211> LENGTH: 19
<212> TYPE: DNA
<213> ORGANISM: Artificial Sequence
<220> FEATURE:
<223> OTHER INFORMATION: Synthetic construct

<400> SEQUENCE: 24
gctagttatt gctcagcgg                                            19

<210> SEQ ID NO 25
<211> LENGTH: 40
<212> TYPE: DNA
<213> ORGANISM: Artificial Sequence
<220> FEATURE:
<223> OTHER INFORMATION: Synthetic construct

<400> SEQUENCE: 25
tgcctagcgt ttcattgtcc cttcttatta ggtgataata                     40

<210> SEQ ID NO 26
<211> LENGTH: 42
<212> TYPE: DNA
<213> ORGANISM: Artificial Sequence
<220> FEATURE:
<223> OTHER INFORMATION: Synthetic construct

<400> SEQUENCE: 26
atatatatat ccatggcttc ggctatgatt tctctgattg cg                  42

<210> SEQ ID NO 27
<211> LENGTH: 55
<212> TYPE: DNA
<213> ORGANISM: Artificial Sequence
<220> FEATURE:
<223> OTHER INFORMATION: Synthetic construct

<400> SEQUENCE: 27
cgcggtttct ttcgctcgag tactgctgcc acggcgttcc aggatttcga atgag    55

<210> SEQ ID NO 28
<211> LENGTH: 55
<212> TYPE: DNA
<213> ORGANISM: Artificial Sequence
<220> FEATURE:
<223> OTHER INFORMATION: Synthetic construct

<400> SEQUENCE: 28
ctcattcgaa atcctggaac gccgtggcag cagtactcga gcgaaagaaa ccgcg    55

<210> SEQ ID NO 29
<211> LENGTH: 40
<212> TYPE: DNA
<213> ORGANISM: Artificial Sequence
<220> FEATURE:
<223> OTHER INFORMATION: Synthetic construct

<400> SEQUENCE: 29
atatatatat aagcttatca tttttcaaac tgcggatggc                     40

```
<210> SEQ ID NO 30
<211> LENGTH: 45
<212> TYPE: DNA
<213> ORGANISM: Artificial Sequence
<220> FEATURE:
<223> OTHER INFORMATION: Synthetic construct

<400> SEQUENCE: 30
atatatatat ctcgagtact gctgccacgg cgttccagga tttcg               45

<210> SEQ ID NO 31
<211> LENGTH: 46
<212> TYPE: DNA
<213> ORGANISM: Artificial Sequence
<220> FEATURE:
<223> OTHER INFORMATION: Synthetic construct

<400> SEQUENCE: 31
atatatatat ctcgagcggg cagcgcgtgg agccatccgc agtttg              46

<210> SEQ ID NO 32
<211> LENGTH: 44
<212> TYPE: DNA
<213> ORGANISM: Artificial Sequence
<220> FEATURE:
<223> OTHER INFORMATION: Synthetic construct

<400> SEQUENCE: 32
atatatatat ctcgagcgaa gaagattgcg gccctaaaac aggg                44

<210> SEQ ID NO 33
<211> LENGTH: 47
<212> TYPE: DNA
<213> ORGANISM: Artificial Sequence
<220> FEATURE:
<223> OTHER INFORMATION: Synthetic construct

<400> SEQUENCE: 33
atatatatat ctcgagcgaa aaagaagatt gcggccctaa aacaggg             47
```